(12) United States Patent
Yamamoto et al.

(10) Patent No.: US 10,557,120 B2
(45) Date of Patent: Feb. 11, 2020

(54) OSTEOBLAST AND METHOD FOR PREPARING SAME

(71) Applicant: KYOTO PREFECTURAL PUBLIC UNIVERSITY CORPORATION, Kyoto-shi, Kyoto (JP)

(72) Inventors: Kenta Yamamoto, Kyoto (JP); Tsunao Kishida, Kyoto (JP); Toshiro Yamamoto, Kyoto (JP); Osam Mazda, Kyoto (JP)

(73) Assignee: KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 380 days.

(21) Appl. No.: 14/906,948

(22) PCT Filed: Jul. 24, 2014

(86) PCT No.: PCT/JP2014/069628
§ 371 (c)(1),
(2) Date: Jan. 22, 2016

(87) PCT Pub. No.: WO2015/012377
PCT Pub. Date: Jan. 29, 2015

(65) Prior Publication Data
US 2016/0160180 A1    Jun. 9, 2016

(30) Foreign Application Priority Data

Jul. 26, 2013 (JP) .................................. 2013-156025
Jan. 27, 2014 (JP) .................................. 2014-012441

(51) Int. Cl.
*C12N 5/077* (2010.01)
*C12N 15/85* (2006.01)

(52) U.S. Cl.
CPC ............ *C12N 5/0654* (2013.01); *C12N 15/85* (2013.01)

(58) Field of Classification Search
None
See application file for complete search history.

(56) References Cited

U.S. PATENT DOCUMENTS

| 8,278,036  | B2 | 10/2012 | Kariko et al. |
| 8,404,442  | B2 | 3/2013  | Basilico |
| 8,691,966  | B2 | 4/2014  | Kariko et al. |
| 8,748,089  | B2 | 6/2014  | Kariko et al. |
| 8,808,982  | B2 | 8/2014  | Dahl et al. |
| 8,835,108  | B2 | 9/2014  | Kariko et al. |
| 9,012,219  | B2 | 4/2015  | Kariko et al. |
| 9,163,213  | B2 | 10/2015 | Kariko et al. |
| 9,371,511  | B2 | 6/2016  | Kariko et al. |
| 9,371,544  | B2 | 6/2016  | Dahl et al. |
| 9,750,824  | B2 | 9/2017  | Kariko et al. |
| 2009/0286852 | A1 | 11/2009 | Kariko et al. |
| 2011/0143397 | A1 | 6/2011  | Kariko et al. |
| 2011/0143436 | A1 | 6/2011  | Dahl et al. |
| 2012/0164110 | A1 | 6/2012  | Feinberg et al. |
| 2013/0111615 | A1 | 5/2013  | Kariko et al. |
| 2013/0189741 | A1 | 7/2013  | Meis et al. |
| 2013/0197068 | A1 | 8/2013  | Kariko et al. |
| 2013/0261172 | A1 | 10/2013 | Kariko et al. |
| 2014/0315988 | A1 | 10/2014 | Dahl et al. |
| 2014/0328825 | A1 | 11/2014 | Meis et al. |
| 2015/0038558 | A1 | 2/2015  | Kariko et al. |
| 2015/0184123 | A1 | 7/2015  | Kariko et al. |
| 2015/0315572 | A1 | 11/2015 | Kariko et al. |
| 2016/0251629 | A1 | 9/2016  | Dahl et al. |
| 2016/0369243 | A1 | 12/2016 | Kariko et al. |
| 2017/0043037 | A1 | 2/2017  | Kariko et al. |

FOREIGN PATENT DOCUMENTS

| CN | 102947450 | 2/2013 |
| WO | 2008/127256 | 10/2008 |

OTHER PUBLICATIONS

Mizoshiri et al., Biochem. Biophys. Res. Commun., 2015, 467: 1110-1116.*
De Jong et al., J. Bone Miner. Res., 2004, 19: 947-958.*
Seo et al., Cell Reports, 2013, 3: 2075-2087.*
Owen et al., J. Cell. Physiol., 1990, 143: 420-430.*
Bustos-Valenzuela et al., BMC Research Notes, 2011, 4: 1-15.*
Barba et al., J. Biomed. Biotechnol., 2012, p. 1-11.*
Dansranjavin et al., Cell Cycle, 2009, 8: 916-924.*
Okita et al., Nature, 2007, 448: 313-318.*
Nakashinna et al., Cell, 2002, 108: 17-29.*
Han et al., Cell Stem Cell, 2012, 10: 465-472.*
Takahashi et al., "Induction of Pluripotent Stem Cells from Adult Human Fibroblasts by Defined Factors", Cell, 131: 861-872 (2007).
Takahashi et al., "Induction of Pluripotent Stem Cells from Mouse Embryonic and Adult Fibroblast Cultures by Defined Factors", Cell, 126: 663-676 (2006).
Tashiro, "Optimization of Adenovirus Vectors for Transduction in Embryonic Stem Cells and Induced Pluripotent Stem Cells", Yakugaku Zasshi, 131(9): 1333-1338 (2011).
Kawabata et al., "Differentiation of Functional Cells from iPS Cells by Efficient Gene Transfer", Yakugaku Zasshi, 130(11): 1527-1534 (2010).

(Continued)

*Primary Examiner* — Ileana Popa
(74) *Attorney, Agent, or Firm* — Wenderoth, Lind & Ponack, L.L.P.

(57) ABSTRACT

The present invention relates to: a method of preparing an osteoblast from a somatic cell of a mammal, the method including introducing a bone-related gene or an expression product thereof and a reprogramming-related gene or an expression product thereof, or introducing a reprogramming-related gene or an expression product thereof independently into the somatic cell, the bone-related gene including at least one kind selected from the group consisting of Runx2 (R), Osterix (O), and Dlx5 (D), the reprogramming-related gene including at least one kind selected from the group consisting of Oct family, c-Myc (M), L-Myc (L), Klf family, Lin-28, and Sox2; and an osteoblast prepared by the method.

6 Claims, 56 Drawing Sheets

Specification includes a Sequence Listing.

(56) References Cited

OTHER PUBLICATIONS

Lee et al., "Enhancement of Bone Regeneration by Gene Delivery of BMP2/Runx2 Bicistronic Vector into Adipose-derived Stromal Cells", Biomaterials, 31: 5652-5659 (2010).

Kato et al., "Bone Morphogenetic Protein-2 Induces the Differentiation of a Mesenchymal Progenitor Cell Line, ROB-C26, into Mature Osteoblasts and Adipocytes", Life Sciences, 84: 302-310 (2009).

Tsumaki, "Direct Induction of Chondrogenic Cells from Mouse Dermal Fibroblast Culture", Journal of Clinical and Experimental Medicine, 239(14): 1332-1337 (2011).

Takeyasu et al., "In Vitro Osteogenic Differentiation Potential of Dental Pulp Stem Cells", J. Oral Tissue Engin., 2(1): 25-30 (2004).

Karner et al., "Differentiation of Human Embryonic Stem Cells into Osteogenic or Hematopoietic Lineages: A Dose-Dependent Effect of Osterix Over-Expression", Journal of Cellular Physiology, 218: 323-333 (2009).

Li et al., "Derivation of Murine Induced Pluripotent Stem Cells (iPS) and Assessment of Their Differentiation Toward Osteogenic Lineage", Journal of Cellular Biochemistry, 109: 643-652 (2010).

Bilousova et al., "Osteoblasts Derived from Induced Pluripotent Stem Cells form Calcified Structures in Scaffolds both In Vitro and In Vivo", Stem Cells, 29(2): 206-216 (2011).

Tashiro et al., "Efficient Adipocyte and Osteblast Differentiation from Mouse Induced Pluripotent Stem Cells by Adenoviral Transduction", Stem Cells, 27: 1802-1811 (2009).

Kim et al., "Direct Reprogramming of Human Neural Stem Cells by OCT4", Nature, 461: 649-653 (2009).

Kim et al., "OCT4-Induced Pluripotency in Adult Neural Stem Cells", Cell, 136: 411-419 (2009).

Nakagawa et al., "Promotion of Direct Reprogramming by Transformation-Deficient Myc", PNAS, 107(32): 14152-14157 (2010).

Pang et al., "Induction of Human Neuronal Cells by Defined Transcription Factors", Nature, 476(7359): 220-223 (2011).

Lyssiotis et al., "Reprogramming of Murine Fibroblasts to Induced Pluripotent Stem Cells with Chemical Complementation of Klf4", PNAS, 106(22): 8912-8917 (2009).

Ieda et al., "Direct Reprogramming of Fibroblasts into Functional Cardiomyocytes by Defined Factors", Cell, 142: 375-386 (2010).

Vierbuchen et al., "Direct Conversion of Fibroblasts to Functional Neurons by Defined Factors", Nature, 463(7284): 1035-1041 (2010).

Hiramatsu et al., "Generation of Hyaline Cartilaginous Tissue from Mouse Adult Dermal Fibroblast Culture by Defined Factors", The Jornal of Clinical Investigation, 121(2): 640-657 (2011).

Huang et al., "Induction of Functional Hepatocyte-like Cells from Mouse Fibroblasts by Defined Factors", Nature, 475: 386-389 (2011).

Sekiya et al., "Direct Conversion of Mouse Fibroblasts to Hepatocyte-like Cells by Defined Factors", Nature, 475: 390-393 (2011).

Zhou et al., "Generation of Induced Pluripotent Stem Cells Using Recombinant Proteins", Cell Stem Cell, 4(5): 381-384 (2009).

Kim et al., "Generation of Human Induced Pluripotent Stem Cells by Direct Delivery of Reporogramming Proteins", Cell Stem Cell, 4(6): 472-476 (2009).

International Search Report dated Oct. 7, 2014 in application No. PCT/JP2014/069628.

Extended European Search Report dated Feb. 24, 2017 in corresponding European Application No. 14829754.2.

Guzzo et al., "Efficient Differentiation of Human iPSC-Derived Mesenchymal Stem Cells to Chondroprogenitor Cells", Journal of Cellular Biochemistry, 114(2):480-490 (2013).

Li et al., "Cells derived from murine induced pluripotent stem cells (iPSC) by treatment with members of TGF-beta family give rise to osteoblasts differentiation and form bone in vivo", BMC Cell Biology, 13(1):35 (2012).

Yamamoto et al., "Direct conversion of human fibroblasts into functional osteoblasts by defined factors", Proceedings of the National Academy of Sciences, 112(19):6152-6157 (2015).

Office Action issuing in counterpart Chinese application No. 201480048547.7, dated Feb. 6, 2018.

* cited by examiner

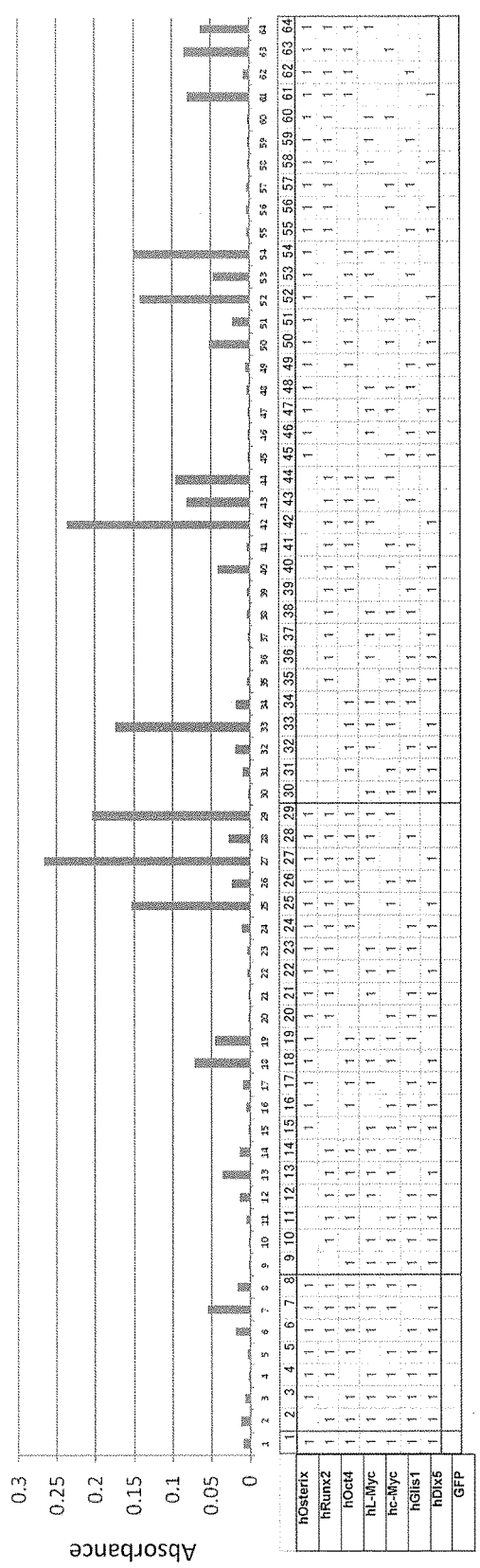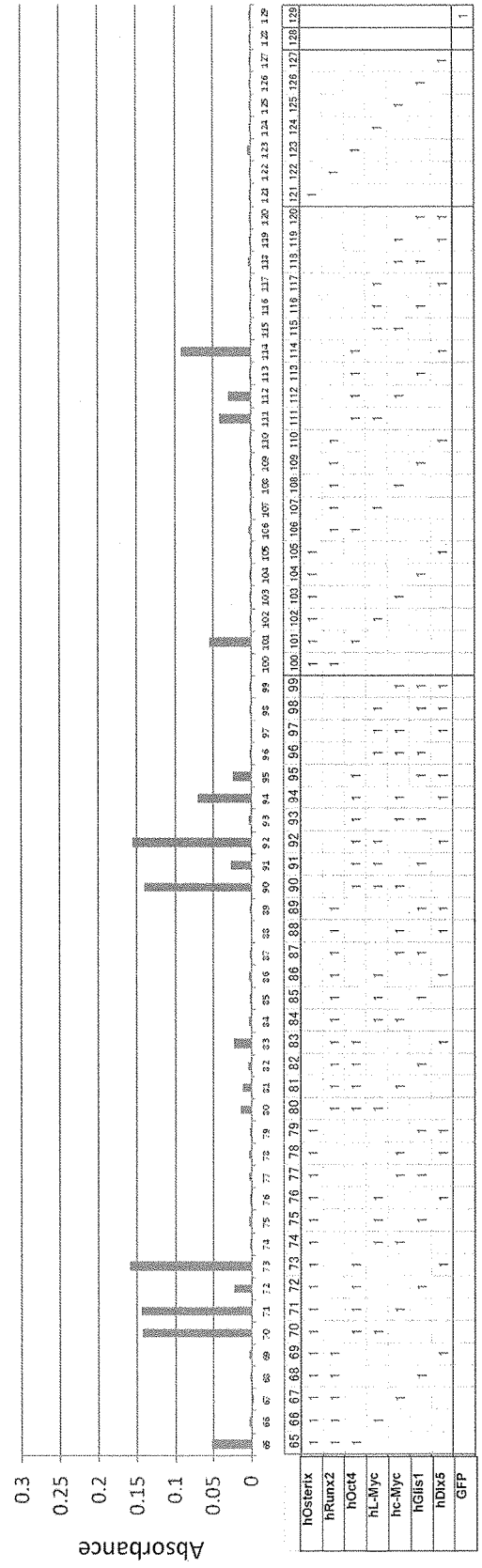
Fig. 3H

Fig. 3I
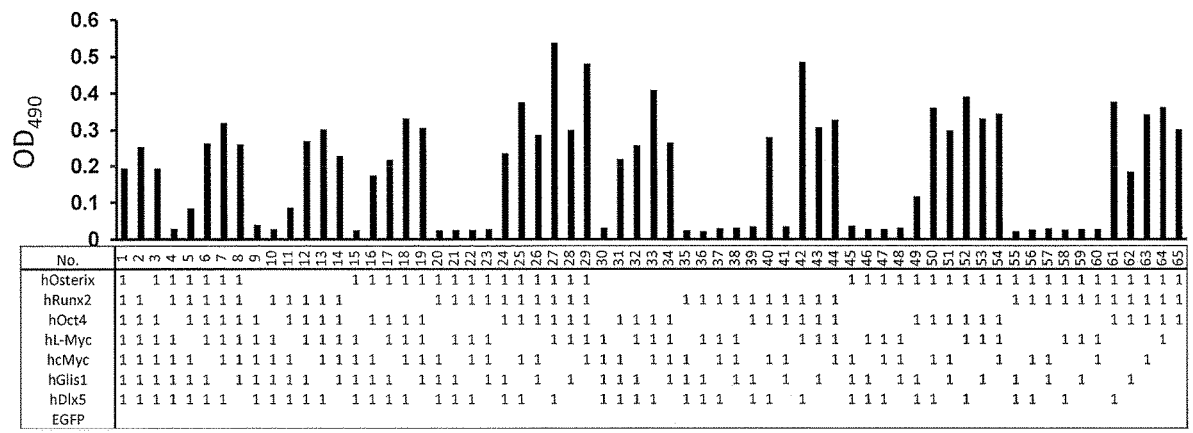
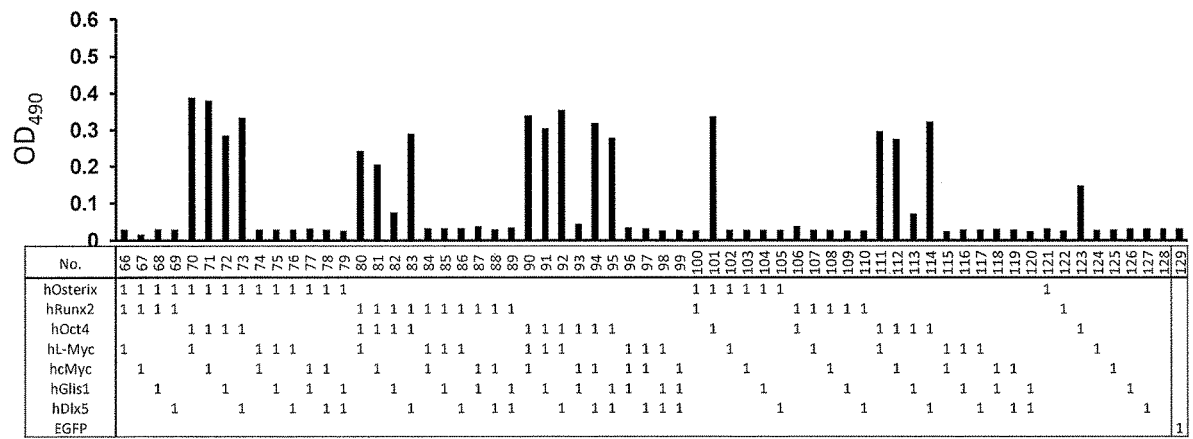

Fig. 4        Gin-1
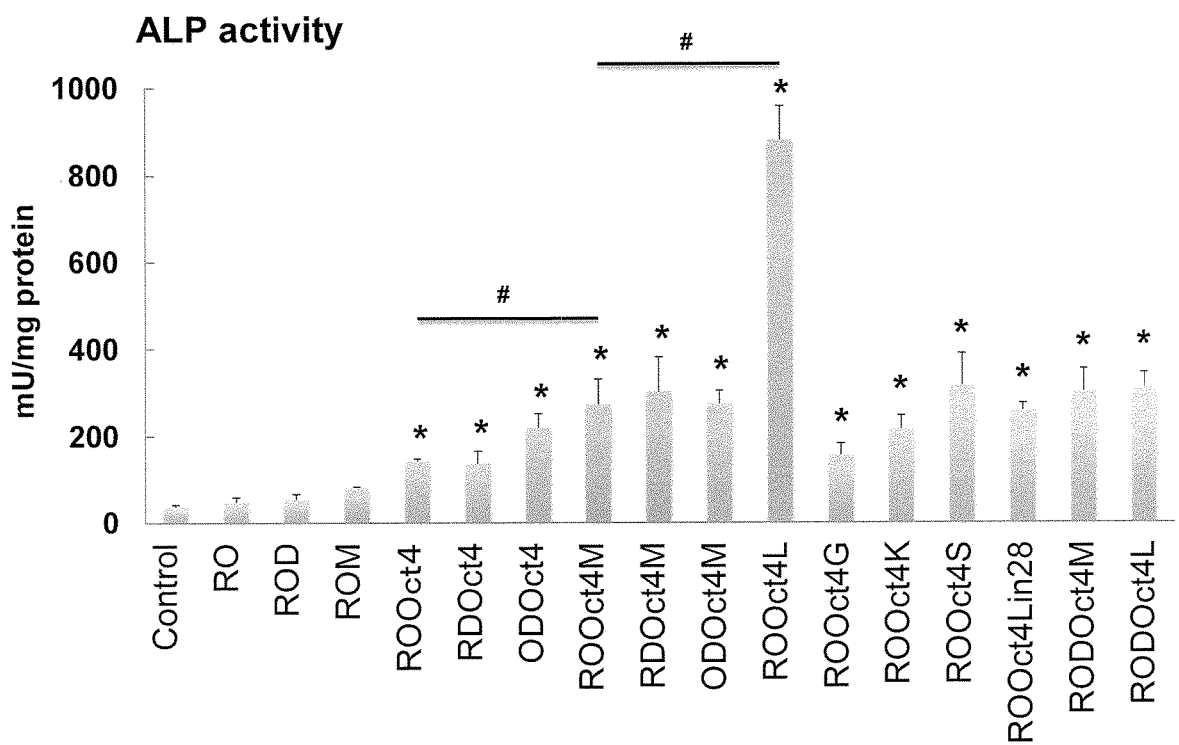

Gin-1

×100

A: control
B: ROOct4M
C: ROOct4L

A: control; B: ROOct4M; C: ROOct4L; D: control; E: ROOct4M; F: ROOct4L

Gin-1

×1

A: Background
B: ROOct4L

Gin-1

A: Background; B: Control; C: ROOct4M; D: ROOct4L

A: control; B: ROOct4M; C: ROOct4L; D: control; E: ROOct4M; F: ROOct4L

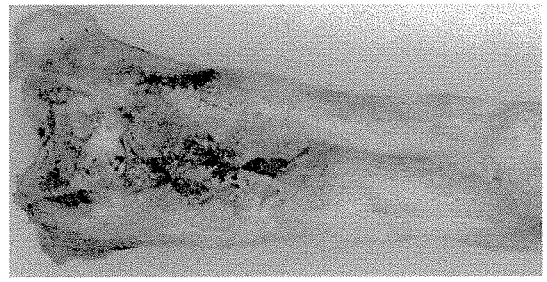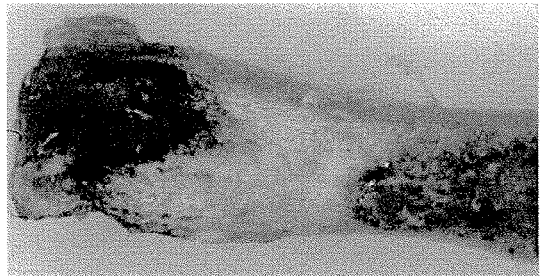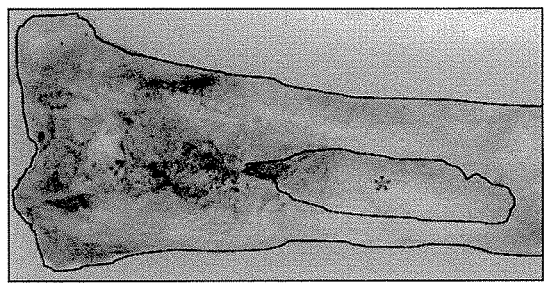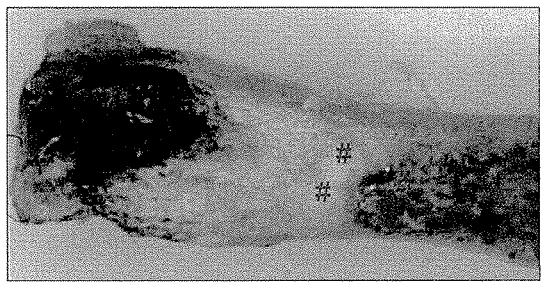
Human gingival fibroblasts      Human dOBs
Graft
Fig. 20

(Sham operated) | Human gingival fibroblasts | Human dOBs

Graft

Fig. 23

| Target | Primer | Sequence |
|---|---|---|
| hRunx2 | Forward | 5'-ATCCCAGTGTGGTGGTACGGGCCCACCATGCGTATTCCCGTAGAT-3' |
| | Reverse | 5'-TAGCGACCGGCGCTCAGCTGGGAGGCCCTAATATGGTCGCCAAAC-3' |
| hOsterix | Forward | 5'-ATCCCAGTGTGGTGGTACGGGCTCAGGATGGCGTCCTCCCTGCTT-3' |
| | Reverse | 5'-TAGCGACCGGCGCTCAGCTGGCCCGGCTCAGATCTCCAGCAAGTT-3' |
| hDlx5 | Forward | 5'-ATCCCAGTGTGGTGGTACGGGATGACAGGAGTGTTTGACAGA-3' |
| | Reverse | 5'-TAGCGACCGGCGCTCAGCTGGCTAATAGAGTGTCCCGGAGGC-3' |

Fig. 24

| Target | Primer | Sequence |
|---|---|---|
| pMXs.hRunx2 | seq 1 | 5'-GTCCGCCGACACCAGACTAAG-3' |
| | seq 2 | 5'-AGCCTGCAGCCCGGCAAAATG-3' |
| | seq 3 | 5'-AACTTCCTGTGCTCGGTGCTG-3' |
| | seq 4 | 5'-AATTAAAGTTACAGTAGATGG-3' |
| | seq 5 | 5'-ATGACCAGTCTTACCCCTCCT-3' |
| | seq 6 | 5'-AATGCACTATCCAGCCACCTT-3' |
| | seq 7 | 5'-AATGGCAGCACGCTATTAAAT-3' |
| pMXs.hOsterix | seq 1 | 5'-CACGTGAAGGCTGCCGACCCCGGG-3' |
| | seq 2 | 5'-GTGACCTTTCAGCCTCCAAAACCA-3' |
| | seq 3 | 5'-AACACTCCTACTCCATGGTGGGAT-3' |
| | seq 4 | 5'-ACGGGGTGCAAGCACTGGGGGTAG-3' |
| | seq 5 | 5'-AGTTCACCTGCCTGCTCTGCTCCA-3' |
| pMXs.hDlx5 | seq 1 | 5'-TTACTAACAGCCCCTCTCTCC-3' |
| | seq 2 | 5'-AGAAGGGTCCCCAGCATCCGA-3' |
| | seq 3 | 5'-ACAACCGCGTCCCAAGCGCCA-3' |
| | seq 4 | 5'-ACCCTCATGCCCACCCTCCGA-3' |

Fig. 25

| Target | Primer | Description |
|---|---|---|
| hβ-actin | Forward | Applied Bioscience Hs00287164-m1 |
| | Reverse | |
| hOC | Forward | 5'-TGAGAGCCCTCACACTCCTC-3' |
| | Reverse | 5'-ACCTTTGCTGGACTCTGCAC-3' |
| hOPN | Forward | Applied Bioscience Hs00959010-m1 |
| | Reverse | |
| hBSP | Forward | 5'-CAATCTGTGCCACTCACTGC-3' |
| | Reverse | 5'-CAGTCTTCATTTTGGTGATTGC-3' |
| hMMP-13 | Forward | Applied Bioscience Hs00233992-m1 |
| | Reverse | |
| hREX-1 | Forward | 5'-GGATCTCCCACCTTTCCAAG-3' |
| | Reverse | 5'-GCAGGTAGCACACCTCCTG-3' |
| hNanog | Forward | 5'-ATGCCTCACACGGAGACTGT-3' |
| | Reverse | 5'-CAGGGCTGTCCTGAATAAGC-3' |

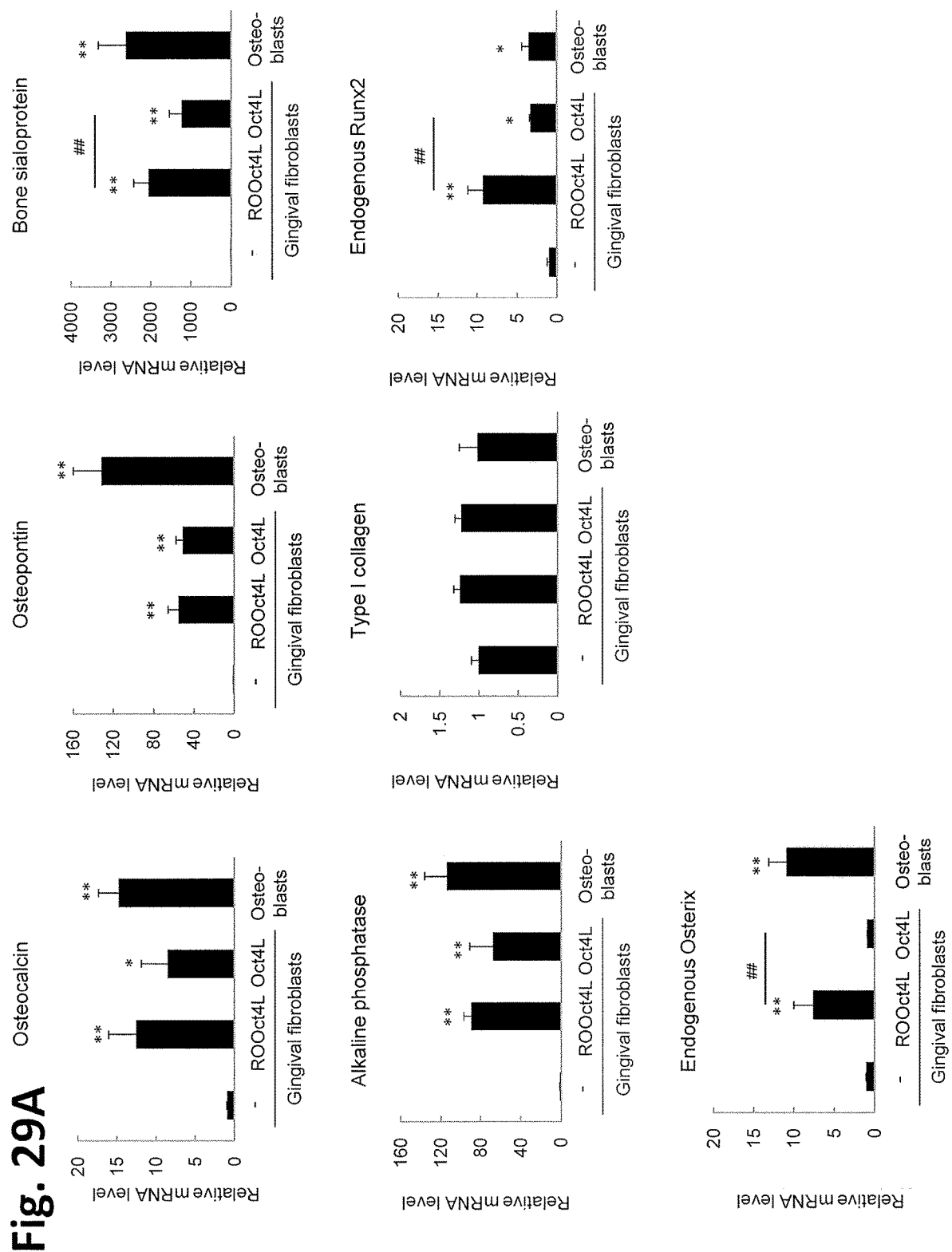

Fig. 29B

| Target | Primer | Description |
|---|---|---|
| hβ-actin | Forward | Applied Bioscience Hs00287164-m1 |
| | Reverse | |
| hOC | Forward | 5'-TGAGAGCCCTCACACTCCTC-3' |
| | Reverse | 5'-ACCTTTGCTGGACTCTGCAC-3' |
| hOPN | Forward | Applied Bioscience Hs00959010-m1 |
| | Reverse | |
| hBSP | Forward | 5'-CAATCTGTGCCACTCACTGC-3' |
| | Reverse | 5'-CAGTCTTCATTTGGTGATTGC-3' |
| hALP | Forward | 5'-CCTGCCTTACTAACTCCTTAGTGC-3' |
| | Reverse | 5'-CGTTGGTGTTGAGCTTCTGA-3' |
| hCOL1A | Forward | 5'-CTGGAGAGGCTGGTACTGCT-3' |
| | Reverse | 5'-AGCACCAAGAAGACCCTGAG-3' |
| endogenous Runx2 | Forward | 5'-CTATGCGTATTCCCG-3' |
| | Reverse | 5'-GGGCTCACGTCGCTCATTT |
| endogenous Osterix | Forward | 5'-CAGCTCTCCATCTGCCTGG-3' |
| | Reverse | 5'-GGGACTGGAGCCATAGTGAACT |

OSTEOBLAST AND METHOD FOR PREPARING SAME

TECHNICAL FIELD

The present invention relates to an osteoblast and a method of preparing the osteoblast, and more specifically, to a method of preparing an osteoblast by direct reprogramming.

SEQUENCE LISTING

A sequence listing in electronic (ASCII text file) format is filed with this application and incorporated herein by reference. The name of the ASCII file is "2016_0085A_Sequence_Listing"; the file was created on Jan. 21, 2016; the size of the file is 8.56 KB.

BACKGROUND ART

Transplantation of osteoblasts to an affected area to repair a bone defect due to a bone tumor, trauma, osteomyelitis, or the like or a bone defect after curettage of a bone tumor or the like can be expected to promote bone formation and to improve functional and morphological prognosis. In actuality, treatment performed by autologous transplantation of bone marrow cells collected from, for example, the cancellous bone of a patient has been carried out, and the effectiveness of the treatment is known. In this case, osteoblasts obtained by differentiation induction from mesenchymal stem cells contained in autologous bone marrow cells are considered to contribute to bone formation and remodeling. Meanwhile, prevalence of osteoporosis has been increasing in step with the aging of the population, and bone fracture of an elderly person may lead to prolonged bed rest. Transplantation of osteoblasts is considered to be capable of promoting healing of bone fracture due to osteoporosis, trauma, or the like, intractable bone fracture, and pseudofracture. In addition, the transplantation of the osteoblasts may also be useful for, for example, rheumatoid arthritis, idiopathic osteonecrosis of the femoral head, arthrosis deformans, lumbar spondylosis deformans, spinal canal stenosis, disc herniation, spondylolysis, spondylolytic spondylolisthesis, scoliosis, cervical spondylotic myelopathy, ossification of posterior longitudinal ligament, spinal cord injury, coxarthrosis, gonarthrosis, slipped capital femoral epiphysis, osteomalacia, bone repair after surgery (such as breast bone repair after cardiac surgery), repair of a defect associated with artificial ankle joint surgery, osteomyelitis, and osteonecrosis.

On the other hand, a periodontal disease may be referred to as the fourth lifestyle-related disease, occurs at a very high prevalence in persons, and causes various systemic diseases. As the periodontal disease progresses, bone resorption of the alveolar bone occurs. Accordingly, when osteoblasts can be supplied to a local bone resorption site with high efficiency, the alveolar bone may be regenerated and treated.

When transplantation of osteoblasts is combined with bone transplantation, artificial bone transplantation, artificial joints, and implants, therapeutic effects may be enhanced.

Bone marrow mesenchymal stem cells, bone marrow cells including bone marrow mesenchymal stem cells, and the like have heretofore been used as such osteoblasts for transplantation. However, collection of the bone marrow has problems. For example, the collection is highly invasive to a patient and a sufficient number of bone marrow cells cannot be supplied in some cases. On the other hand, use of human embryonic stem cells (ES cells) does not require collection of the bone marrow from a patient and may supply a sufficient number of osteoblasts, but may cause a risk of tumorigenesis of residual ES cells after transplantation in addition to ethical issues. In addition, use of iPS cells does not require collection of the bone marrow from a patient and may supply a sufficient number of osteoblasts, but may cause a risk of tumorigenesis of residual iPS cells after transplantation.

In Non Patent Literature 1, there is a disclosure of introduction of a lentivirus vector including Osterix into human ES cells and differentiation induction into osteoblasts in an osteogenic medium.

In Non Patent Literature 2 and Non Patent Literature 3, there are disclosures of preparation of osteoblasts from mouse iPS cells through conversion into MSCs by differentiation induction in an osteogenic medium.

In Non Patent Literature 4, there is a disclosure of preparation of osteoblasts by introducing an adenovirus vector including Runx2 into mouse iPS cells and subjecting the cells to differentiation induction in an osteogenic medium.

As disclosed in Non Patent Literature 1 to Non Patent Literature 4, osteoblasts are prepared from pluripotent stem cells, such as ES cells and iPS cells, by differentiation induction, and hence the methods require long-term culture and have risks of carcinogenesis.

For example, the following reports have been made on the fact that, when a gene group of a tissue-specific transcription factor is introduced into somatic cells, direct differentiation induction into tissue cells can be achieved without conversion into iPS cells (direct reprogramming (direct conversion)):
mouse fibroblast→chondrocyte (SOX9+Klf4+c-Myc genes were introduced),
mouse fibroblast→cardiac muscle cell (GATA4+Mef2c+Tbx5 genes were introduced),
mouse fibroblast→liver cell (Hnf4α+(Foxa1, Foxa2, or Foxa3) genes were introduced),
mouse fibroblast→neural stem cell (for example, Sox2+FoxG1 genes were introduced), and
mouse or human cell→hematopoietic stem cell.
However, there is no report of direct conversion of the somatic cells into the osteoblasts.

CITATION LIST

Non Patent Literature

[NPL 1] Karner E et al. J Cell Physiol. 2009.
[NPL 2] Li F et al. J Cell Biochem. 2010.
[NPL 3] Biloussova G et al. Stem cells. 2011.
[NPL 4] Tashiro K et al. Stem cells. 2009.

SUMMARY OF INVENTION

Technical Problem

An object of the present invention is to provide a method of preparing an osteoblast that is applicable to repair of a bone defect due to various tumors, injuries, operations, etc. and to treatment for bone resorption typified by a periodontal disease, bone fracture, osteoporosis, etc. and has less risks of carcinogenesis.

Solution to Problem

The inventors of the present invention have found that osteoblasts can be obtained directly by introducing specific genes in combination into somatic cells of a mammal (direct reprogramming) without conversion into pluripotent stem cells, such as ES cells and iPS cells.

According to embodiments of the present invention, there are provided the following osteoblast and preparation method therefor.

Item 1. A method of preparing an osteoblast from a somatic cell of a mammal, the method including introducing a reprogramming-related gene or an expression product thereof into the somatic cell, the reprogramming-related gene including at least one kind selected from the group consisting of Oct family, c-Myc (M), L-Myc (L), GLIS family, Klf family, Lin-28, and Sox2.

Item 2. A method of preparing an osteoblast from a somatic cell of a mammal, the method including introducing a bone-related gene or an expression product thereof and a reprogramming-related gene or an expression product thereof into the somatic cell, the bone-related gene including at least one kind selected from the group consisting of Runx2 (R), Osterix (O), and Dlx5 (D), the reprogramming-related gene including at least one kind selected from the group consisting of Oct family, c-Myc (M), L-Myc (L), GLIS family, Klf family, Lin-28, and Sox2.

Item 3. A method according to Item 1 or 2, in which the somatic cell includes a fibroblast or a gingival cell.

Item 4. A method according to any one of Items 1 to 3, in which the reprogramming-related gene or the expression product thereof includes Oct4.

Item 5. A method of preparing an osteoblast according to Item 4, in which the reprogramming-related gene or the expression product thereof to be introduced into the somatic cell includes one of Oct4, Oct4L, Oct4M, Oct4LM, Oct4LGlis1, and Oct4LMGlis1, where M represents "c-Myc", and L represents "L-Myc".

Item 6. A method according to anyone of Items 1 to 3, in which a combination of the bone-related gene or the expression product thereof and the reprogramming-related gene or the expression product thereof to be introduced into the somatic cell includes one combination selected from the group consisting of Oct4, Oct4LMGlis1, ROD Oct4L, RD Oct4L, RO Oct4ML, D Oct4ML, ROD Oct4M, OD Oct4L, O Oct4ML, O Oct4L, O Oct4M, OD Oct4, D Oct4L, Oct4ML, ROD Oct4ML, RD Oct4ML, OD Oct4ML, O Oct4MLGlis1, RD Oct4M, R Oct4L Glis1, R Oct4ML, OD Oct4M, O Oct4L Glis1, ROD Oct4, RO Oct4M, RO Oct4L, RO Oct4, O Oct4 Glis1, RD Oct4, Oct4L Glis1, D Oct4M, D Oct4 Glis1, O Oct4, Oct4L, Oct4M, D Oct4, RO Oct4 K, RO Oct4Sox2, and RO Oct4Lin28, where R represents "Runx2", O represents "Osterix", D represents "Dlx5", M represents "c-Myc", and L represents "L-Myc".

Item 7. A method according to anyone of Items 1 to 3, in which a combination of the bone-related gene or the expression product thereof and the reprogramming-related gene or the expression product thereof to be introduced into the somatic cell includes one combination selected from the group consisting of ROD Oct4L, RD Oct4L, RO Oct4ML, D Oct4ML, ROD Oct4M, OD Oct4L, O Oct4ML, O Oct4L, O Oct4M, OD Oct4, D Oct4L, and Oct4ML, where R represents "Runx2", O represents "Osterix", D represents "Dlx5", M represents "c-Myc", and L represents "L-Myc".

Item 8. A method according to Item 2 or 3, in which a combination of the bone-related gene or the expression product thereof and the reprogramming-related gene or the expression product thereof to be introduced into the somatic cell includes one combination selected from the group consisting of ROD Oct4L, RD Oct4L, RO Oct4ML, and D Oct4ML.

Item 9. An osteoblast, which is derived from a somatic cell of a mammal and includes a reprogramming-related gene or an expression product thereof, the reprogramming-related gene including at least one kind selected from the group consisting of Oct4, c-Myc (M), L-Myc (L), GLIS family, Klf family, Lin-28, and Sox2.

Item 10. An osteoblast, which is derived from a somatic cell of a mammal and includes a bone-related gene or an expression product thereof and a reprogramming-related gene or an expression product thereof, the bone-related gene including at least one kind selected from the group consisting of Runx2 (R), Osterix (O), and Dlx5 (D), the reprogramming-related gene including at least one kind selected from the group consisting of Oct4, c-Myc (M), L-Myc (L), GLIS family, Klf family, Lin-28, and Sox2.

The present invention is directed to a technology for preparing an osteoblast from a somatic cell by introducing a reprogramming-related gene or an expression product thereof, or a bone-related gene or an expression product thereof and a reprogramming-related gene or an expression product thereof. As the bone-related gene out of those, at least one kind may be selected from the group consisting of Runx2 (R), Osterix (O), and Dlx5 (D). The gene desirably includes at least one of Oxterix and Dlx5. In addition, at least one kind selected from the group consisting of the following genes may be selected as the reprogramming-related gene: Oct4 family, c-Myc (M), L-Myc (L), Glis family, Klf family (KLF1, KLF2, KLF3, KLF4, KLF5, KLF6, KLF7, KLF8, KLF9, KLF10, KLF11, KLF12, KLF13, KLF14, KLF15, KLF16, and KLF17), Lin-28, and Sox2. The reprogramming-related gene includes desirably at least one kind of the Oct4 family, more desirably at least one kind of the Oct4 family and L-Myc and/or c-Myc. Of the Oct4 family, Oct4 is desired. Thus, the reprogramming-related gene includes most desirably both of Oct4 and L-Myc and/or c-Myc.

Instead of Oct4, another gene of the Oct family may be used in the same manner as above. In general, Oct4 may be represented as Oct3/4, but is represented as "Oct4" in this description. In this description, "Oct4" is used for description as a representative for the Oct family, but other genes (Oct1A and Oct6) of the Oct family may also be used in the same manner as Oct4.

Oct4 is a factor for reprogramming somatic cells to induce multipotency by gene introduction together with Sox2, Klf4, and c-Myc into the somatic cells (Takahashi K, Yamanaka S. Cell, 126(4): 663-76, 2006; Takahashi K, Tanabe K, Ohnuki M, Narita M, Ichisaka T, Tomoda K, Yamanaka S. Cell. 131(5): 861-72, 2007). It is known that gene introduction of any of GATA3, GATA6, SOX7, PAX1, GATA4, CEBPa, HNF4a, GRB2, and the like instead of Oct4 into somatic cells together with Sox2, Klf4, and c-Myc can reprogram the somatic cells to induce multipotency (Shu et al. Cell 153: 963, 2013). Factors, such as GATA3, GATA6, SOX7, PAX1, GATA4, CEBPa, HNF4a, and GRB2, which are not reprogramming factors and do not belong to the Oct family but can have a function alternative to Oct in reprogramming, may also be used instead of Oct4 in the present invention. That is, in this description, the term "Oct4" is used for description as a representative factor capable of having a function of Oct4 in reprogramming, but factors, such as GATA3, GATA6, SOX7, PAX1, GATA4, CEBPa, HNF4a, and GRB2, which can have a function alternative to Oct in reprogramming, may also be used in the same manner as Oct4.

KLF-4 may also be replaced with any other gene of the Klf family (KLF1, KLF2, KLF3, KLF5, KLF6, KLF7, KLF8, KLF9, KLF10, KLF11, KLF12, KLF13, KLF14, KLF15, KLF16, or KLF17). In this description, the term "KLF-4" is used for description as a representative for the Klf family, but other genes of the Klf family may also be used in the same manner as KLF-4.

As the GLIS family, GLIS1 (GLIS family zinc finger 1) or the like is given.

As genes that can have a function alternative to KLF-4 in reprogramming of somatic cells (induction of iPS cells), there are known not only genes of the KLF family but also, for example, a member of the IRX family (such as IRX6 (iroquois homeobox protein 6)), a member of the PTX family (such as PITX2 (paired-like homeodomain transcription factor 2)), and DMRTB1 (DMRT-like family B with proline-rich C-terminal 1) (WO2010/098419 (Sep. 2, 2010)). In this description, the term "KLF-4" is used for description, but genes that can have a function alternative to KLF-4 in reprogramming of somatic cells (induction of iPS cells) may be used in the same manner as KLF-4. Products of those genes, i.e., mRNAs, may also be used.

Instead of SOX2, another gene of the SOX family may be used in the same manner as SOX2. In this description, the term "SOX2" is used for description as a representative for the SOX family, but another gene of the SOX family may also be used in the same manner as SOX2.

In the present invention, all the genes are referred to as SOX2 for convenience sake.

Instead of one or more of the bone-related gene and the reprogramming-related gene, expression products thereof may be used as alternatives. Further, instead of one or more of the bone-related gene and the reprogramming-related gene, a molecule of a reagent or the like capable of inducing or mimicking a gene may be used as an alternative. As genes that can have a function alternative to Oct4 in induction of iPS cells, there are known, for example, GATA3, GATA6, SOX7, PAX1, GATA4, CEBPa, HNF4a, and GRB2 (Jian Shu et al., Cell 153, 963-975, 2013), and hence such compounds may be used instead of the introduction of the Oct4 gene. As a small-molecule compound that can have a function alternative to Oct4 in reprogramming of neural precursor cells, BIX-01294 is known (Bo Feng et al., Cell Stem. Cell 4: 301, 2009), and hence such compound may be used instead of the introduction of the Oct4 gene. As a compound that can have a function alternative to Klf-4 in induction of iPS cells, kenpaullone (Lyssiotis, C A, et al., Proc Natl Acad Sci USA. 2009 Jun. 2; 106(22): 8912-8917.) is known, and hence such compound may be used instead of the introduction of the Klf-4 gene. In this description, for convenience sake, a gene and an expression product thereof are sometimes collectively referred to as "gene". In such case, the term "introduction of a gene" is replaced by the term "addition of a molecule," "addition of a drug," "addition of a compound," "administration of a molecule," "administration of a drug," "administration of a compound," or the like.

Another gene may further be added to the combinations of genes of the present invention.

The present invention encompasses a method of inducing an osteoblast from a somatic cell. The present invention also encompasses an osteoblast prepared by the method. The present invention also encompasses a cell preparation for treatment including the osteoblast or a transplantation material including the osteoblast.

When this technology is applied to a somatic cell in a body, an osteoblast can be produced directly in the body. The present invention further includes this method and a preparation for direct induction.

Advantageous Effects of Invention

According to the embodiments of the present invention, osteoblasts can be provided from somatic cells by direct reprogramming in a short period of time. The osteoblasts can be induced easily from somatic cells of a person to be transplanted. Accordingly, even when osteoblasts themselves or bone tissues prepared from the cells are transplanted, a problem, such as an immunological rejection response, does not occur. In addition, osteoblasts can be induced directly from somatic cells without conversion into iPS cells or ES cells, and hence a problem due to pluripotent stem cells, such as carcinogenesis, can be avoided.

BRIEF DESCRIPTION OF DRAWINGS

FIG. 3A is a macrograph of a dish. Calcified bone matrix was stained red, which suggested that functional osteoblasts were induced. Refer to FIG. 3H for the numbers of the wells (the number "1" in the table of FIG. 3H represents infection with retrovirus vectors including the respective genes, and the blank represents non-infection with retrovirus vectors including the respective genes).

FIG. 3B is a macrograph of a dish. Calcified bone matrix was stained red, which suggests that functional osteoblasts were induced. Refer to FIG. 3H for the numbers of the wells (the number "1" in the table of FIG. 3H represents infection with retrovirus vectors including the respective genes, and the blank represents non-infection with retrovirus vectors including the respective genes).

FIG. 3C is a result of Alizarin Red S staining. FIG. 3C is a macrograph of a dish. Calcified bone matrix was stained red, which suggests that functional osteoblasts were induced. Refer to FIG. 3H for the numbers of the wells (the number "1" in the table of FIG. 3H represents infection with retrovirus vectors including the respective genes, and the blank represents non-infection with retrovirus vectors including the respective genes).

FIG. 3D is a macrograph of a dish. Calcified bone matrix was stained red, which suggested that functional osteoblasts were induced. Refer to FIG. 3H for the numbers of the wells (the number "1" in the table of FIG. 3H represents infection with retrovirus vectors including the respective genes, and the blank represents non-infection with retrovirus vectors including the respective genes).

FIG. 3E is a macrograph of a dish. Calcified bone matrix was stained red, which suggested that functional osteoblasts were induced. Refer to FIG. 3H for the numbers of the wells (the number "1" in the table of FIG. 3H represents infection with retrovirus vectors including the respective genes, and the blank represents non-infection with retrovirus vectors including the respective genes).

FIG. 3F is a macrograph of a dish. Calcified bone matrix was stained red, which suggested that functional osteoblasts were induced. Refer to FIG. 3H for the numbers of the wells (the number "1" in the table of FIG. 3H represents infection with retrovirus vectors including the respective genes, and the blank represents non-infection with retrovirus vectors including the respective genes).

FIG. 3H is a result of measurement of absorbances (550 nm to 650 nm) of reaction solutions using a microplate reader. The vertical axis of the graph represents absorbances, and the graph shows that, as the absorbance becomes higher, the amount of calcified bone matrix produced becomes larger, i.e., the amount of fibroblasts converted into functional osteoblasts becomes larger.

FIG. 3I is a result of measurement of absorbances (490 nm to 650 nm) of reaction solutions using a microplate reader by the same experiment as that shown in FIG. 3H. The number "1" in the table represents infection with retrovirus vectors including the respective genes, and the blank represents non-infection with retrovirus vectors including the respective genes. For example, the graph shows that the 27th well includes cells that were infected with retrovirus vectors including Osterix, Runx2, Oct4, L-Myc, and Dlx5 genes and not infected with retrovirus vectors including c-Myc, Glis1, and EGFP genes, and produced a large amount of calcified bone matrix.

FIG. 4 is a result of an ALP activity test.

(FIG. 6A) control, (FIG. 6B) RO Oct4M, (FIG. 6C) RO Oct4L: ×100.

(FIG. 7Aa) Control, (FIG. 7B) RO Oct4M, (FIG. 7C) RO Oct4L: ×1, (FIG. 7D) Control, (FIG. 7E) RO Oct4M, (FIG. 7F) RO Oct4L: ×40.

(FIG. 10A) background, (FIG. 10B) RO Oct4L: ×1.

(FIG. 11A) background, (FIG. 11B) control, (FIG. 11C) RO Oct4M, (FIG. 11D) RO Oct4L: ×1.

(FIG. 12A) control, (FIG. 12B) RO Oct4G, (FIG. 12C) RO Oct4L: ×1, (FIG. 12D) control, (FIG. 12E) RO Oct4G, (FIG. 12F) RO Oct4L: ×40.

FIG. 18A: micro-CT (serial tomographic images), FIG. 18B: histological images (serial sections), FIG. 18C: fluorescent immunohistochemistry (anti-human antibody).

FIG. 20 is a result of in vivo bone regeneration at bone defect sites.

FIG. 21 is an image obtained by three-dimensional reconstruction of data of micro-computed tomography (pCT) shown in FIG. 18a.

FIG. 23 is a list of primers used for RT-PCR.

FIG. 24 is a list of primers used for sequencing.

FIG. 25 is a list of primers used for real-time RT-PCR.

FIG. 29A is a result of measurement of mRNA expression levels of genes by real-time RT-PCR.

FIG. 29B is a list of primers used for sequencing.

DESCRIPTION OF EMBODIMENTS

Figure 1:
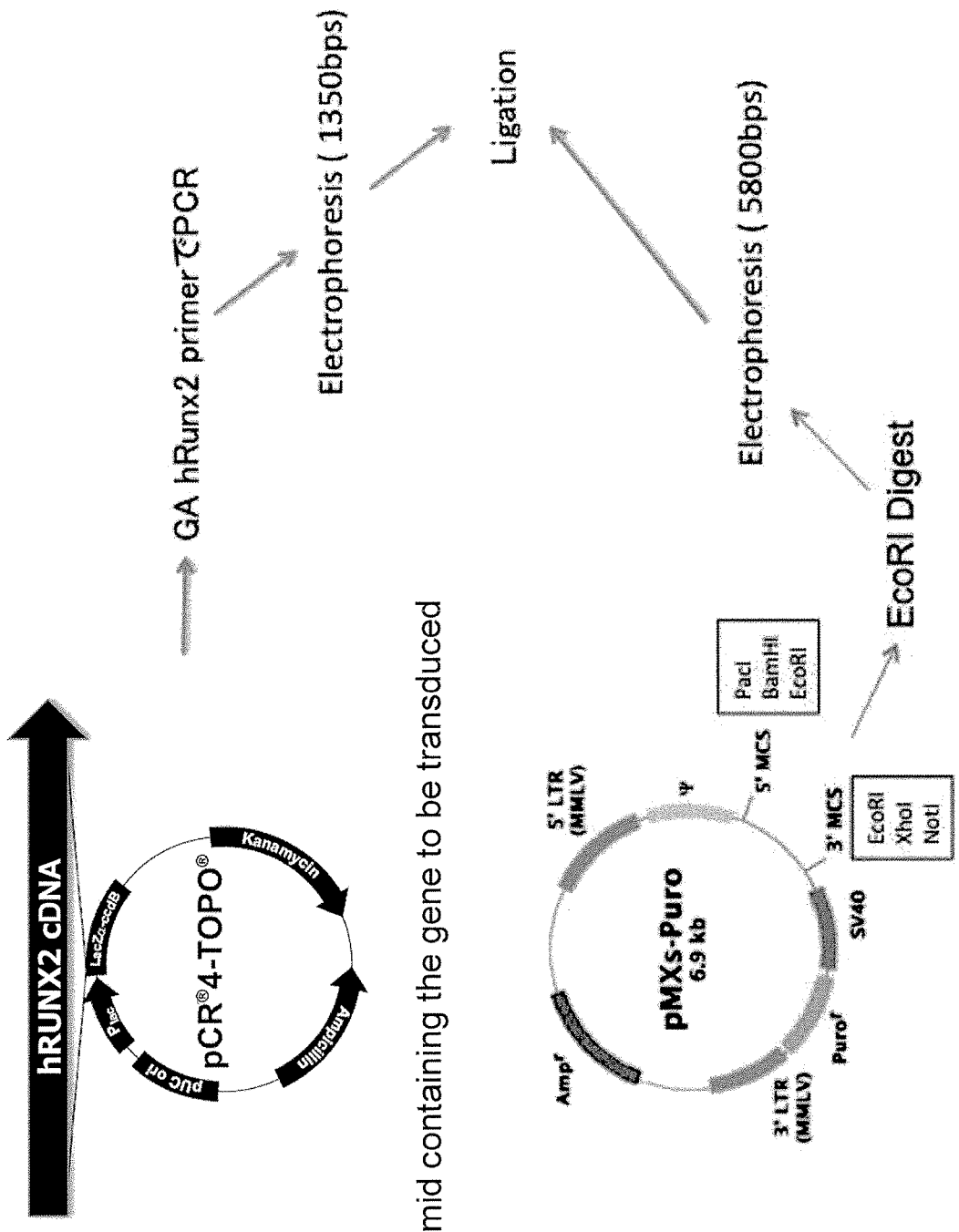
FIG. 1 is an illustration of preparation of pMXs vectors coding for genes of interest.

According to the present invention, preosteoblasts, immature osteoblasts, mature osteoblasts, bone cells, and the like can be prepared. In this description, for convenience sake, all of the cells are referred to as "osteoblasts".

As diseases to be treated with osteoblasts (transplantation material) obtained by the present invention, there are given, for example, bone defects due to bone tumors, trauma, osteomyelitis, and the like, bone defects after curettage of bone tumors and the like, bone fracture, osteoporosis, periodontal disease, alveolar bone resorption, rheumatoid arthritis, idiopathic osteonecrosis of the femoral head, arthrosis deformans, lumbar spondylosis deformans, spinal canal stenosis, disc herniation, spondylolysis, spondylolytic spondylolisthesis, scoliosis, cervical spondylotic myelopathy, ossification of posterior longitudinal ligament, spinal cord injury, coxarthrosis, gonarthrosis, capital femoral epiphysis, osteomalacia, reconstruction at a bone fracture site destroyed by complex fracture, such as lower jaw reconstruction, repair of bone after surgery (repair of breast bone after cardiac surgery), repair of a defect site associated with artificial ankle joint surgery, osteomyelitis, and osteonecrosis. Further, when the osteoblasts are transplanted in combination with transplantation of bone, transplantation of artificial bone, and use of artificial joint, or implant, therapeutic effects may be enhanced. Further, when bone tissues prepared in vitro by culturing osteoblasts using a three-dimensional scaffold or the like so as to have various shapes are transplanted, the above-mentioned diseases can be treated. In addition to the diseases, various diseases involved in loss, lack, or decreased function of osteoblasts are targeted.

In this description, unless otherwise specified, the term "treatment" refers to treatment for a patient suffering from a specific disease or disorder and means that the treatment ameliorates the severity of the disease or disorder, ameliorates one or more symptoms thereof, or delays or reduces the speed of progress of the disease or disorder. In this description, the "treatment" includes "prevention".

The osteoblasts obtained in the present invention may be used not only for treatment of a disease but also for beauty. For example, when the osteoblasts or a bone tissue formed of the osteoblasts are transplanted to a defect site due to an accident surgery, or the like, the cells can produce a bone matrix to repair the defect site and to obscure the defect site by three-dimensional repair. In such case, for convenience sake, treatment for humans is also referred to as treatment in this description. The term "patient" may be replaced by the term "healthy subject" or "human", and the term "disease" may be replaced by the term "beauty".

The present invention can also be used not only for treatment for diseases of humans but also for treatment for diseases of mammals including pets, such as dogs and cats, and livestock, such as cattle, horses, swine, sheep, and chickens. In such case, the term "patient" may be replaced by the term "livestock" or "mammal".

The transplantation material refers to an osteoblast-containing material to be introduced into a living body for repair and reconstruction of a bone tissue. The transplantation material includes a material that partially or completely regenerates a bone tissue in vitro and is transplanted to the same or another individual. The osteoblasts obtained in the present invention can be used for preparation of the transplantation material. The osteoblasts themselves may also be used as the transplantation material. Accordingly, the osteoblasts may be transplanted to a patient as a cell preparation, may be transplanted together with a base (scaffold) formed of an artificial material, such as hydroxyapatite or bioabsorbable ceramic, or may be cultured with a scaffold and then transplanted. In such case, the scaffold may form various three-dimensional shapes depending on the purpose of transplantation.

The somatic cells may be derived from mammals. When the osteoblasts are transplanted to a living body, somatic cells (autologous cells) derived from a test subject who undergoes transplantation are preferably used to reduce risks of infection, rejection responses, and the like. However, instead of the autologous cells, osteoblasts prepared in advance from somatic cells of another person or another animal may be used for, for example, transplantation for sudden bone fracture or the like. Alternatively, osteoblasts may be prepared from somatic cells of another person or another animal prepared in advance, and used for transplantation. That is, an osteoblast bank or an osteoblast precursor cell bank may be prepared in advance and used for transplantation. In such case, in order to reduce risks, such as rejection responses, MHC typing may be carried out in advance. Further, characteristics and tumorigenicity of osteoblasts may be confirmed in advance.

In this description, examples of the mammal include mice, rats, hamsters, humans, dogs, cats, monkeys, rabbits, cattle, horses, and swine, particularly humans.

The present invention can also be used for, for example, various studies and development of technologies using osteoblasts. For example, the present invention is useful for basic studies such as analysis of osteogenesis, bone aging, morphogenesis, mechanisms of remodeling, mechanical stress against the factors, and influences of nutrients, immunity, nerves, and hormones. The present invention is also useful for, for example, analysis of the influence of internal exposure to a radioactive substance, such as strontium-90, on bone and development of a technology for removing strontium-90 from bone.

The use of the present invention allows osteoblasts to be established from humans or animals having various diseases or genetic backgrounds in a simple, rapid, and inexpensive manner. Accordingly, abnormalities in osteoblasts related to the diseases or genetic backgrounds can be analyzed by a biochemical, molecular biological, or immunological technique or the like. This can contribute to studies on clarification of pathogenic mechanisms of diseases and the like or development of diagnostic methods. Development of drugs, toxicity tests of drugs, and the like using such osteoblasts can contribute to the development of novel treatment methods for various diseases.

Examples of the somatic cells as the subject of the method of the present invention (direct reprogramming) include, but not particularly limited to, fibroblasts, keratinocytes, oral mucosal epithelial cells, respiratory mucosal epithelial cells, gastric mucosal epithelial cells, intestinal mucosal epithelial cells, vascular endothelial cells, smooth muscle cells, adipocytes, gingival cells (gingival fibroblasts and gingival epithelial cells), dental pulp cells, periodontal ligament cells, leukocytes, lymphocytes, muscle cells, conjunctival epithelial cells, and osteoclasts, preferably fibroblasts, keratinocytes, oral mucosal epithelial cells, gingival cells, leukocytes, lymphocytes, and osteoclasts.

In the method of the present invention, at least one kind of reprogramming-related gene, or at least one kind of bone-related gene or an expression product thereof and at least one kind of reprogramming-related gene or an expression product thereof are introduced into somatic cells. In this description, as the "expression product," there are given mRNAs or proteins of genes, such as a bone-related gene and a reprogramming-related gene.

The bone-related gene is a gene to be introduced to allow osteoblasts obtained by reprogramming to serve as osteoblasts, and specifically, at least one kind may be selected from the group consisting of Runx2 (hereinafter sometimes abbreviated as "R"), Osterix (hereinafter sometimes abbreviated as "O"), and Dlx5 (hereinafter sometimes abbreviated as "D"). The gene preferably includes at least one kind of Osterix and Dlx5. One kind or two or more kinds of the genes or expression products thereof are preferably introduced into somatic cells, if necessary, in combination with another bone-related gene or an expression product thereof.

The reprogramming-related gene is a gene to be introduced into somatic cells for conversion of the somatic cells into the osteoblasts. Examples thereof include Oct4, Oct1A, Oct6, c-Myc (hereinafter sometimes abbreviated as "M") L-myc (hereinafter sometimes abbreviated as "L"), N-myc, a Klf family (KLF1, KLF2, KLF3, KLF4 (hereinafter sometimes abbreviated as "K"), KLF5, KLF6, KLF7, KLF8, KLF9, KLF10, KLF11, KLF12, KLF13, KLF14, KLF15, KLF16, and KLF17), Lin-28, Sox1, Sox2, Sox3, Sox7, Sox15, Sox17, and Sox18. One kind or two or more kinds of those genes are introduced into the somatic cells. The somatic cells can be induced to osteoblasts just by introducing the reprogramming-related gene can induce. Without wishing to be bound by theory, the inventors of the present invention consider that this is caused by promotion of expression of an intrinsic bone-related gene by introduction of the reprogramming-related gene.

The bone-related genes, such as Runx2, Osterix, and Dlx5, have been known to be involved in differentiation, development, proliferation, survival, and the like of bone cells. However, a technology for directly inducing osteoblasts from somatic cells, such as fibroblasts (without conversion into pluripotent stem cells) is not known. In addition, a combination of the reprogramming-related genes is known to induce iPS cells from somatic cells but is not known to induce osteoblasts. The inventors of the present invention have established a technology for directly inducing osteoblasts from somatic cells, such as fibroblasts, by using one or more bone-related genes and one or more reprogramming-related genes in combination or one or more reprogramming-related genes. Hitherto, this technology has not been known. Further, it is very important that the reprogramming-related gene include Oct4, but a technology for directly inducing osteoblasts using Oct4 has not been known. In addition, a technology for directly inducing osteoblasts using Oct4 and L-Myc has not been known.

Preferred combinations of the bone-related gene and the reprogramming-related gene to be introduced into the somatic cells are as follows: R Oct4ML, O Oct4ML, D Oct4ML, RO Oct4ML, RD Oct4ML, OD Oct4ML, ROD Oct4ML, ROct4L, O Oct4L, D Oct4L, RO Oct4L, RD Oct4L, OD Oct4L, ROD Oct4L, R Oct4M, O Oct4M, D Oct4M, RO Oct4M, RD Oct4M, OD Oct4M, ROD Oct4M, R Oct4, O Oct4, D Oct4, RO Oct4, RD Oct4, OD Oct4, ROD Oct4, R Oct4ML K, O Oct4ML K, D Oct4ML K, RO Oct4ML K, RD Oct4ML K, OD Oct4ML K, ROD Oct4ML K, R Oct4L K, O Oct4L K, D Oct4L K, RO Oct4L K, RD Oct4L K, OD Oct4L K, ROD Oct4L K, R Oct4M K, O Oct4M K, D Oct4M K, RO Oct4M K, RD Oct4M K, OD Oct4M K, ROD Oct4M K, R Oct4 K, O Oct4 K, D Oct4 K, RO Oct4 K, RD Oct4 K, OD Oct4 K, ROD Oct4 K, R Oct4ML Sox2, O Oct4ML Sox2, D Oct4ML Sox2, RO Oct4ML Sox2, RD Oct4ML Sox2, OD Oct4ML Sox2, ROD Oct4ML Sox2, R Oct4L Sox2, O Oct4L Sox2, D Oct4L Sox2, RO Oct4L Sox2, RD Oct4L Sox2, OD Oct4L Sox2, ROD Oct4L Sox2, R Oct4M Sox2, O Oct4M Sox2, D Oct4M Sox2, RO Oct4M Sox2, RD Oct4M Sox2, OD Oct4M Sox2, ROD Oct4M Sox2, R Oct4 Sox2, O Oct4 Sox2, D Oct4 Sox2, RO Oct4 Sox2, RD Oct4 Sox2, OD Oct4 Sox2, ROD Oct4 Sox2, R Oct4ML Lin28, O Oct4ML Lin28, D Oct4ML Lin28, RO Oct4ML Lin28, RD Oct4ML Lin28, OD Oct4ML Lin28, ROD Oct4ML Lin28, R Oct4L Lin28, O Oct4L Lin28, D Oct4L Lin28, RO Oct4L Lin28, RD Oct4L Lin28, OD Oct4L Lin28, ROD Oct4L Lin28, R Oct4M Lin28, O Oct4M Lin28, D Oct4M Lin28, RO Oct4M Lin28, RD Oct4M Lin28, OD Oct4M Lin28, ROD Oct4M Lin28, R Oct4 Lin28, O Oct4 Lin28, D Oct4 Lin28, RO Oct4 Lin28, RD Oct4 Lin28, OD Oct4 Lin28, ROD Oct4 Lin28, R Oct4ML KSox2, O Oct4ML KSox2, D Oct4ML KSox2, RO Oct4ML KSox2, RD Oct4ML KSox2, OD Oct4ML KSox2, ROD Oct4ML KSox2, R Oct4L KSox2, O Oct4L KSox2, D Oct4L KSox2, RO Oct4L KSox2, RD Oct4L KSox2, OD Oct4L KSox2, ROD Oct4L KSox2, R Oct4M KSox2, O Oct4M KSox2, D Oct4M KSox2, RO Oct4M KSox2, RD Oct4M KSox2, OD Oct4M KSox2, ROD Oct4M KSox2, R Oct4 KSox2, O Oct4 KSox2, D Oct4 KSox2, RO Oct4 KSox2, RD Oct4 KSox2, OD Oct4 KSox2, ROD Oct4 KSox2, R Oct4ML KLin28, 0 Oct4ML KLin28, D Oct4ML KLin28, RO Oct4ML KLin28, RD Oct4ML KLin28, OD Oct4ML KLin28, ROD Oct4ML KLin28, R Oct4L KLin28, O Oct4L KLin28, D Oct4L KLin28, RO Oct4L KLin28, RD Oct4L KLin28, OD Oct4L KLin28, ROD Oct4L KLin28, R Oct4M KLin28, O Oct4M KLin28, D Oct4M KLin28, RO Oct4M KLin28, RD Oct4M KLin28, OD Oct4M KLin28, ROD Oct4M KLin28, R Oct4 KLin28, O Oct4 KLin28, D Oct4 KLin28, RO Oct4 KLin28, RD Oct4 KLin28, OD Oct4 KLin28, ROD Oct4 KSox2, R Oct4ML Sox2Lin28, O Oct4ML Sox2Lin28, D Oct4ML Sox2Lin28, RO Oct4ML Sox2Lin28, RD Oct4ML Sox2Lin28, OD Oct4ML Sox2Lin28, ROD Oct4ML Sox2Lin28, R Oct4L Sox2Lin28, O Oct4L Sox2Lin28, D Oct4L Sox2Lin28, RO Oct4L Sox2Lin28, RD Oct4L Sox2Lin28, OD Oct4L Sox2Lin28, ROD Oct4L Sox2Lin28, R Oct4M Sox2Lin28, O Oct4M Sox2Lin28, D Oct4M Sox2Lin28, RO Oct4M Sox2Lin28, RD Oct4M Sox2Lin28, OD Oct4M Sox2Lin28, ROD Oct4M Sox2Lin28, R Oct4 Sox2Lin28, O Oct4 Sox2Lin28, D Oct4 Sox2Lin28, RO Oct4 Sox2Lin28, RD Oct4 Sox2Lin28, OD Oct4 Sox2Lin28, ROD Oct4 Sox2Sox2, R Oct4ML KSox2Lin28, O Oct4ML KSox2Lin28, D Oct4ML KSox2Lin28, RO Oct4ML KSox2Lin28, RD Oct4ML KSox2Lin28, OD Oct4ML KSox2Lin28, ROD Oct4ML KSox2Lin28, R Oct4L KSox2Lin28, O Oct4L KSox2Lin28, D Oct4L KSox2Lin28, RO Oct4L KSox2Lin28, RD Oct4L KSox2Lin28, OD Oct4L KSox2Lin28, ROD Oct4L KSox2Lin28, R Oct4M KSox2Lin28, O Oct4M KSox2Lin28, D Oct4M KSox2Lin28, RO Oct4M KSox2Lin28, RD Oct4M KSox2Lin28, OD Oct4M KSox2Lin28, ROD Oct4M KSox2Lin28, R Oct4 KSox2Lin28, O Oct4 KSox2Lin28, D Oct4 KSox2Lin28, RO Oct4 KSox2Lin28, RD Oct4 KSox2Lin28, OD Oct4 KSox2Lin28, ROD Oct4 KSox2Lin28

R ML, O ML, D ML, RO ML, RD ML, OD ML, ROD ML, R L, O L, D L, RO L, RD L, OD L, ROD L, R M, O M, D M, RO M, RD M, OD M, ROD M, R ML K, O ML K, D ML K, RO ML K, RD ML K, OD ML K, ROD ML K, R L K, O L K, D L K, RO L K, RD L K, OD L K, ROD L K, R M K, O M K, D M K, RO M K, RD M K, OD M K, ROD M K, R K, O K, D K, RO K, RD K, OD K, ROD K, R ML Sox2, O ML Sox2, D ML Sox2, RO ML Sox2, RD ML Sox2, OD ML Sox2, ROD ML Sox2, R L Sox2, O L Sox2, D L Sox2, RO L Sox2, RD L Sox2, OD L Sox2, ROD L Sox2, R M Sox2, O M Sox2, D M Sox2, RO M Sox2, RD

M Sox2, OD M Sox2, ROD M Sox2, R Sox2, O Sox2, D Sox2, RO Sox2, RD Sox2, OD Sox2, ROD Sox2, R ML Lin28, O ML Lin28, D ML Lin28, RO ML Lin28, RD ML Lin28, OD ML Lin28, ROD ML Lin28, R L Lin28, O L Lin28, D L Lin28, RO L Lin28, RD L Lin28, OD L Lin28, ROD L Lin28, R M Lin28, O M Lin28, DM Lin28, ROM Lin28, RD M Lin28, OD M Lin28, ROD M Lin28, R Lin28, O Lin28, D Lin28, RO Lin28, RD Lin28, OD Lin28, ROD Lin28, R ML KSox2, O ML KSox2, D ML KSox2, RO ML KSox2, RD ML KSox2, OD ML KSox2, ROD ML KSox2, R L KSox2, O L KSox2, D L KSox2, RO L KSox2, RD L KSox2, OD L KSox2, ROD L KSox2, R M KSox2, O M KSox2, D M KSox2, RO M KSox2, RD M KSox2, OD M KSox2, ROD M KSox2, R KSox2, O KSox2, D KSox2, RO KSox2, RD KSox2, OD KSox2, ROD KSox2, R ML KLin28, O ML KLin28, D ML KLin28, RO ML KLin28, RD ML KLin28, OD ML KLin28, ROD ML KLin28, R L KLin28, O L KLin28, D L KLin28, RO L KLin28, RD L KLin28, OD L KLin28, ROD L KLin28, RM KLin28, O M KLin28, D M KLin28, RO M KLin28, RD M KLin28, OD M KLin28, ROD M KLin28, R KLin28, O KLin28, D KLin28, RO KLin28, RD KLin28, OD KLin28, ROD KSox2, R ML Sox2Lin28, O ML Sox2Lin28, D ML Sox2Lin28, RO ML Sox2Lin28, RD ML Sox2Lin28, OD ML Sox2Lin28, ROD ML Sox2Lin28, R L Sox2Lin28, O L Sox2Lin28, D L Sox2Lin28, RO L Sox2Lin28, RD L Sox2Lin28, OD L Sox2Lin28, ROD L Sox2Lin28, R M Sox2Lin28, O M Sox2Lin28, D M Sox2Lin28, RO M Sox2Lin28, RD M Sox2Lin28, OD M Sox2Lin28, ROD M Sox2Lin28, R Sox2Lin28, O Sox2Lin28, D Sox2Lin28, RO Sox2Lin28, RD Sox2Lin28, OD Sox2Lin28, ROD Sox2Sox2, R ML KSox2Lin28, O ML KSox2Lin28, D ML KSox2Lin28, RO ML KSox2Lin28, RD ML KSox2Lin28, OD ML KSox2Lin28, ROD ML KSox2Lin28, R L KSox2Lin28, O L KSox2Lin28, D L KSox2Lin28, RO L KSox2Lin28, RD L KSox2Lin28, OD L KSox2Lin28, ROD L KSox2Lin28, R M KSox2Lin28, O M KSox2Lin28, D M KSox2Lin28, RO M KSox2Lin28, RD M KSox2Lin28, OD M KSox2Lin28, ROD M KSox2Lin28, R KSox2Lin28, O KSox2Lin28, D KSox2Lin28, RO KSox2Lin28, RD KSox2Lin28, OD KSox2Lin28, and ROD KSox2Lin28. Of those, the following combinations are desired:

R Oct4ML, O Oct4ML, D Oct4ML, RO Oct4ML, RD Oct4ML, OD Oct4ML, ROD Oct4ML, R Oct4L, O Oct4L, D Oct4L, RO Oct4L, RD Oct4L, OD Oct4L, ROD Oct4L, R Oct4M, O Oct4M, D Oct4M, RO Oct4M, RD Oct4M, OD Oct4M, ROD Oct4M, R Oct4, O Oct4, D Oct4, RO Oct4, RD Oct4, OD Oct4, ROD Oct4, R Oct4ML K, O Oct4ML K, D Oct4ML K, RO Oct4ML K, RD Oct4ML K, OD Oct4ML K, ROD Oct4ML K, R Oct4L K, O Oct4L K, D Oct4L K, RO Oct4L K, RD Oct4L K, OD Oct4L K, ROD Oct4L K, R Oct4M K, O Oct4M K, D Oct4M K, RO Oct4M K, RD Oct4M K, OD Oct4M K, ROD Oct4M K, R Oct4 K, O Oct4 K, D Oct4 K, RO Oct4 K, RD Oct4 K, OD Oct4 K, ROD Oct4 K, R Oct4ML Sox2, O Oct4ML Sox2, D Oct4ML Sox2, RO Oct4ML Sox2, RD Oct4ML Sox2, OD Oct4ML Sox2, ROD Oct4ML Sox2, R Oct4L Sox2, O Oct4L Sox2, D Oct4L Sox2, RO Oct4L Sox2, RD Oct4L Sox2, OD Oct4L Sox2, ROD Oct4L Sox2, R Oct4M Sox2, O Oct4M Sox2, D Oct4M Sox2, RO Oct4M Sox2, RD Oct4M Sox2, OD Oct4M Sox2, ROD Oct4M Sox2, R Oct4 Sox2, O Oct4 Sox2, D Oct4 Sox2, RO Oct4 Sox2, RD Oct4 Sox2, OD Oct4 Sox2, ROD Oct4 Sox2, R Oct4ML Lin28, O Oct4ML Lin28, D Oct4ML Lin28, RO Oct4ML Lin28, OD Oct4ML Lin28, ROD Oct4ML Lin28, R Oct4L Lin28, O Oct4L Lin28, D Oct4L Lin28, RO Oct4L Lin28, RD Oct4L Lin28, OD Oct4L Lin28, ROD Oct4L Lin28, R Oct4M Lin28, O Oct4M Lin28, D Oct4M Lin28, RO Oct4M Lin28, RD Oct4M Lin28, OD Oct4M Lin28, ROD Oct4M Lin28, R Oct4 Lin28, O Oct4 Lin28, D Oct4 Lin28, RO Oct4 Lin28, RD Oct4 Lin28, OD Oct4 Lin28, ROD Oct4 Lin28, R Oct4ML KSox2, O Oct4ML KSox2, D Oct4ML KSox2, RO Oct4ML KSox2, RD Oct4ML KSox2, OD Oct4ML KSox2, ROD Oct4ML KSox2, R Oct4L KSox2, O Oct4L KSox2, D Oct4L KSox2, RO Oct4L KSox2, RD Oct4L KSox2, OD Oct4L KSox2, ROD Oct4L KSox2, R Oct4M KSox2, O Oct4M KSox2, D Oct4M KSox2, RO Oct4M KSox2, RD Oct4M KSox2, OD Oct4M KSox2, ROD Oct4M KSox2, R Oct4 KSox2, O Oct4 KSox2, D Oct4 KSox2, RO Oct4 KSox2, RD Oct4 KSox2, OD Oct4 KSox2, ROD Oct4 KSox2, R Oct4ML KLin28, O Oct4ML KLin28, D Oct4ML KLin28, RO Oct4ML KLin28, RDOct4ML KLin28, OD Oct4ML KLin28, ROD Oct4ML KLin28, R Oct4L KLin28, O Oct4L KLin28, D Oct4L KLin28, RO Oct4L KLin28, RD Oct4L KLin28, OD Oct4L KLin28, ROD Oct4L KLin28, R Oct4M KLin28, O Oct4M KLin28, D Oct4M KLin28, RO Oct4M KLin28, RD Oct4M KLin28, OD Oct4M KLin28, ROD Oct4M KLin28, R Oct4 KLin28, O Oct4 KLin28, D Oct4 KLin28, RO Oct4 KLin28, RD Oct4 KLin28, OD Oct4 KLin28, ROD Oct4 KSox2, R Oct4ML Sox2Lin28, O Oct4ML Sox2Lin28, D Oct4ML Sox2Lin28, RO Oct4ML Sox2Lin28, RD Oct4ML Sox2Lin28, OD Oct4ML Sox2Lin28, ROD Oct4ML Sox2Lin28, R Oct4L Sox2Lin28, O Oct4L Sox2Lin28, D Oct4L Sox2Lin28, RO Oct4L Sox2Lin28, RD Oct4L Sox2Lin28, OD Oct4L Sox2Lin28, ROD Oct4L Sox2Lin28, R Oct4M Sox2Lin28, O Oct4M Sox2Lin28, D Oct4M Sox2Lin28, RO Oct4M Sox2Lin28, RD Oct4M Sox2Lin28, OD Oct4M Sox2Lin28, ROD Oct4M Sox2Lin28, R Oct4 Sox2Lin28, O Oct4 Sox2Lin28, D Oct4 Sox2Lin28, RO Oct4 Sox2Lin28, RD Oct4 Sox2Lin28, OD Oct4 Sox2Lin28, ROD Oct4 Sox2Sox2, R Oct4ML KSox2Lin28, O Oct4ML KSox2Lin28, D Oct4ML KSox2Lin28, RO Oct4ML KSox2Lin28, RD Oct4ML KSox2Lin28, OD Oct4ML KSox2Lin28, ROD Oct4ML KSox2Lin28, R Oct4L KSox2Lin28, O Oct4L KSox2Lin28, D Oct4L KSox2Lin28, RO Oct4L KSox2Lin28, RD Oct4L KSox2Lin28, OD Oct4L KSox2Lin28, ROD Oct4L KSox2Lin28, R Oct4M KSox2Lin28, O Oct4M KSox2Lin28, D Oct4M KSox2Lin28, RO Oct4M KSox2Lin28, RD Oct4M KSox2Lin28, OD Oct4M KSox2Lin28, ROD Oct4M KSox2Lin28, R Oct4 KSox2Lin28, O Oct4 KSox2Lin28, D Oct4 KSox2Lin28, RO Oct4 KSox2Lin28, RD Oct4 KSox2Lin28, OD Oct4 KSox2Lin28, and ROD Oct4 KSox2Lin28. Of those, ROD Oct4L, RD Oct4L, RO Oct4ML, D Oct4ML, ROD Oct4M, OD Oct4L, O Oct4ML, O Oct4L, O Oct4M, OD Oct4, D Oct4L, Oct4ML, ROD Oct4ML, RD Oct4ML, OD Oct4ML, O Oct4MLGlis1, RD Oct4M, R Oct4L Glis1, R Oct4ML, OD Oct4M, O Oct4L Glis1, ROD Oct4, RO Oct4M, RO Oct4L, RO Oct4, O Oct4 Glis1, RD Oct4, Oct4L Glis1, D Oct4M, D Oct4 Glis1, O Oct4, Oct4L, Oct4M, D Oct4, RO Oct4K, RO Oct4Sox2, and RO Oct4Lin28 are particularly desired. Of those, ROD Oct4L, RD Oct4L, RO Oct4ML, D Oct4ML, ROD Oct4M, OD Oct4L, O Oct4ML, O Oct4L, O Oct4M, OD Oct4, and D Oct4L are more desired. Of those, ROD Oct4L, RD Oct4L, RO Oct4ML, and D Oct4ML are more preferred. The desired combinations are particularly effective for direct reprogramming of human cells.

As preferred combinations of reprogramming-related genes to be introduced into somatic cells for induction of osteoblasts with reprogramming-related genes alone, there are given Oct4, Oct4L, Oct4M, Oct4LM, Oct4LGlis1, and Oct4LMGlis1.

All of the genes are highly conserved in vertebrates, and in this description, refer to genes including homologs unless a specific animal name is described. The genes further include genes having functions equivalent to those of wild-type gene products even when the genes include mutations including polymorphisms. The method of the present invention may be carried out in conformity to a known direct reprogramming method except that specific genes are selected, and for example, may be carried out in conformity to a method described in any one of the following literatures:

Literatures: 1 Direct Reprogramming of Fibroblasts into Functional Cardiomyocytes by Defined Factors; Masaki Ieda, Ji-Dong Fu, Paul Delgado-Olguin, VasanthVedantham, Yohei Hayashi, Benoit G. Bruneau, and Deepak Srivastava Cell 142: 375-386, 2010.

2 Direct conversion of fibroblasts to functional neurons by defined factors. Thomas Vierbuchen, Austin Ostermeier, Zhiping P. Pang, YukoKokubu, Thomas C. Sudhof & Marius Wernig. Nature 463: 1035-1041, 2010

3 Induction of human neuronal cells by defined transcription factors. Pang Z P, Yang N, Vierbuchen T, Ostermeier A, Fuentes D R, Yang T Q, Citri A, Sebastiano V, Marro S, Sudhof T C, Wernig M. Nature 476: 220-223, 2011.

4 Generation of hyaline cartilaginous tissue from mouse adult dermal fibroblast culture by defined factors Kunihiko Hiramatsu, Satoru Sasagawa, Hidetatsu Outani, Kanako Nakagawa, Hideki Yoshikawa, and Noriyuki Tsumaki, Journal of Clinical Investigation, 121: 640-657, 2011.

5 Induction of functional hepatocyte-like cells from mouse fibroblasts by defined factors. Pengyu Huang, Zhiying He, Shuyi Ji, Huawang Sun, Dao Xiang, Changcheng Liu, Yiping Hu, XinWang & Lijian Hui., Nature 475:386-389, 2011.

6 Direct conversion of mouse fibroblasts to hepatocyte-like cells by defined factors. Sayaka Sekiya & Atsushi Suzuki. Nature 475:390-393, 2011.

The contents of Literature 1 to Literature 6 are incorporated herein by reference.

Specifically, it is preferred that a gene to be introduced for conversion into osteoblasts (a combination of a bone-related gene and a reprogramming-related gene, or a reprogramming-related gene alone) be incorporated into an expression vector, the expression vector be introduced into target somatic cells, and the gene be expressed in the cells.

As a method of introducing a gene, there may also be used, for example, a method involving infection with a viral vector, such as a retrovirus vector, an adenovirus vector, a lentivirus vector, an adeno-associated virus vector, a herpesvirus vector, or a Sendai virus vector, and in the case of introduction of a gene and an expression product thereof, a method involving transfection with a plasmid vector, an episomal vector, or a gene expression product (mRNA, protein) by a non-viral vector, such as a cationic liposome, a cationic polymer, or electroporation. In addition, mRNA may be introduced. In this description, all the means to be used for gene introduction are collectively referred to as "vector".

Cells in which a gene for treatment is expressed can be selected before use by introducing a gene serving as a drug selective marker (having puromycin resistance, blasticidin S resistance, neomycin resistance, hygromycin resistance, or the like) together with a gene for treatment and selecting the cells with a drug.

When factors to be introduced are an expression product of a bone-related gene and an expression product of a reprogramming-related gene (such as a protein), a peptide called "protein transduction domain (PTD)" may be bonded to a protein obtained as an expression product and added to a medium to introduce the peptide into somatic cells. When some of the bone-related genes are expressed in somatic cells used as a material of osteoblasts, it is not necessary to introduce the protein from the outside. In addition, even when a reprogramming factor or a gene of a reprogramming factor is not introduced, osteoblasts can be induced with a small molecule used as an alternative. Examples thereof include methods described in "Generation of induced pluripotent stem cells using recombinant proteins." Zhou H, Wu S, Joo J Y, Zhu S, Han D W, Lin T, Trauger S, Bien G, Yao S, Zhu Y, Siuzdak G, Scholer H R, Duan L, Ding S. Cell Stem Cell. 2009 May 8; 4(5):381-4. or "Generation of human induced pluripotent stem cells by direct delivery of reprogramming proteins." Kim D, Kim C H, Moon J I, Chung Y G, Chang M Y, Han B S, Ko S, Yang E, Cha K Y, Lanza R, Kim K S. Cell Stem Cell. 2009 Jun. 5; 4(6):472-6.

A differentiation-inducing medium for differentiation of osteoblasts is not particularly limited, and for example, the following osteoinductive medium may be used.

Osteoinductive medium=a medium obtained by adding 50 µg/ml ascorbic acid, 10 mM β-glycerophosphate, and 100 nM dexamethasone (all of the concentrations are final concentrations) to a normal medium.

The existence of osteoblasts prepared can be confirmed by ALP staining, measurement of osteocalcin mRNA or osteopontin mRNA by real-time PCR, staining with Alizarin Red S (production of calcified bone matrix), von Kossa staining, or the like.

In the present invention, genes may be introduced with a plasmid or with a virus vector, for example, a retrovirus vector. The virus vector is preferably used from the viewpoints of efficiency of introduction and maintenance of stability of the gene introduced, while the plasmid is preferably used to reduce a risk of carcinogenesis.

A gene introduced into somatic cells may be transcribed with an LTR promoter or may be expressed with another promoter in a vector. For example, there may be used constitutive expression promoters, such as CMV promoter, EF-1α promoter, and CAG promoter, or desired inductive promoters. In addition, a chimeric promoter obtained by replacing part of LTR by another promoter may be used.

EXAMPLES

Examples are shown below. However, the present invention is not limited to only these Examples.

Figure 26A:
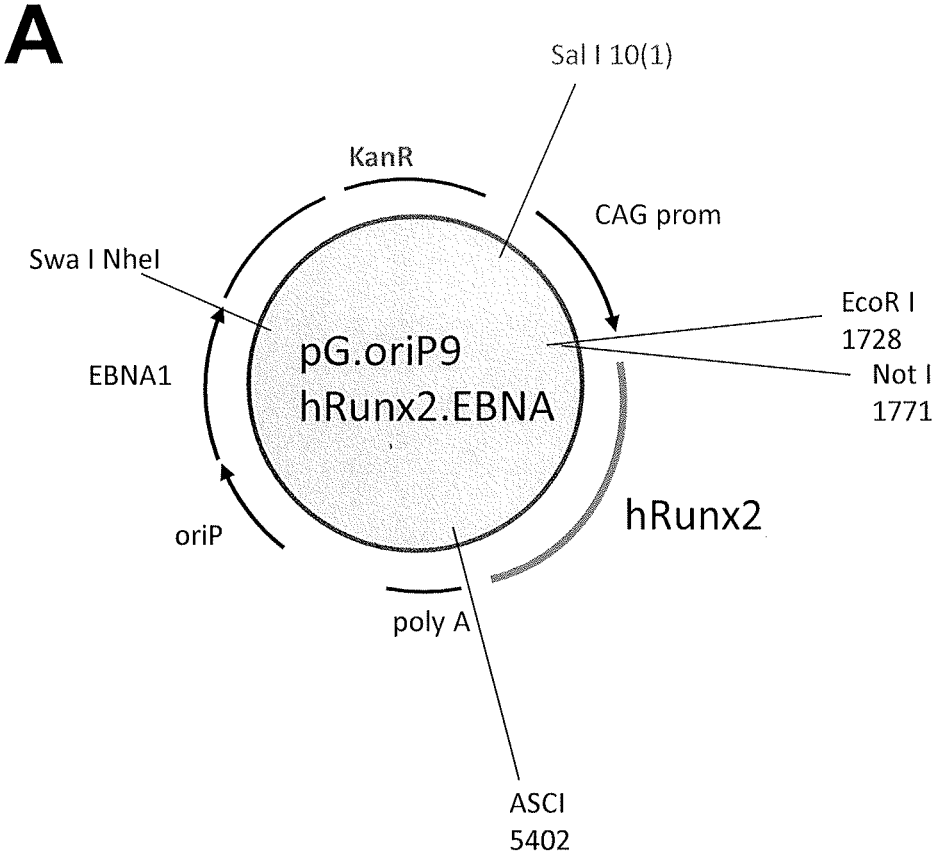
FIGS. 26A-26B are illustrations of direct reprogramming into osteoblasts with an episomal vector.

It should be noted that FIG. 3 to FIG. 11, FIG. 14 to FIG. 16, FIG. 18 to FIG. 22, FIG. 26, FIG. 28 to FIG. 32, FIG. 34, and FIG. 37 and FIG. 38 are results of experiments using a normal human gingival fibroblast strain, Gin-1. FIG. 12 and FIG. 13, FIG. 17, FIG. 33, FIG. 35 and FIG. 36, and FIG. 39 to FIG. 42 are results of experiments using aHDFs (normal human dermal fibroblasts). FIG. 27 are results of experiments using mouse fetal fibroblasts.

Example 1

(1) Preparation of pMXs Vectors Coding for Genes of Interest (FIG. 1)

Genes of interest (Runx2 and the like) were amplified from a plasmid including the genes of interest by PCR using primers for coding regions (base sequences of the primers are shown in FIG. 23). In addition, pMXs puro vector was cleaved with EcoRI. The resultant fragments were separated by electrophoresis, and then genes and the back bone of the vector were extracted from the electrophoresis gel. Both of them were ligated using GeneArtsystem to prepare pMXs vectors coding for genes of interest. The base sequences of those vectors were confirmed using the primers shown in FIG. 24.

Figure 2:
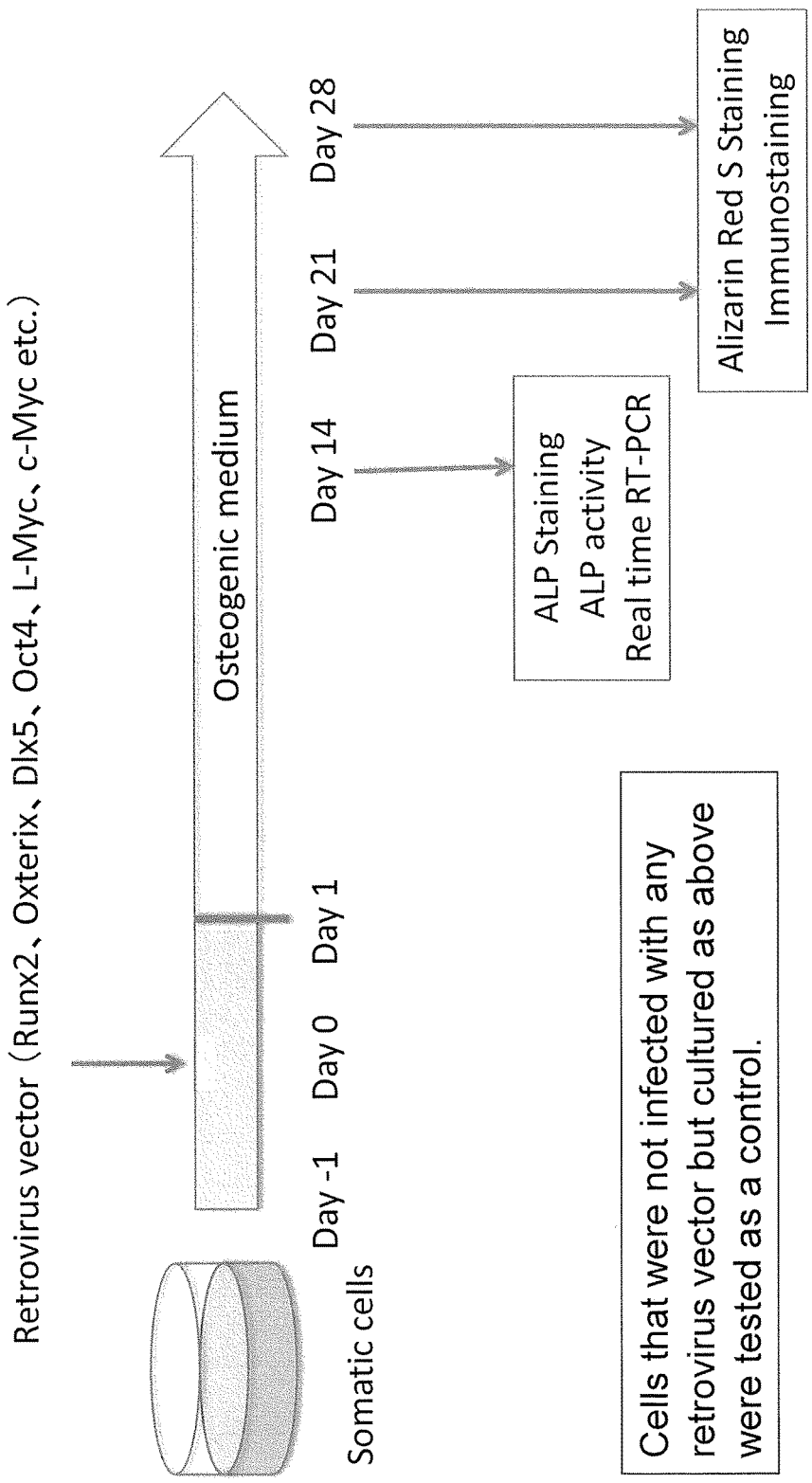
FIG. 2 is an illustration of the outline of an experiment.

(2) Outline of Experiment (FIG. 2)

$3 \times 10^6$ Plat GP cells were inoculated into a 10-cm dish coated with keratin and cultured in 1% NEAA 10% FBS DMEM (normal medium) containing 100 U/ml penicillin and 100 µg/ml streptomycin. 24 Hours later, the pMXs vectors including various genes were introduced into Plat GP serving as packaging cells together with pCMV VSV vector at a ratio of 1:3 in various combinations using X-tremeGENE 9 by a lipofection method (a solution obtained by blending 5 µg of a gene to be introduced, 2.5 µg of pCMV.VSV, 500 µl of Opti-MEM, and 22.5 µl of X-tremeGENE 9 was added to a 10-cm dish supplemented with 10 ml of a medium). 24 Hours later, the medium was exchanged for an antibiotic-free normal medium. On the same day, a normal human gingival fibroblast strain, Gin-1, and a normal human dermal fibroblast strain, aHDF, were inoculated at $2 \times 10^4$ cells/ml to $2 \times 10^5$ cells/ml into culture dishes or culture plates (for example, 12-well plates or 24-well plates for immunostaining; 12-well plates for ALP activity or PCR; 6-well plates for ALP staining; or 24-well plates, 6-well plates, 35-mm dishes, or 60-mm dishes for Alizarin Red S staining), and the day was defined as day −1 of culture. One day later (day 0 of culture), the culture supernatant of Plat GP was passed through a syringe filter having a pore diameter of 0.45 µm, and the filtrate was blended with polybrene (final concentration: 4 µg/ml) (virus solution). Immediately after removal of the culture supernatants of Gin-1 and aHDF by aspiration, the virus solution was added thereto (500 µl for 24-well plates, 1 ml for 12-well plates, 1.5 ml for 6-well plates and 35-mm dishes, 2.5 ml for 60-mm dishes), and the cells were cultured for 24 hours (infection). As a control group, cells not subjected to infection with the virus were also prepared. One day later (day 1 of culture), the culture supernatants were removed by aspiration, and then an osteoinductive medium (prepared by adding 50 µg/ml ascorbic acid, 10 mM β-glycerophosphate, and 100 nM dexamethasone (all of the concentrations are final concentrations) to the normal medium) was added thereto, followed by culture. After that, the culture medium was exchanged every 2 days or 3 days. The cells were subjected to ALP staining, an ALP activity test, and real-time RT-PCR 14 days after the introduction of the genes, to immunostaining 20 days after the introduction of the genes, to Alizarin Red S staining 20 days or 28 days after the introduction of the genes, and to von Kossa staining 28 days after the introduction of the genes. Cells cultured in the same manner without infection with the retrovirus vectors were used as a control.

(3) Alizarin Red S Staining (FIG. 3)

Figure 3A:
FIG. 3A is a result of Alizarin Red S staining.
Figure 3B:
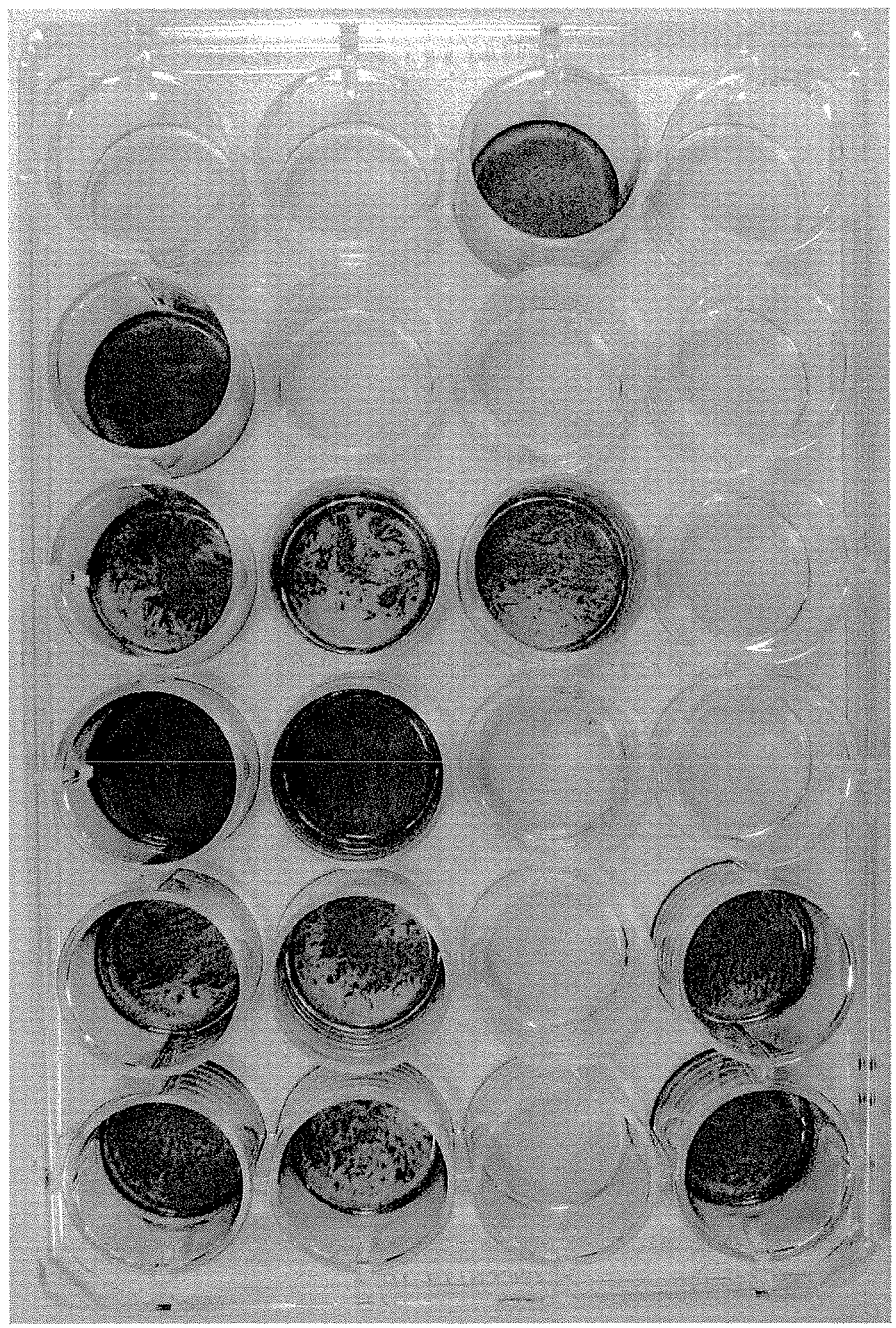
FIG. 3B is a result of Alizarin Red S staining.
Figure 3D:
FIG. 3D is a result of Alizarin Red S staining.
Figure 3E:
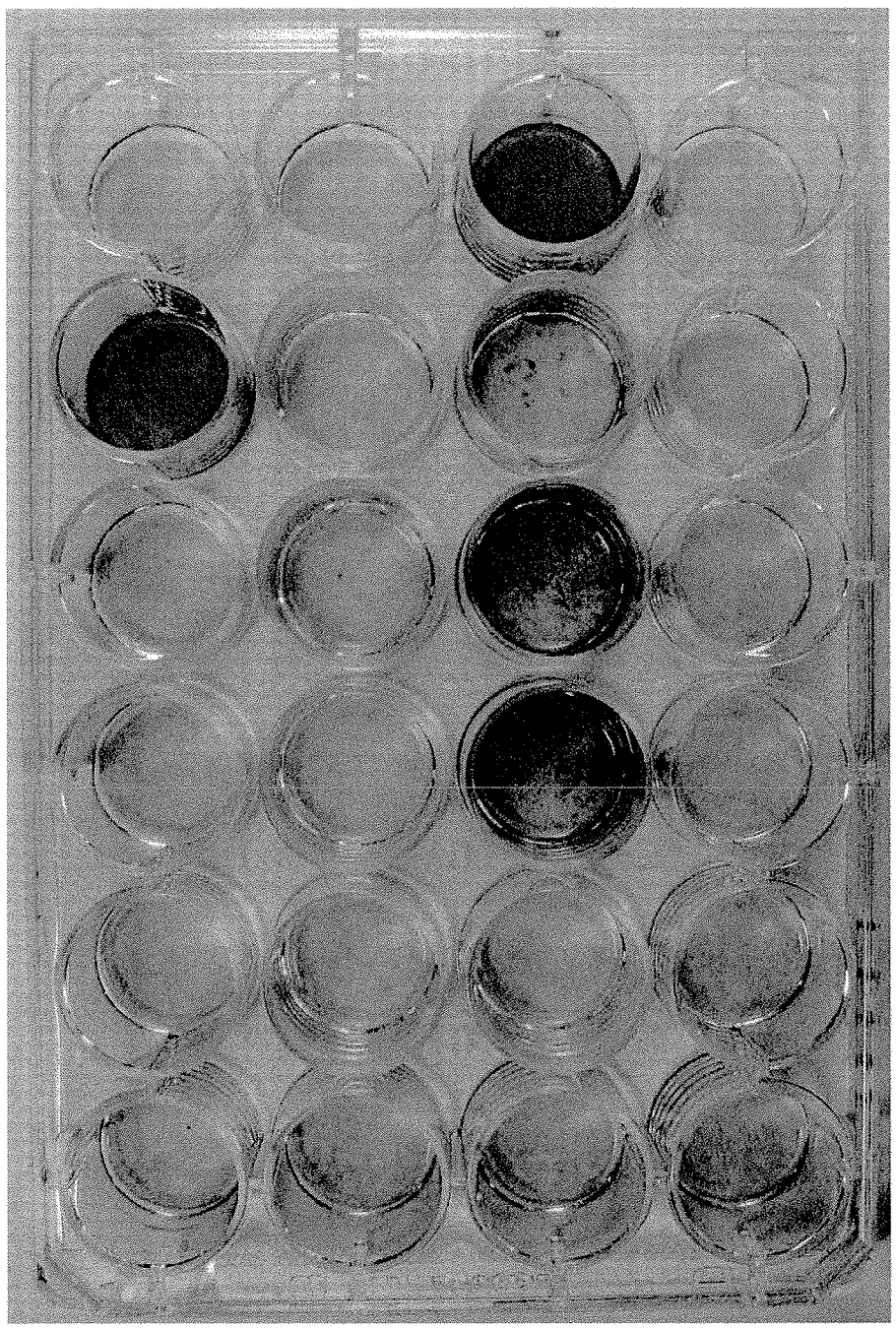
FIG. 3E is a result of Alizarin Red S staining.
Figure 3F:
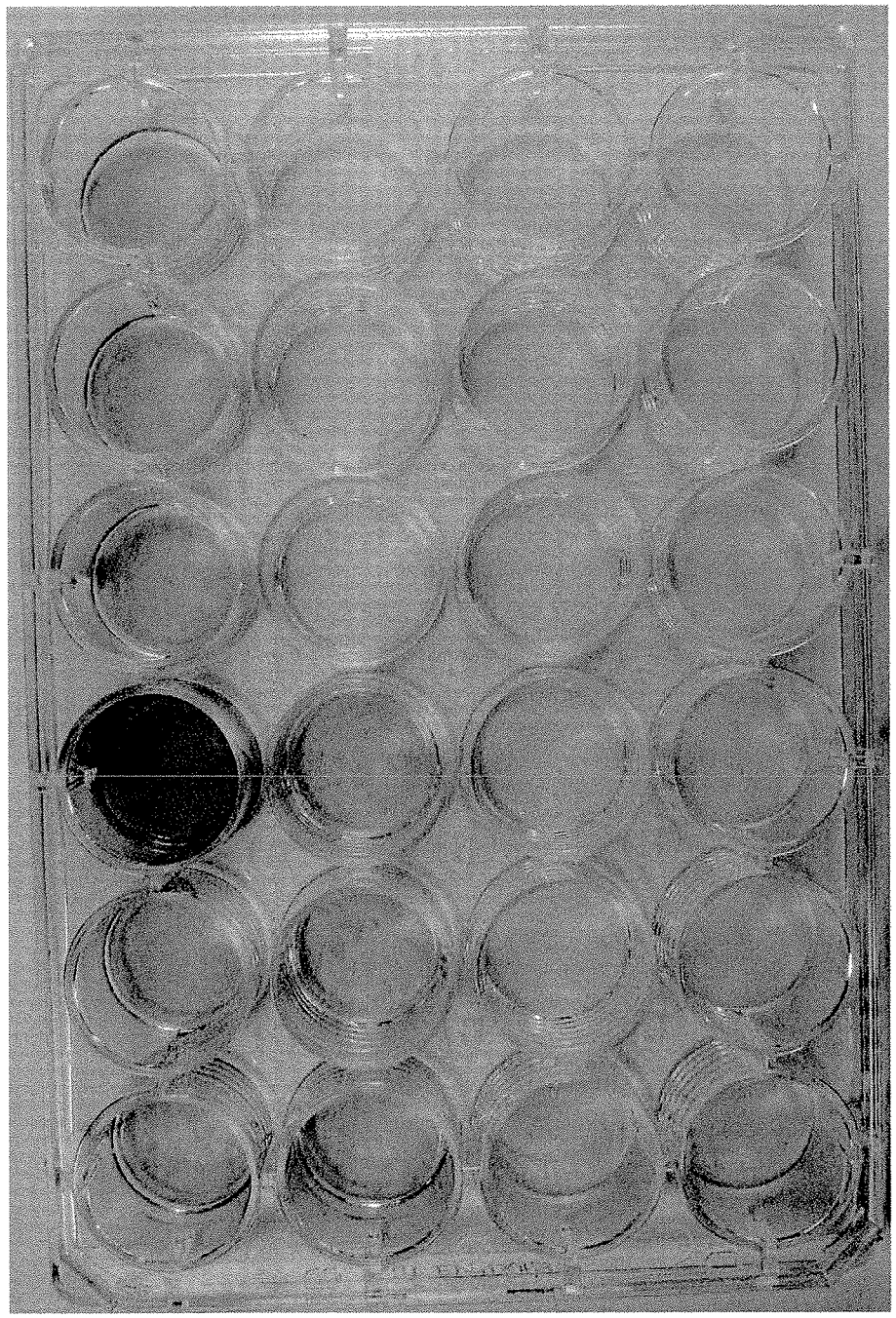
FIG. 3F is a result of Alizarin Red S staining.
Figure 3G:
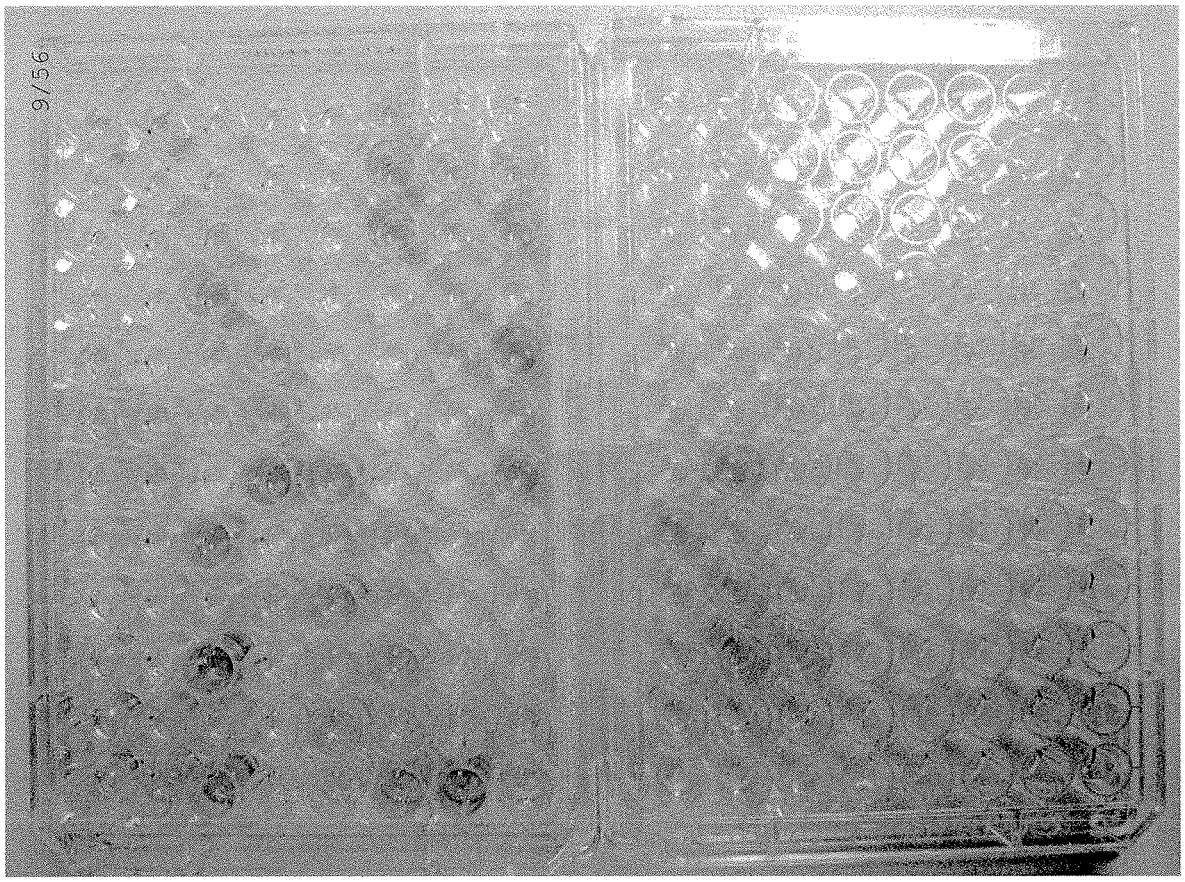
FIG. 3G is a macrograph of a 96-well plate (refer to FIG. 3H for the numbers of the wells).

A normal human gingival fibroblast strain, Gin-1, was cultured in a 24-well plate and subjected to an experiment as illustrated in FIG. 2. 28 Days after the introduction of the genes, the culture medium was removed by aspiration from the culture dish, and the cells were washed twice with PBS and fixed with 95% ethanol. The cells were washed with sterile distilled water, and then an Alizarin Red S staining solution was added thereto, followed by still standing at room temperature for 15 minutes. FIG. 3A to FIG. 3F are macrography of the dish. Calcified bone matrix was stained red, indicating that functional osteoblasts were induced. Refer to FIG. 3H and FIG. 3I for the numbers of the wells (the number "1" in the tables of FIG. 3H and FIG. 3I means that the cells were infected with the retrovirus vectors including the genes, and the blank means that the cells were not infected with the retrovirus vectors including the genes). For example, cells in the 27th well in FIG. 3B (the third well from the left in the first row) were infected with the retrovirus vectors including the Osterix, Runx2, Oct4, L-Myc, and Dlx5 genes and produced a large amount of calcified bone matrix as shown in FIG. 3H. Further, the Alizarin Red S staining solution was removed from all the wells, and the cells were washed with sterile distilled water. After that, 10% Triton X was added thereto, and the resultant was allowed to react at room temperature for 1 hour. The solution was collected from each well and put into a 96-well plate. A macrograph of the plate is shown in FIG. 3G (refer to FIG. 3H for the numbers of the wells). The results of measurement of absorbances (550 nm to 650 nm, FIG. 3H; 490 nm to 650 nm, FIG. 3I) of the reaction solutions using a microplate reader are shown in graphs in FIG. 3H and FIG. 3I. The vertical axis in the graph represents absorbances. The graphs show that, as the absorbance becomes higher, the amount of calcified bone matrix produced becomes larger, i.e., the amount of fibroblasts converted into functional osteoblasts becomes larger. For example, the graphs show that the cells in the 27th well, which were infected with the retrovirus vectors including the Osterix, Runx2, Oct4, L-Myc, and Dlx5 genes, produced calcified bone matrix in the largest amount.

(4) ALP Activity Test (FIG. 4)

A normal human gingival fibroblast strain, Gin-1, was cultured in a 12-well plate and subjected to an experiment as illustrated in FIG. 2. 14 Days after the introduction of the genes, the culture medium was removed by aspiration from the cell culture dish, and the cells were washed twice with physiological saline. The cells were lysed with physiological saline containing 1% NP-40, and the resultant was centrifuged at 12,000 rpm for 5 minutes. The supernatant was collected and allowed to react with ALP buffer containing p-nitrophenol phosphate, and the resultant was subjected to measurement using an absorption spectrometer at 405 nm. Simultaneously, a total protein amount was measured and expressed as an amount corrected by ALP activity per total protein mass. The results are shown in FIG. 4.

In the cells obtained by introducing ROOct4, ROOct4M, ROOct4L, ROOct4G, and the like, significantly high ALP activities were detected compared to the control. Of all the groups, in the cells obtained by introducing ROOct4L, the highest ALP activity was detected.

Figure 5:
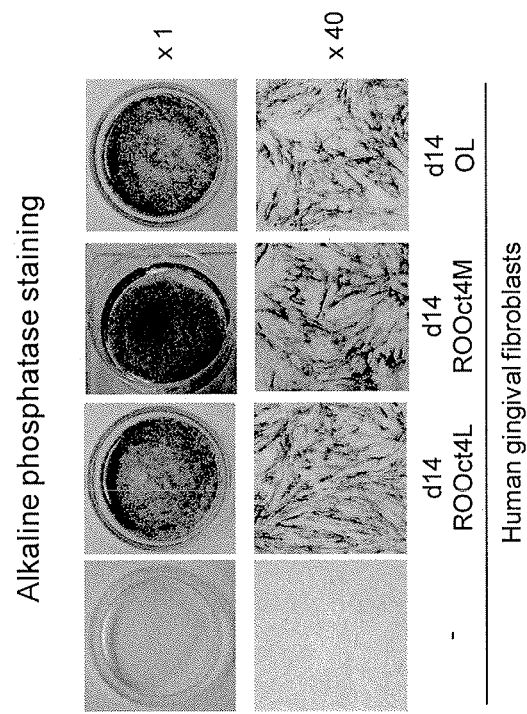
FIG. 5 is an ALP stained image.

(5) ALP Stained Image (FIG. 5)

A normal human gingival fibroblast strain, Gin-1, was cultured in a 6-well plate, and the cells were and subjected to an experiment as illustrated in FIG. 2. 14 Days after the introduction of the genes, the culture medium was removed by aspiration from the wells, and the cells were washed twice with physiological saline and fixed with a fixative for 5 minutes. The cells were washed twice with sterile distilled water. An ALP staining solution was added thereto, and the cells were left to stand still under a light shielding condition at room temperature for 1 hour. The cells were washed twice with sterile distilled water and then observed with the naked eye and under an inverted phase-contrast microscope. The results are shown in FIG. 5.

Some of the cells obtained by introducing ROOct4M, ROOct4L, or Oct4L became positive for ALP. In particular, in the cells obtained by introducing ROOct4L, the ALP staining-positive cells were observed over the whole of the bottom of the well.

Figure 6A:
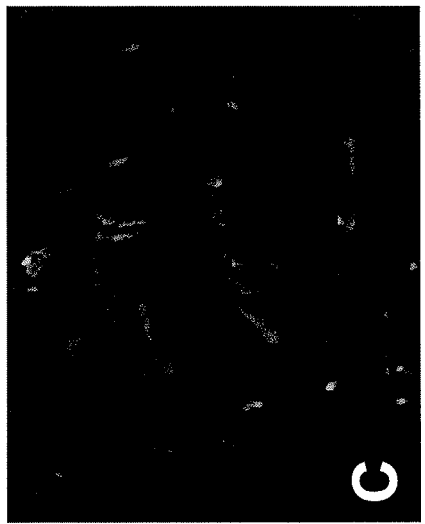
FIGS. 6A-6C are results of immunostaining.
Figure 6B:
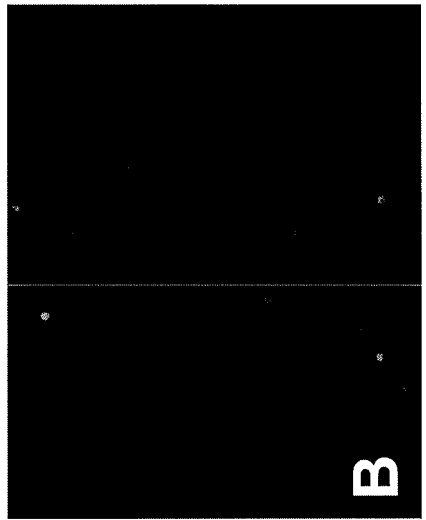
Figure 6C:

(6) Immunostaining (FIG. 6)

A normal human gingival fibroblast strain, Gin-1, was cultured in a 24-well plate and subjected to an experiment as illustrated in FIG. 2. 21 Days after the introduction of the genes, the culture medium was removed by aspiration from the culture dish, and the cells were washed twice with PBS and fixed with 4% paraformaldehyde for 30 minutes. The cells were washed three times and then blocked at room temperature for 1 hour. The cells were allowed to react with a primary antibody (anti-h Osteocalcin) at 4° C. for 24 hours, washed three times, and then allowed to react with a secondary antibody labeled with FITC at room temperature for 1 hour. The cells were washed three times and then observed under a fluorescence microscope. The results are shown in FIG. 6.
(a) Control, (b) ROOct4M, (c) ROOct4L: ×100

In the cells obtained by introducing ROOct4M and ROOct4L, expression of osteocalcin was observed. In the cells obtained by introducing ROOct4L, a larger number of osteocalcin-positive cells were observed.

Figures 7A, 7B, 7C, 7D, 7E, 7F:
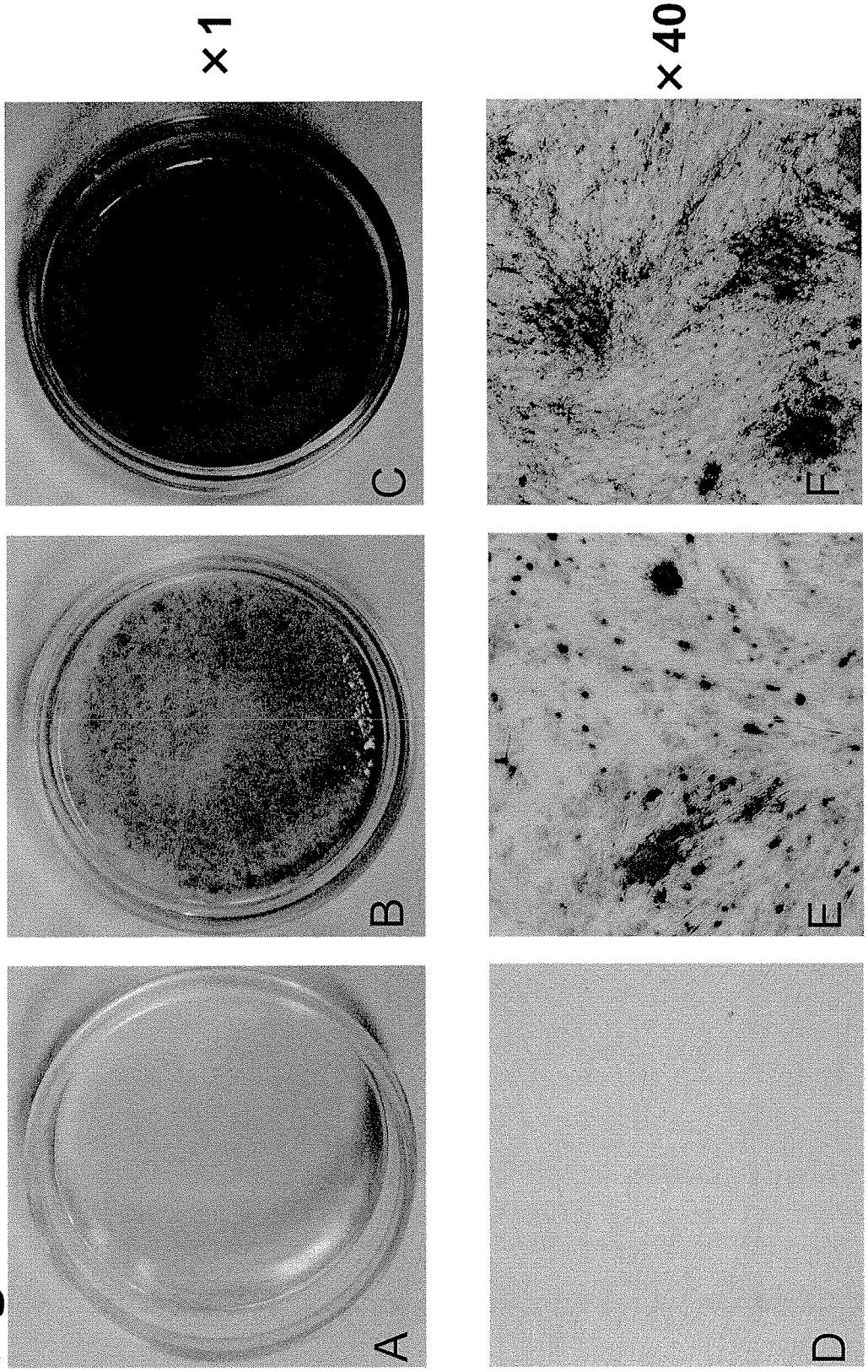
FIGS. 7A-7F are results of Alizarin Red S staining.

(7) Alizarin Red S Staining (FIG. 7)

A normal human gingival fibroblast strain, Gin-1, was cultured in a 35-mm dish and subjected to an experiment as illustrated in FIG. 2. 28 Days after the introduction of the genes, the culture medium was removed by aspiration from the culture dish, and the cells were washed twice with PBS and fixed with 95% ethanol. The cells were washed with sterile distilled water, and then an Alizarin Red S staining solution was added thereto, followed by still standing at room temperature for 15 minutes. The cells were washed with sterile distilled water and then observed with the naked eye and under an inverted phase-contrast microscope. The results are shown in FIG. 7.
(a) Control, (b) ROOct4M, (c) ROOct4L: ×1
(d) Control, (e) ROOct4M, (f) ROOct4L: ×40

In the dish of the cells obtained by introducing ROOct4M or ROOct4L, deposition of calcified matrix was observed. In particular, in the dish of the cells obtained by introducing ROOct4L, deposition of a large amount of calcified bone matrix was observed over the whole of the bottom of the culture dish.

Figure 8:
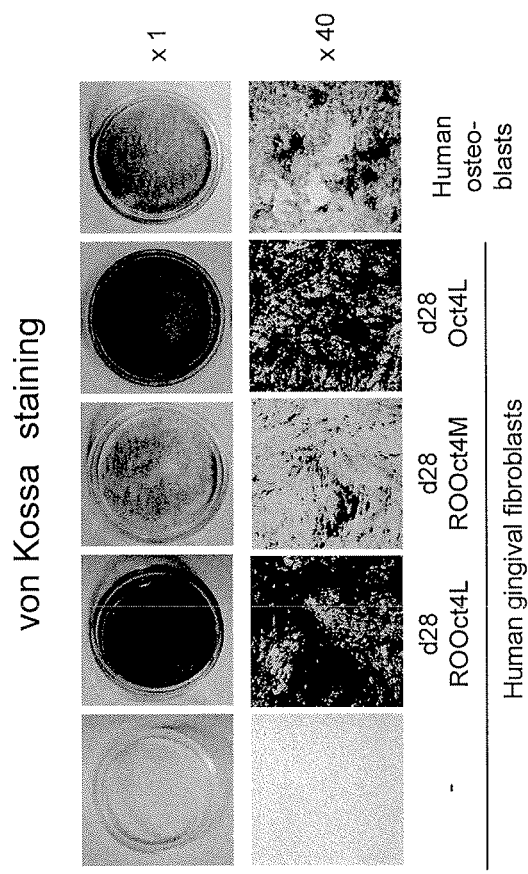
FIG. 8 is a result of von Kossa staining.

(8) Von Kossa Staining (FIG. 8)

A normal human gingival fibroblast strain, Gin-1, was cultured in a 35-mm dish and subjected to an experiment as illustrated in FIG. 2. 28 Days after the introduction of the genes, the culture medium was removed by aspiration from the culture dish, and the cells were washed twice with PBS and fixed with 10% formalin. The cells were washed with sterile distilled water, and then a 5% silver nitrate solution was added thereto, followed by still standing under UV light for 30 minutes. After that, the cells were washed with sterile distilled water and allowed to react with a 5% thiosulfate solution for 2 minutes. The cells were washed with sterile distilled water and then observed with the naked eye and under an inverted phase-contrast microscope. The results are shown in FIG. 8.

In the cells obtained by introducing ROOct4M, scattered deposition of calcium phosphate was observed. In the cells obtained by introducing ROOct4L and Oct4L, dense deposition of calcium phosphate was observed over the whole of the bottom of the culture dish.

Figure 9:
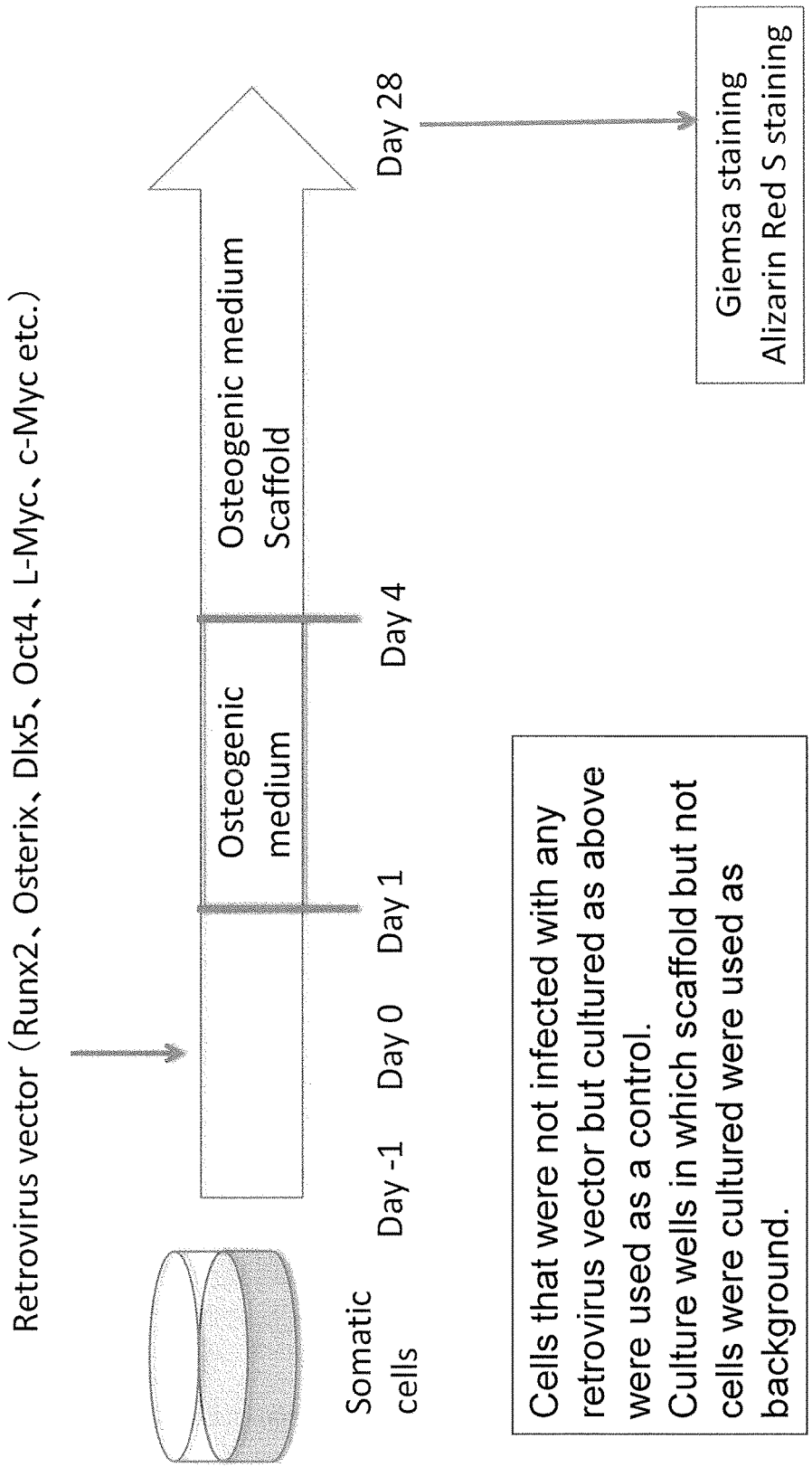
FIG. 9 is an illustration of the outline of a three-dimensional culture experiment.

(9) Outline of Three-Dimensional Experimental Culture Method (FIG. 9)

As illustrated in FIG. 9, somatic cells were inoculated into a culture dish or a culture plate on day −1, genes were introduced on day 0, and the medium was exchanged for a bone differentiation-inducing medium on day 1. Details of the inoculation of the cells on day −1, the introduction of the genes on day 0, and the exchange of the medium on day 1 are the same as those illustrated in FIG. 2. On day 4, the cells were peeled off from the dish, and $5 \times 10^5$ cells were inoculated into a scaffold (3D insert-PCL) and subjected to three-dimensional culture. On day 28, the cells were subjected to Giemsa staining or Alizarin Red S staining. Cells cultured in the same manner without infection with retrovirus vectors were used as a control. In addition, a sample cultured in the same manner without addition of the cells using the scaffold alone was used as a background.

Figure 10A:
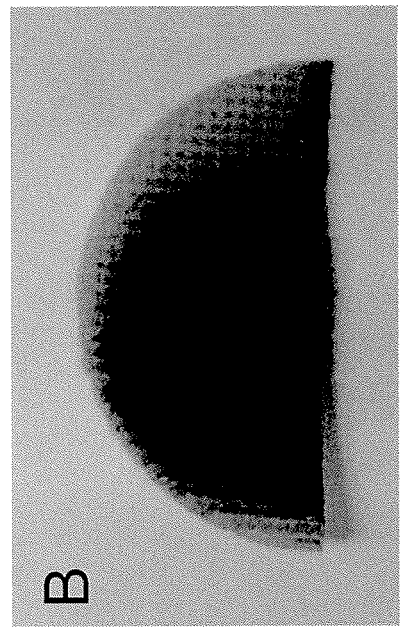
FIGS. 10A-10B are results of Giemsa staining of three-dimensional culture.
Figure 10B:
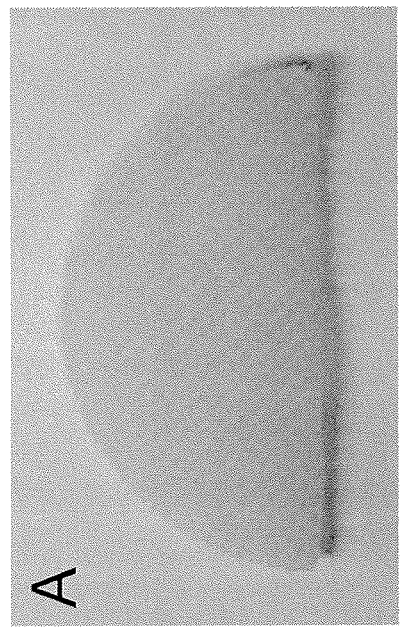

(10) Giemsa Staining in Three-Dimensional Culture (FIG. 10)

A normal human gingival fibroblast strain, Gin-1, was cultured in a 60-mm dish and subjected to an experiment as illustrated in FIG. 9. 28 Days after the introduction of the genes, the culture medium was aspirated from the culture dish, and the cells were washed twice with PBS and fixed with methanol together with the scaffold. The cells were washed with sterile distilled water, and then a Giemsa staining solution was added thereto, followed by still standing at room temperature for 15 minutes. The cells were washed with sterile distilled water and then observed with the naked eye. The results are shown in FIG. 10.
(a) Background, (b) ROOct4L: ×1

The photographs suggest that the induced cells achieved engraftment and proliferation in the scaffold.

Figures 11A, 11B, 11C, 11D:
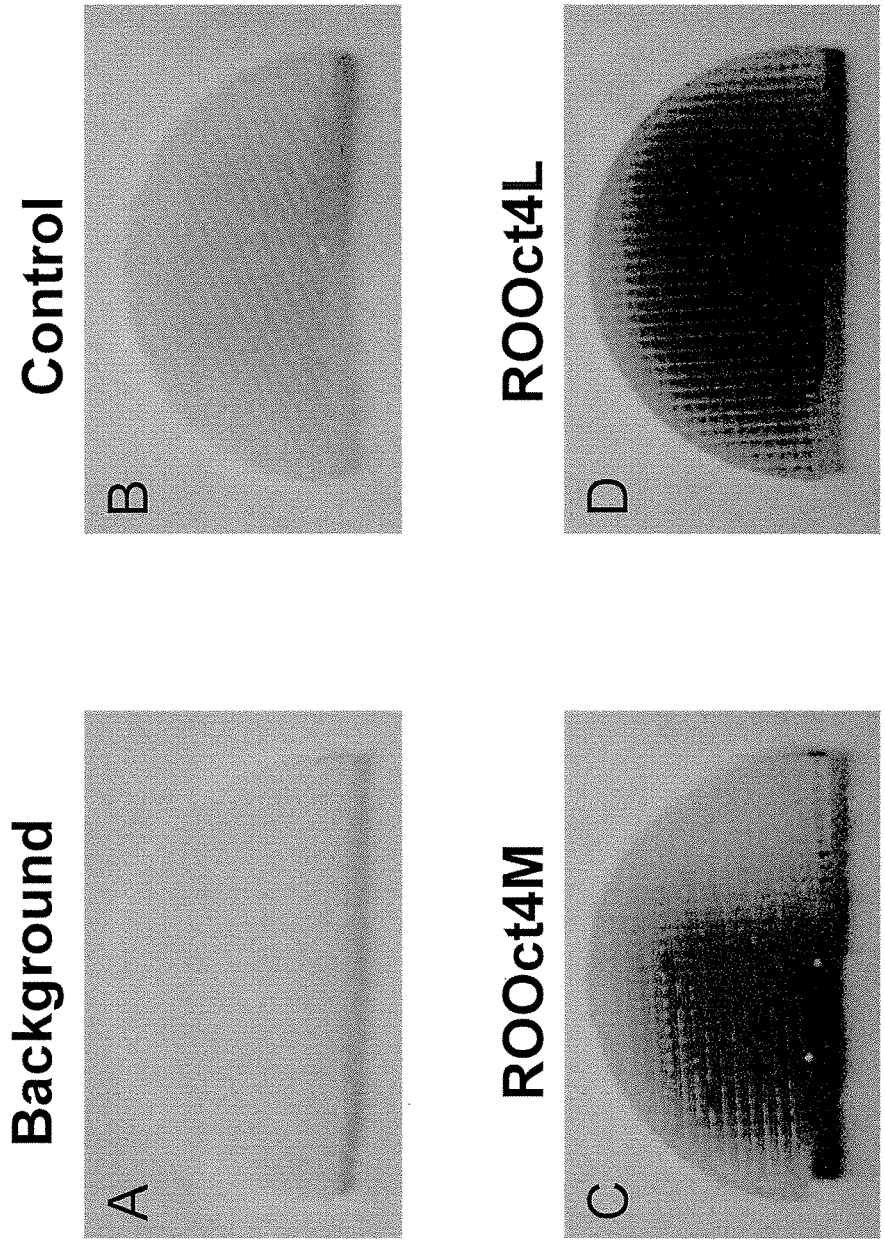
FIGS. 11A-11D are results of Alizarin Red S staining of three-dimensional culture.
Figure 12A:
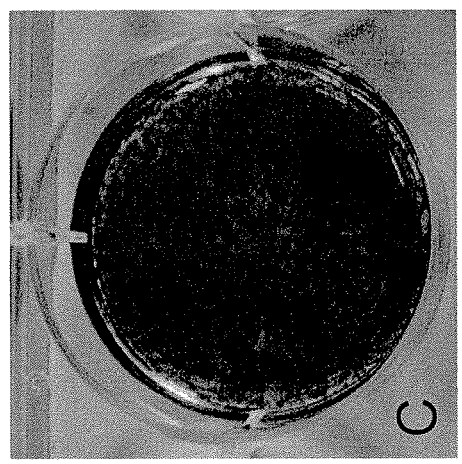
FIGS. 12A-12F are ALP stained images (aHDF).
Figure 12B:
Figure 12C:
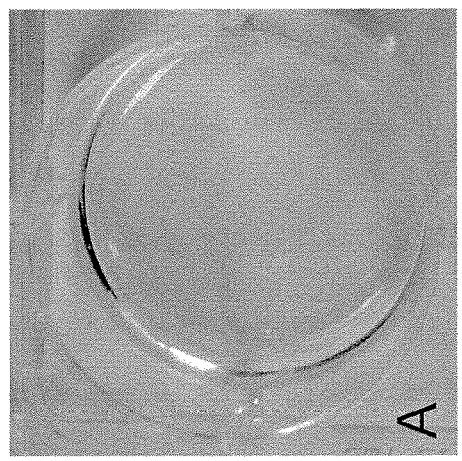
Figure 12D:
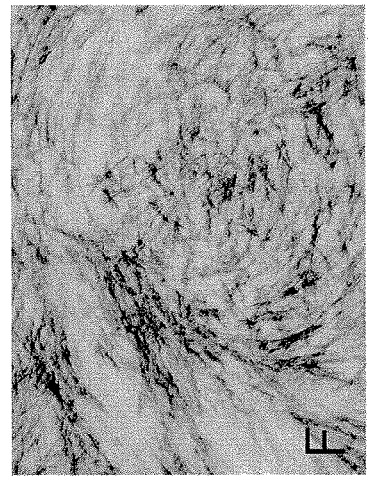
Figure 12E:
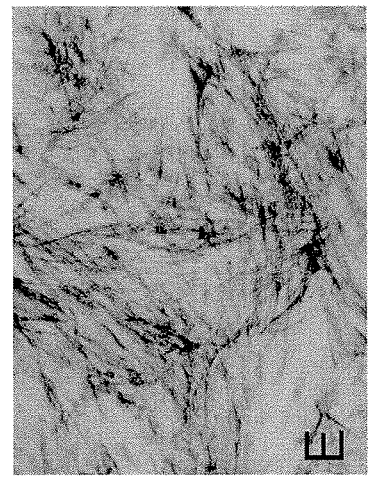
Figure 12F:
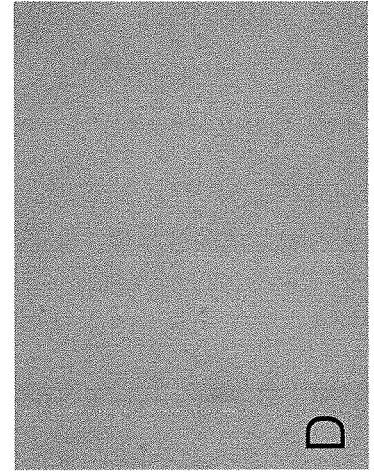

(11) Alizarin Red S Staining in Three-Dimensional Culture (FIG. 11)

A normal human gingival fibroblast strain, Gin-1, was cultured in a 60-mm dish and subjected to an experiment as illustrated in FIG. 9. 28 Days after the introduction of the genes, the culture medium was aspirated from the culture dish, and the cells were washed twice with PBS and fixed with 95% ethanol together with the scaffold. The cells were washed with sterile distilled water, and then an Alizarin Red S staining solution was added thereto, followed by still standing at room temperature for 15 minutes. The cells were washed with sterile distilled water and then observed with the naked eye. The results are shown in FIG. 11.
(a) Background, (b) control, (c) ROOct4M, (d) ROOct4L: ×1

The photographs suggest that the induced cells exhibited an ability to produce calcified bone matrix on the scaffold.

In addition, calcified bone matrix was markedly produced in the cells obtained by introducing ROOct4L.

(12) ALP Stained Image (FIG. 12)

A normal human dermal fibroblast strain, aHDF, was cultured in a 6-well plate, and the cells were and subjected to an experiment as illustrated in FIG. 2. 14 Days after the introduction of the genes, the culture medium was removed by aspiration from the wells, and the cells were washed twice with physiological saline and fixed with a fixative for 5 minutes. The cells were washed twice with sterile distilled water, an ALP staining solution was added thereto, and the cells were left to stand still under a light shielding condition at room temperature for 1 hour. The cells were washed twice with sterile distilled water and then observed with the naked eye and under an inverted phase-contrast microscope. The results are shown in FIG. 12.
(a) control, (b) ROOct4 M, (c) ROOct4L: ×1
(d) control, (e) ROOct4 M, (f) ROOct4L: ×40

Some of the cells obtained by introducing ROOct4M or ROOct4L became positive for ALP staining. In particular, the cells obtained by introducing ROOct4L included many ALP staining positive cells over the whole of the bottom of the well.

Figure 13A:
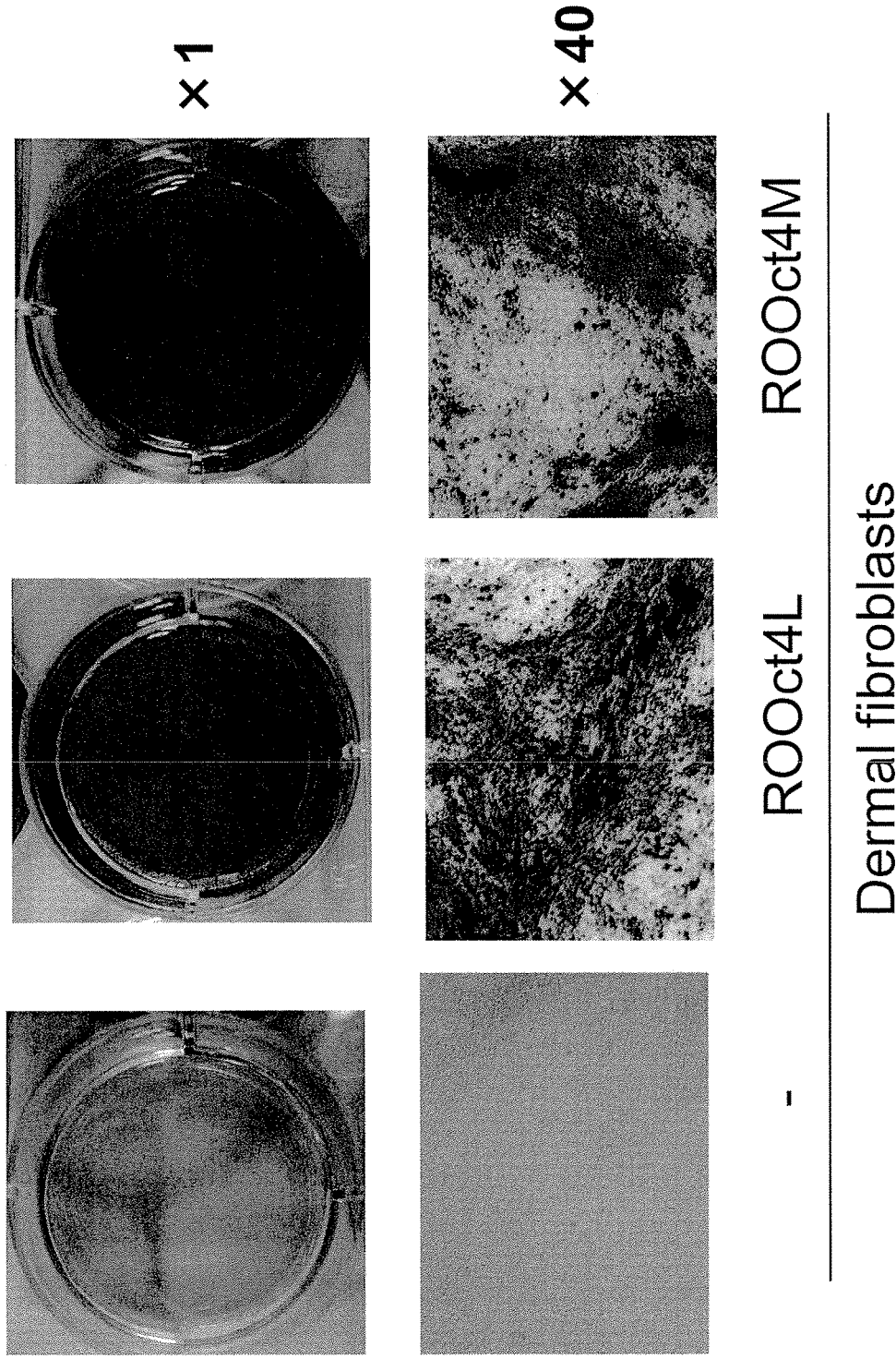
FIG. 13A is a result of Alizarin Red S staining (aHDF).
Figure 13B:
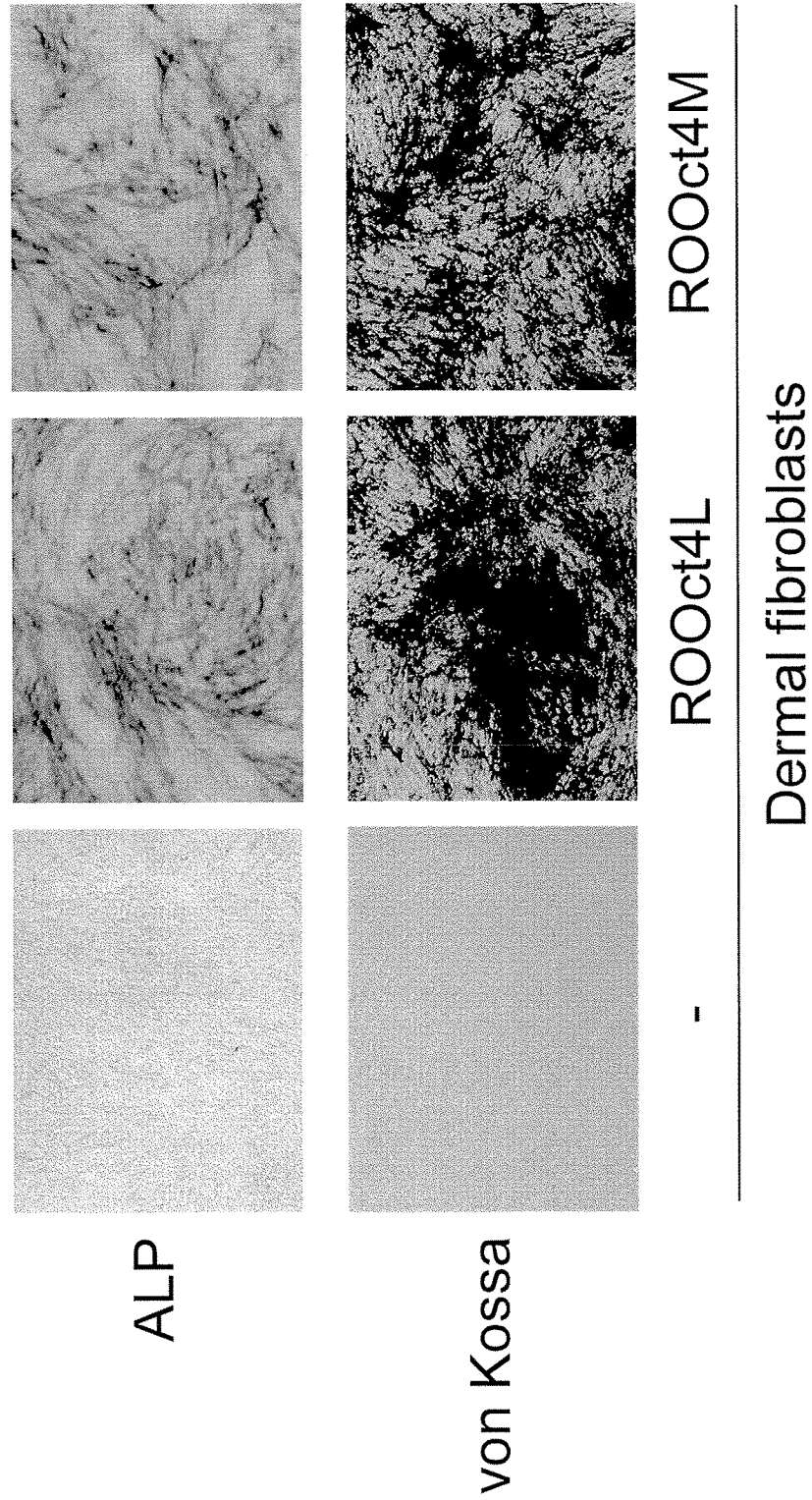
FIG. 13B includes an ALP stained image and a von Kossa stained image.

(13) Alizarin Red S Staining (FIG. 13a and FIG. 13b)

(a) A normal human dermal fibroblast strain, aHDF, was cultured in a 6-well plate and subjected to an experiment as illustrated in FIG. 2. 28 Days after the introduction of the genes, the culture medium was removed by aspiration from the wells, and the cells were washed twice with PBS and fixed with 95% ethanol. The cells were washed with sterile distilled water, and then the Alizarin Red S staining solution was added thereto, followed by still standing at room temperature for 15 minutes. The cells were washed with sterile distilled water and then observed with the naked eye and under an inverted phase-contrast microscope. The results are shown in FIG. 13a.
(Left) control, (Center) ROOct4 M, (Right) ROOct4L: ×1

In the wells of the cells obtained by introducing ROOct4M or ROOct4L, deposition of calcified matrix was observed. In particular, in the cells obtained by introducing ROOct4L, deposition of a large amount of calcified bone matrix was observed over the whole of the bottom of the well.

(b) Inverted phase-contrast microscope images of the cells subjected to the same experiment as that in the item (a) and to ALP staining 14 days after the introduction of the genes (upper) or von Kossa staining 28 days after the introduction of the genes (lower) are shown in FIG. 13b. The magnification was 40 times.

Figure 14:
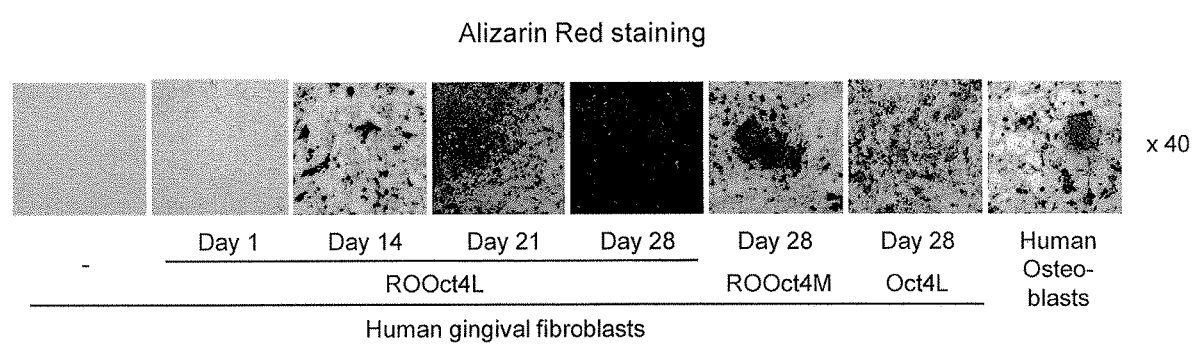
FIG. 14 is a result of Alizarin Red S staining.
Figure 15A:
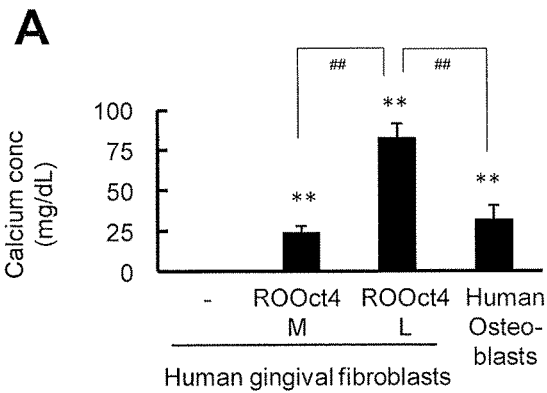
FIGS. 15A-15F are graphs for showing properties of human osteoblasts induced by direct reprogramming.
Figure 15B:
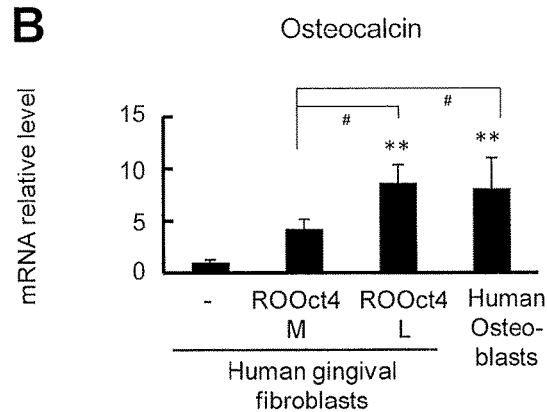
Figure 15C:
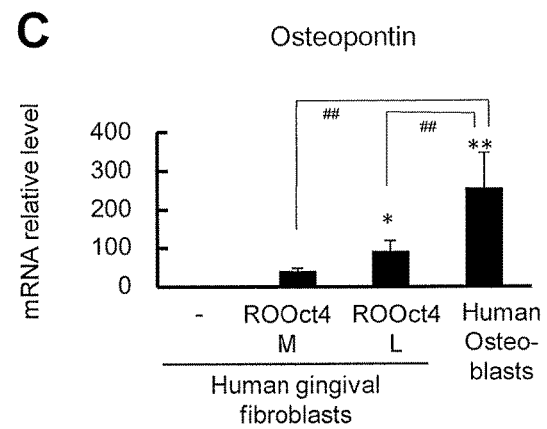
Figure 15D:
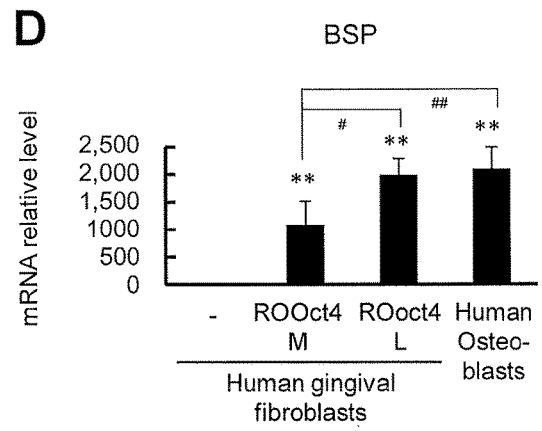
Figure 15E:
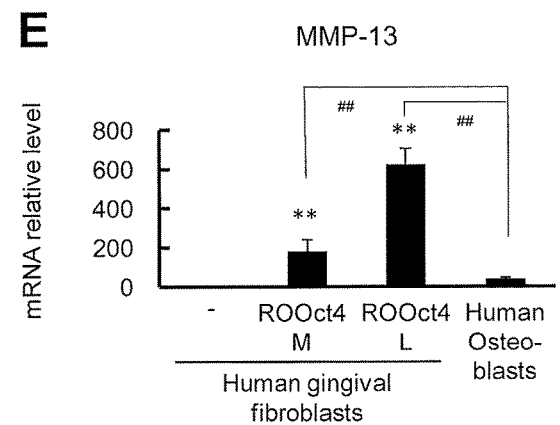
Figure 15F:
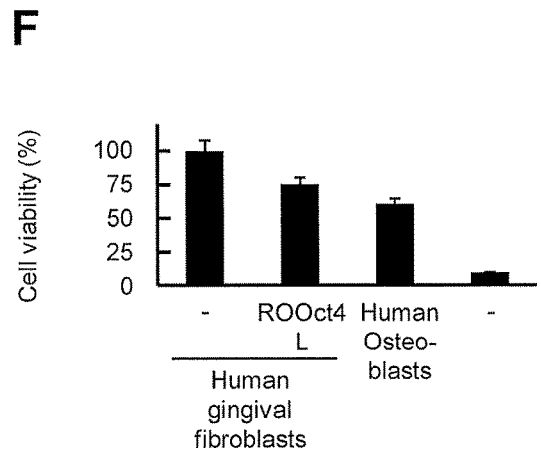
Figure 16A:
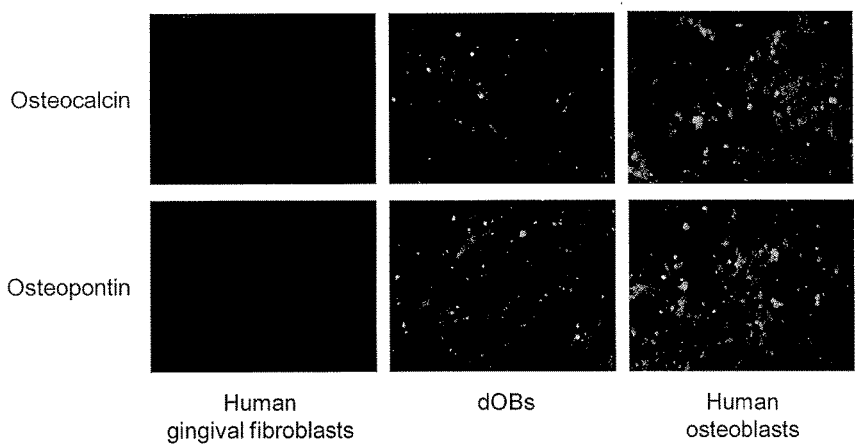
FIGS. 16A-16E are results of analysis for human osteoblasts induced by direct reprogramming.
Figure 16B:
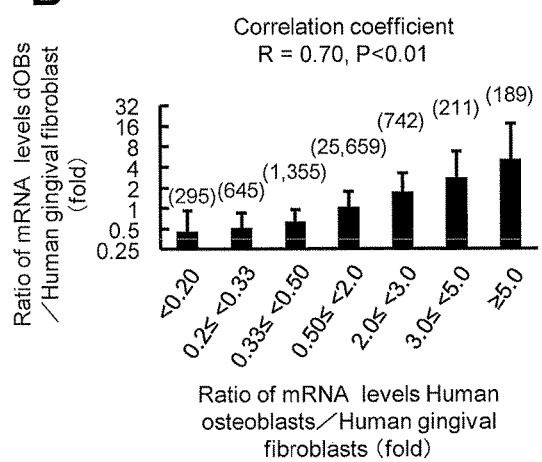
Figure 16C:
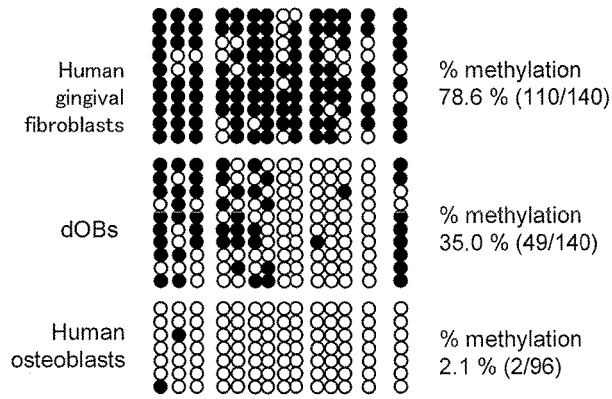
Figure 16D:
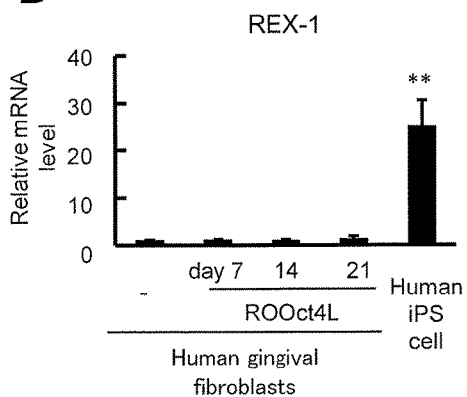
Figure 16E:
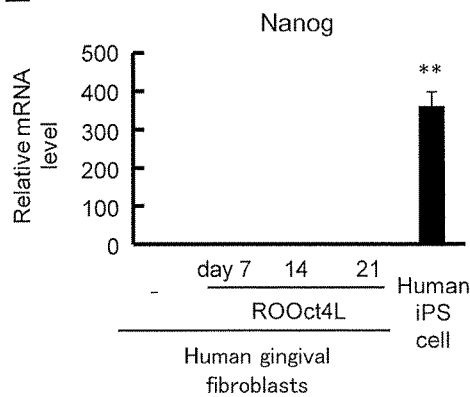

(14) Alizarin Red S Staining (FIG. 14)

Normal human gingival fibroblasts, Gin-1, were cultured in a 6-well plate and infected with a mixture (ROOct4L) of retrovirus vectors including human Runx2, Osterix, Oct4, and L-Myc genes, a mixture (ROOct4M) of retrovirus vectors including Runx2, Osterix, Oct4, and c-Myc genes, or a mixture (Oct4L) of retrovirus vectors including Oct4 and L-Myc genes. After the infection, the cells were cultured for day(s) shown in FIG. 14 (1 day to 28 days). Symbol (−) represents gingival fibroblasts, Gin-1, not infected with the retrovirus vectors. In addition, the human osteoblasts are NHost cells purchased from Lonza Walkersville, Inc. The Alizarin Red S staining was carried out as described below. The culture medium was removed by aspiration from the culture dish, and the cells were washed twice with PBS and fixed with 95% ethanol. The cells were washed with sterile distilled water, and then the Alizarin Red S staining solution was added thereto, followed by still standing at room temperature for 15 minutes. The cells were washed with sterile distilled water, then observed under an inverted phase-contrast microscope, and photographed. The cells infected with ROOct4L and Oct4L produced a large amount of calcified bone matrix, and even the cells infected with ROOct4M produced calcified bone matrix in an amount smaller than that in the cells infected with ROOct4L. ND: Not determined.

(15) Properties of Human Osteoblasts Induced by Direct Reprogramming (FIG. 15)

In the same manner as that shown in FIG. 14, human gingival fibroblasts (Gin-1) were infected with a mixture (ROOct4L) of retrovirus vectors including human Runx2, Osterix, Oct4, and L-Myc genes or a mixture (ROOct4M) of retrovirus vectors including Runx2, Osterix, Oct4, and c-Myc genes and cultured for 28 days. Symbol (−) represents gingival fibroblasts, Gin-1, not infected with the retrovirus vectors. NHost cells purchased from Lonza Walkersville, Inc. were used as the human osteoblasts. a: Quantification of calcium deposition by chelate method. The cells were washed well with PBS, then peeled off with a scraper, lysed with 0.5 M hydrochloric acid, and subjected to sonication. The lysate was centrifuged at 10,000 rpm for 5 minutes, and the supernatant was collected. 2 µL of the lysate was mixed with 240 µL of a Chlorophosphonazo-III solution (LS-MPR CPZ III, AKJ Global Technology, Chiba, Japan), and the cells were incubated for 10 minutes. An absorbance at 690 nm was measured using a microplate reader and compared to a standard curve to calculate the concentration of calcium (mg/dL). b-e: RNA was collected from the cells using ISOGEN II (Nippon Gene) and reverse-transcribed using ReverTra Ace qPCR RT Master Mix (TOYOBO). Real-time RT-PCR analysis was carried out using primers specific to the respective genes (shown in FIG. 25) and Real-time PCR Master Mix (TOYOBO) by 7300 Real Time PCR System (Applied Biosystems). The mRNA level of each sample was normalized by a β-actin mRNA level and then expressed as a relative value to a value of human gingival fibroblasts. f: A 2-(2-methoxy-4-nitrophenyl)-3-(4-nitrophenyl)-5-(2,4-disulfophenyl)-2H-tetrazolium monosodium salt solution (WST-8) (Cell Count Reagent SF; Nacalai Tesque) was added to the cells, and the cells were cultured at 37° C. for 1 hour. Absorbances at 450 nm and 650 nm of the supernatant were measured, and when a value of human gingival fibroblasts obtained without introduction of the genes was defined as 100%, the viability of the respective cells was calculated. *$P<0.05$ and **$P<0.01$, (significant differences with respect to the human gingival fibroblasts (Gin-1) obtained without introduction of the genes). #$P<0.05$, ##$P<0.01$. The values are mean±S.D. (n=4).

The cells infected with ROOct4L can cause deposition of a larger amount of calcium than the human osteoblasts. Even in the cells infected with ROOct4M, calcium can be deposited at the same level as that in human osteoblasts. Both of the cells infected with ROOct4L and the cells infected with ROOct4M express osteoblast-specific genes. In addition, the cells infected with ROOct4L have a sufficient proliferation ability.

(16) Analysis of Human Osteoblasts Induced by Direct Reprogramming (FIG. 16)

a: Human gingival fibroblasts (Gin-1), human gingival fibroblasts (Gin-1) infected with ROOct4L and then cultured for 20 days (referred to as dOBs in the following description and the drawings), and human osteoblasts (NHost cells purchased from Lonza Walkersville, Inc.) were immunostained with FITC-labeled anti-human osteocalcin antibody and FITC-labeled anti-osteopontin antibody. The magnification was 100 times. b: RNA was collected from the cells as described above and subjected to DNA microarray analysis using GeneChip (trademark) human Gene 1.0 ST (Affymetrix, Inc.). Based on the ratio of the expression level in the osteoblasts to the expression level in the human gingival fibroblasts, all the genes were classified into seven groups (less than 0.2, 0.2 or more and less than 0.33, 0.33 or more and less than 0.5, 0.5 or more and less than 2.0, 2.0 or more and less than 3.0, 3.0 or more and less than 5.0, 5.0 or more) (X-axis). The numbers of genes belonging to the respective groups are shown in parentheses. For the genes belonging to each group, the ratio (mean±S.D.) of the expression level in dOBs to the expression level in the human gingival fibroblasts was plotted. Genes strongly expressed in the osteoblasts compared to the human gingival fibroblasts were found to be strongly expressed also in dOBs, while genes weakly expressed in the osteoblasts were found to be weakly expressed also in dOBs, which indicated a significant correlation (coefficient of correlation R=0.70, P<0.01). c: DNA was collected from the cells as described above, and CpG methylation in the upstream region of osteocalcin gene was analyzed. DNA was collected using a Genomic DNA purification kit (Mag Extractor, Toyobo Life Science, Tokyo, Japan) and subjected to bisulfite treatment using an EZ DNA methylation kit (ZYMO research, Irvine, Calif.), and then the sequence in the upstream region of osteocalcin gene was amplified by PCR using a sense primer (5'-GTGTATTTG-GTAGTTATAGTTATTTGG) and an antisense primer (5'-CCTCAAATTAAACACTAACTAAACTC). The fragments were cloned into pTA2 vector, and then sequencing was carried out using T7 and T3 universal primers. The black wells show methylated CpG, and the white wells show unmethylated CpG. d-e: Human gingival fibroblasts (Gin-1) were infected with ROOct4L, and RNA was collected from the cells before the infection (−) and 7 days, 14 days, and 21 days after the infection. As a positive control, RNA was collected from human iPS cells. After reverse transcription, real time RT-PCR was carried out using REX-1 (d)—and Nanog (e)—specific primers. The mRNA level of each sample was normalized by a β-actin mRNA level and then expressed as a relative value to a value of human gingival fibroblasts. **P<0.01, (a significant difference with respect to human gingival fibroblasts (Gin-1) obtained by without introduction of the genes). The values are mean±S.D. (n=4).

The human dOBs were found to produce large amounts of osteocalcin and osteopontin (a). The human dOBs were also found to have an exhaustive gene expression profile similar to that of the human osteoblasts (b). The human dOBs were found to have an epigenetic mark of chromosomal DNA, which was different from that of the fibroblasts and became closer to that of the human osteoblasts (c). In addition, at any time point during the conversion caused by infection with ROOct4L from the fibroblasts into the dOBs, significant mRNA expression for REX-1 (d) and Nanog (e) genes was not observed, which suggested that the conversion did not occur via iPS cell-like cells (d and e).

Figure 17:
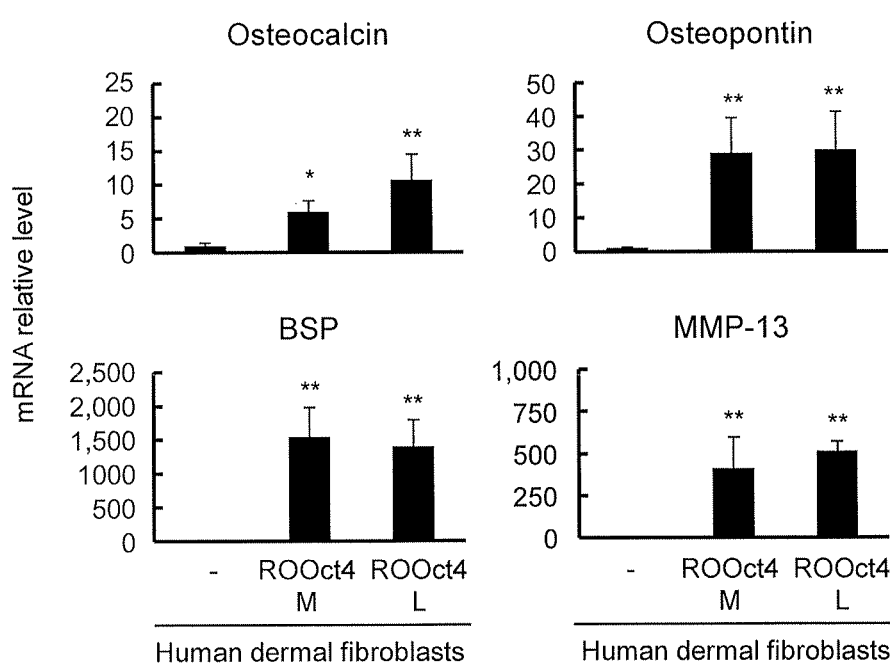
FIG. 17 is a result of quantification of expression levels of genes by real-time RT-PCR analysis.

(17) Results of Quantification of Expression Levels of Genes Introduced into Human Dermal Fibroblasts by Real-Time RT-PCR Analysis (FIG. 17)

The human dermal fibroblasts were infected with a mixture (ROOct4L) of retrovirus vectors including human Runx2, Osterix, Oct4, and L-Myc genes or a mixture (ROOct4M) of retrovirus vectors including Runx2, Osterix, Oct4, and c-Myc genes, and cultured for 14 days (d0). Symbol (−) represents gingival fibroblasts, Gin-1, not infected with the retrovirus vectors. In the same manner as in FIG. 15b to FIG. 15e, the expression levels of the genes were quantified by real-time RT-PCR analysis. The mRNA level of each sample was normalized by a β-actin mRNA level and then expressed as a relative value to a value of the human gingival fibroblasts (Gin-1). *P<0.05, **P<0.01 (significant differences with respect to human gingival fibroblasts obtained without introduction of the genes). #P<0.05, ##P<0.01. The values are mean±S.D. (n=4).

Figure 18A:
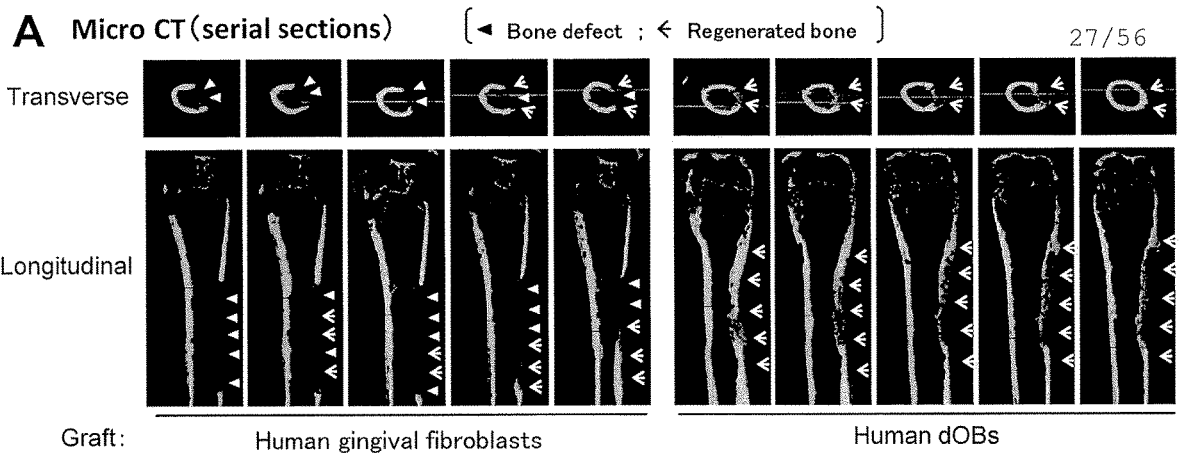
FIGS. 18A-18C are results of in vivo bone regeneration at bone defect sites.
Figure 18B:
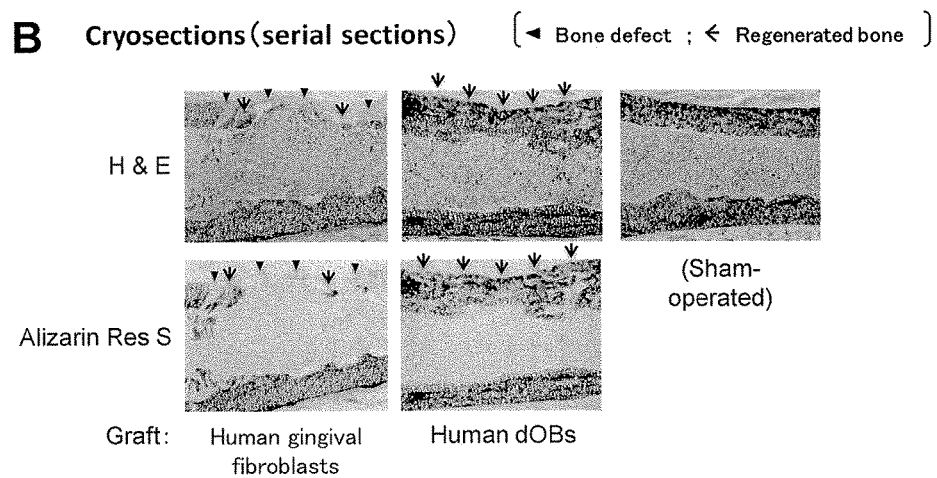
Figure 18C:
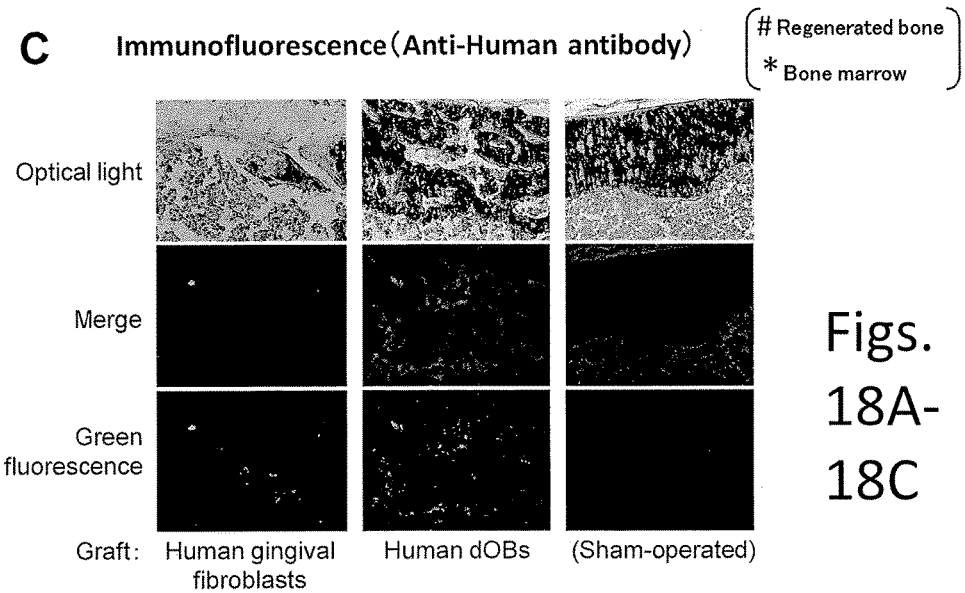

(18) In Vivo Bone Regeneration at Bone Defect Site (FIG. 18)

The dOBs (osteoblasts prepared by direct reprogramming) contribute to bone regeneration in a living body.

Animal experiments were carried out with the approval of Kyoto Prefectural University of Medicine. Eight-week-old male NOD/SCID mice (Charles River) were anesthetized by intraperitoneal injection with pentobarbital. A segmental bone defect having a diameter of about 4 mm was formed at the left femoral diaphysis using a dental drill with pouring water. Human gingival fibroblasts (Gin-1) and cells induced by infecting Gin-1 with a mixture (ROOct4L) of retrovirus vectors including human Runx2, Osterix, Oct4, and L-Myc genes and culturing the cells for 14 days (referred to as dOBs in the following description and drawings) were suspended in 25 μL of a medium and 75 μL of Matrigel (BD Bioscience, San Jose, Calif.) and transplanted to the bone defect site at a concentration of 5×10$^5$ cells/mouse. Mice subjected to the same operation as that described above without creation of the bone defect and transplantation were also prepared (sham operation). a: Micro-computed tomography (μCT) images. 21 Days after the transplantation, mice were anesthetized by intraperitoneal injection with pentobarbital. The thigh was excised, fixed with neutral formalin, and then photographed with an X-ray CT device (Scan Xmate-L090, Com Scan Techno, Yokohama, Japan). 10-μm Serial tomographic images are shown. The triangle represents a bone defect, and the arrowhead represents a regenerated bone trabecula. b: The tissue of the bone defect site was embedded in SCEM (Leica Microsystem) compound and frozen rapidly. The tissue was sliced into 6-μm sections, and then the serial sections were stained with hematoxylin eosin (H&E) (upper) and Alizarin Red S (lower). The triangle represents a bone defect, and the arrowhead represents a regenerated bone trabecula. The magnification was 40 times. c: The above-mentioned 6-μm sections were fixed with 4% paraformaldehyde and immunostained with a human nucleus-specific mouse monoclonal antibody (Cat: MAB1281; clone: 235-1; Millipore, Billerica, Mass.). Symbol "#" represents a regenerated bone trabecula, and Symbol "*" represents to bone marrow. The magnification was 100 times.

The micro-CT images (a) and the histological images (b) show that, in the bone transplanted with the human dOBs, the defect site was completely covered by forming a bony callus including bone trabeculae aligned. In the bone transplanted with the fibroblasts, only few calluses were formed, and the bone defect remained. The immunofluorescent images (c) show that, in the bone transplanted with the human dOBs, many transplanted dOBs succeeded in engraftment at the bone regeneration site. In the bone transplanted with the fibroblasts, only a small number of transplanted fibroblasts succeeded in engraftment.

Figure 19:
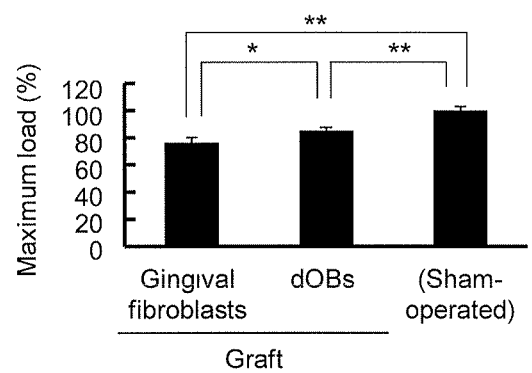
FIG. 19 is a graph for showing in vivo bone regeneration at bone defect sites (mechanical strength).

(19) In Vivo Bone Regeneration at Bone Defect Site (FIG. 19)

Figure 21:
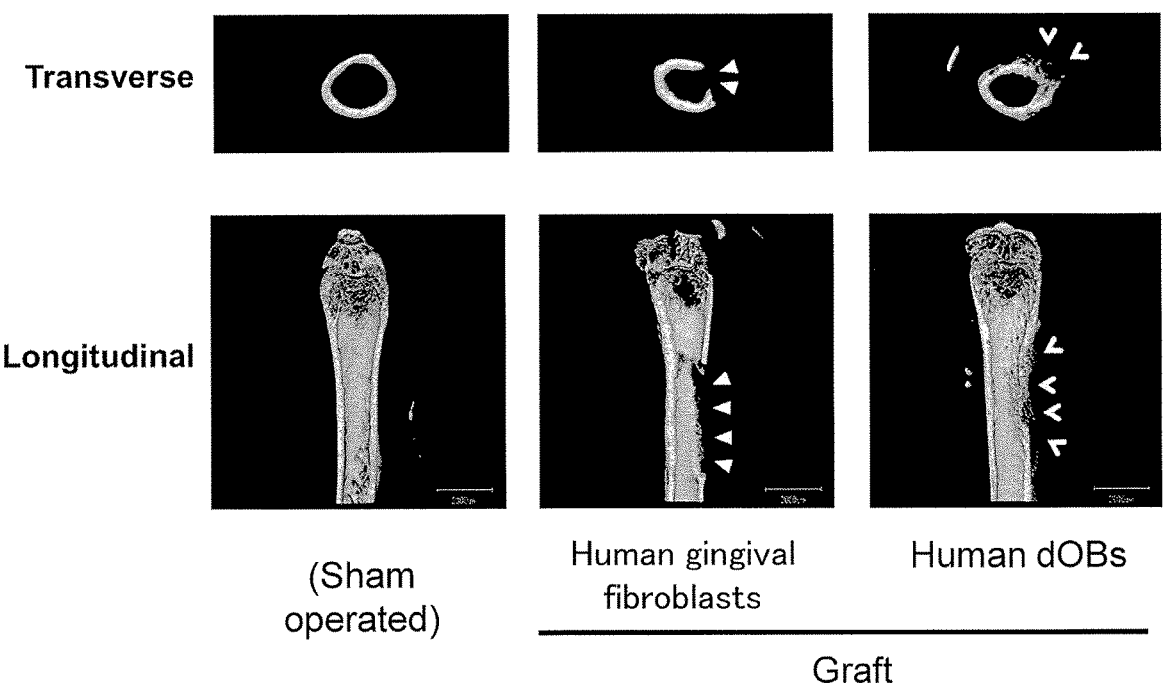

After the same transplantation experiment as shown in FIGS. 18, 21 days after the transplantation, the mice were euthanized, and the femur was collected. A three point bending test was carried out to measure a maximum loading value. In the group transplanted with osteoblasts (dOBs) induced by infection with RO Oct4L and then culture for 14 days, the mechanical strength of the femur was enhanced significantly compared to the group transplanted with the gingival fibroblasts. The term "Sham operated" refers to the femur of mice subjected to the same operation as that described above without creation of the bone defect and transplantation. *P<0.05, **P<0.01. The values are mean±S.D. (n=3).

(20) In Vivo Bone Regeneration at Bone Defect Site (FIG. 20)

Days after the transplantation of human gingival fibroblasts (left) and dOBs (right) by the same experiment as shown in FIG. 18, the bone defect site of the femur was photographed with a stereomicroscope. The photographs are stereomicroscopic images (upper) (magnification: 10 times) and stereomicroscopic images superimposed with instructions (lower). Symbol "*" represents a bone defect, and Symbol "#" represents a regenerated bone.

In the bone transplanted with the human dOBs, a bony callus including bone trabeculae aligned was formed, and the defect site was completely covered and could not be visually observed. In the bone transplanted with the fibroblasts, only few calluses were formed, and the bone defect remained at a high ratio.

(21) Three-Dimensional Reconstructed Images of Micro-Computed Tomography (μCT) Data Shown in FIG. 18a (FIG. 21)

The triangle represents a bone defect, and the arrowhead represents a regenerated bone trabecula.

In the bone transplanted with the human dOBs, a bony callus including bone trabeculae aligned was formed, and the defect site was completely covered. In the bone transplanted with the fibroblasts, only few calluses were formed, and the bone defect remained.

Figure 22:
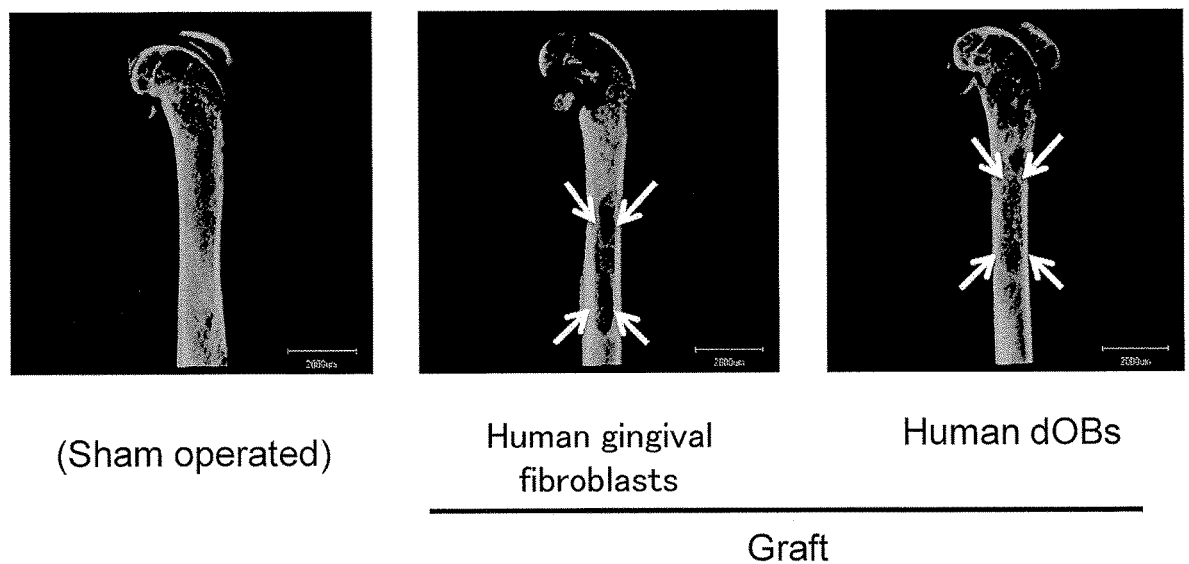
FIG. 22 is a pCT transmission image obtained by the same experiment as that shown in FIGS. 18A-18C. The arrows represent bone defect sites. A bone transplanted with osteoblasts (dOBs) induced by direct reprogramming has high radiopacity at a bone defect site compared to a bone transplanted with human gingival fibroblasts.

(22) pCT Transmission Images in Experiment Shown in FIG. 18a (FIG. 22)

μCT transmission images obtained by the same experiment as shown in FIG. 18a are shown. The arrow represents a bone defect site. In the bone transplanted with the osteoblasts (dOBs) induced by direct reprogramming, radiopacity at a bone defect site was higher than that in the bone transplanted with the human gingival fibroblasts.

Figure 26B:
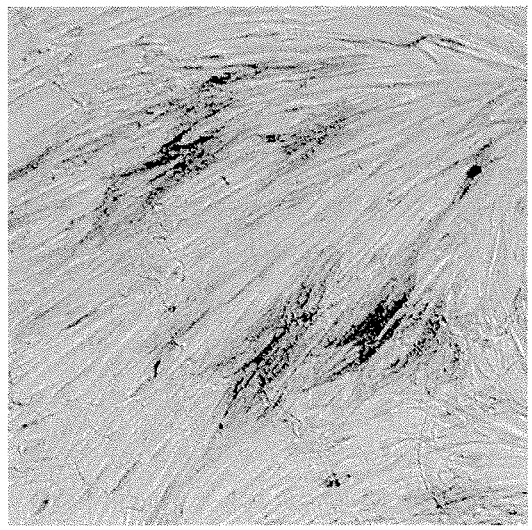
Figure 27A:
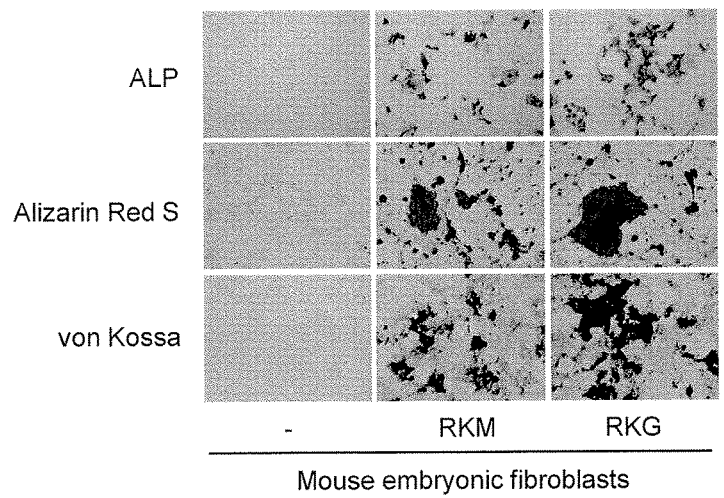
FIGS. 27A-27B are results of direct reprogramming into mouse osteoblasts.
Figure 27B:
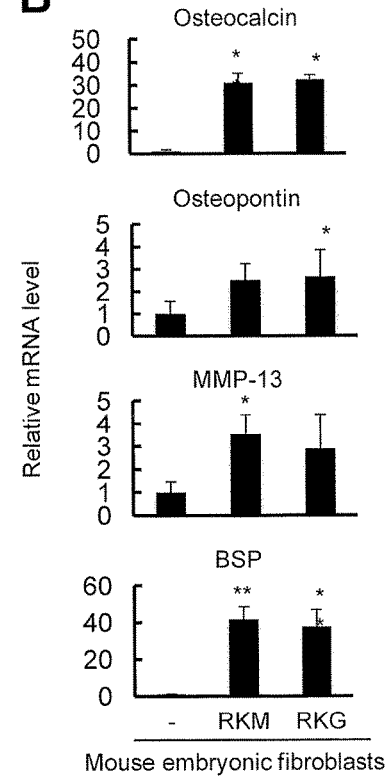

(23) Direct Reprogramming into Osteoblasts with Episomal Vector (FIG. 26)

Human Runx2, Osterix, Oct4, and L-Myc genes were each inserted to the EcoRI site of pG.oriPP9.EBNA1 episomal vector (pG.oriPP9.hRunx2.EBNA1 having inserted therein Runx2 is shown in FIG. 26a). $2 \times 10^5$ human gingival fibroblasts (Gin-1) were resuspended in the normal medium (1% NEAA 10% FBS DMEM containing 100 U/ml penicillin and 100 μg/ml streptomycin) as used in the experiment shown in FIG. 1, inoculated into a 35-mm dish, and cultured for 1 day. A mixture of episomal vectors of the above-mentioned four genes (0.5 μg each), Extreme GENES DNA Transfection Regent (6 μL), and Opti-MEM (200 μl) were blended and added to the above-mentioned cells to transfect the cells. The cells were cultured for 1 day, and the medium was then discarded and exchanged for an osteoinductive medium (obtained by adding 50 μg/ml ascorbic acid, 10 mM β-glycerophosphate, and 100 nM dexamethasone (all of the concentrations are final concentrations) to a normal medium), followed by culture. 14 Days after the introduction of the genes, the cells were subjected to ALP staining. An inverted phase-contrast microscope image is shown (b). The abbreviations in FIG. 26a represent the following meanings. CAG prom: CAG promoter, poly A: poly A addition signal, oriP: Epstein-Barr virus oriP sequence, EBNA1: Epstein-Barr virus nuclear antigen 1 gene, KanR: kanamycin-resistant gene.

(24) Direct Reprogramming in Mouse Osteoblasts (FIG. 27)

Mouse fetal fibroblasts were infected with a mixture (RKM) of retrovirus vectors including Runx2, Klf4, and c-Myc or a mixture (RKG) of retrovirus vectors including Runx2, Klf4, and Glis1, and were then cultured for x day(s). Some of the cells were not infected. a: The cells were subjected to alkaline phosphatase (ALP) staining, Alizarin Red S staining, and von Kossa staining. The magnification was 40 times. b: RNA was collected from the cells, and the expression levels of the genes described above were quantified by real-time RT-PCR analysis. The mRNA level of each sample was normalized by β-actin mRNA level and then expressed as a relative value to a value of mouse fetal fibroblasts obtained without introduction of the genes. *P<0.05 and **P<0.01, (significant differences with respect to mouse fetal fibroblasts obtained without introduction of the genes). #P<0.05, ##P<0.01. The values are mean±S.D. (n=4).

Figure 28A:
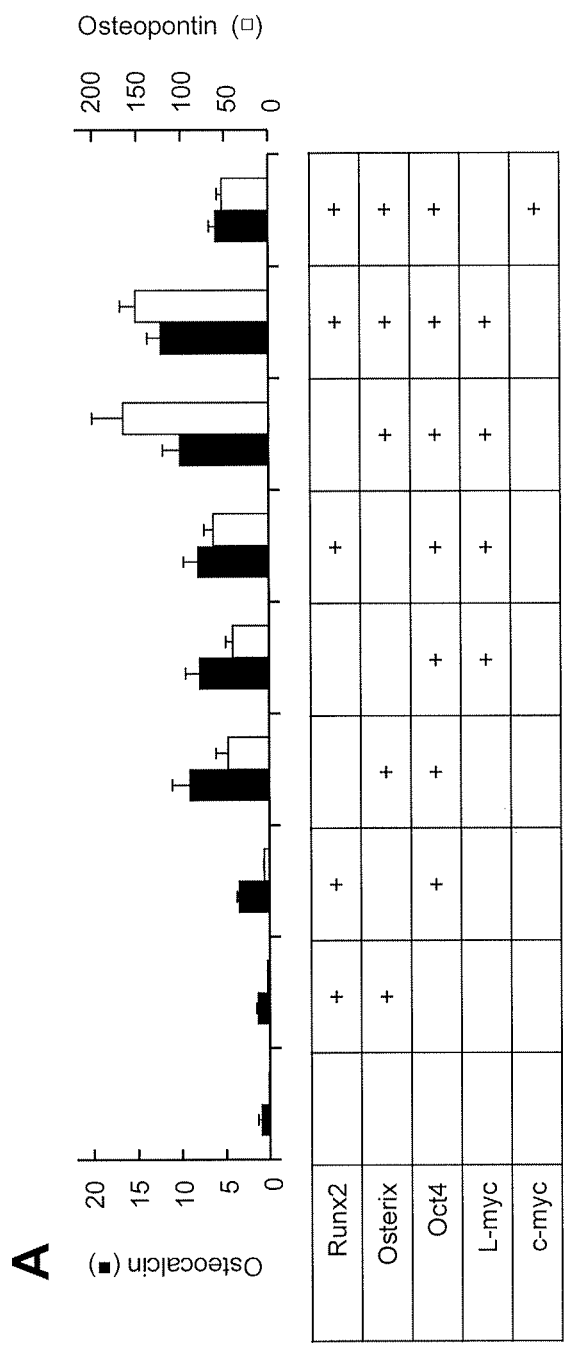
FIG. 28A is a result of measurement of mRNA expression levels of hOsteopontin (□) and hOsteocalcin (■) by real-time RT-PCR, and each of the genes introduced is represented as "+".
Figure 28B:
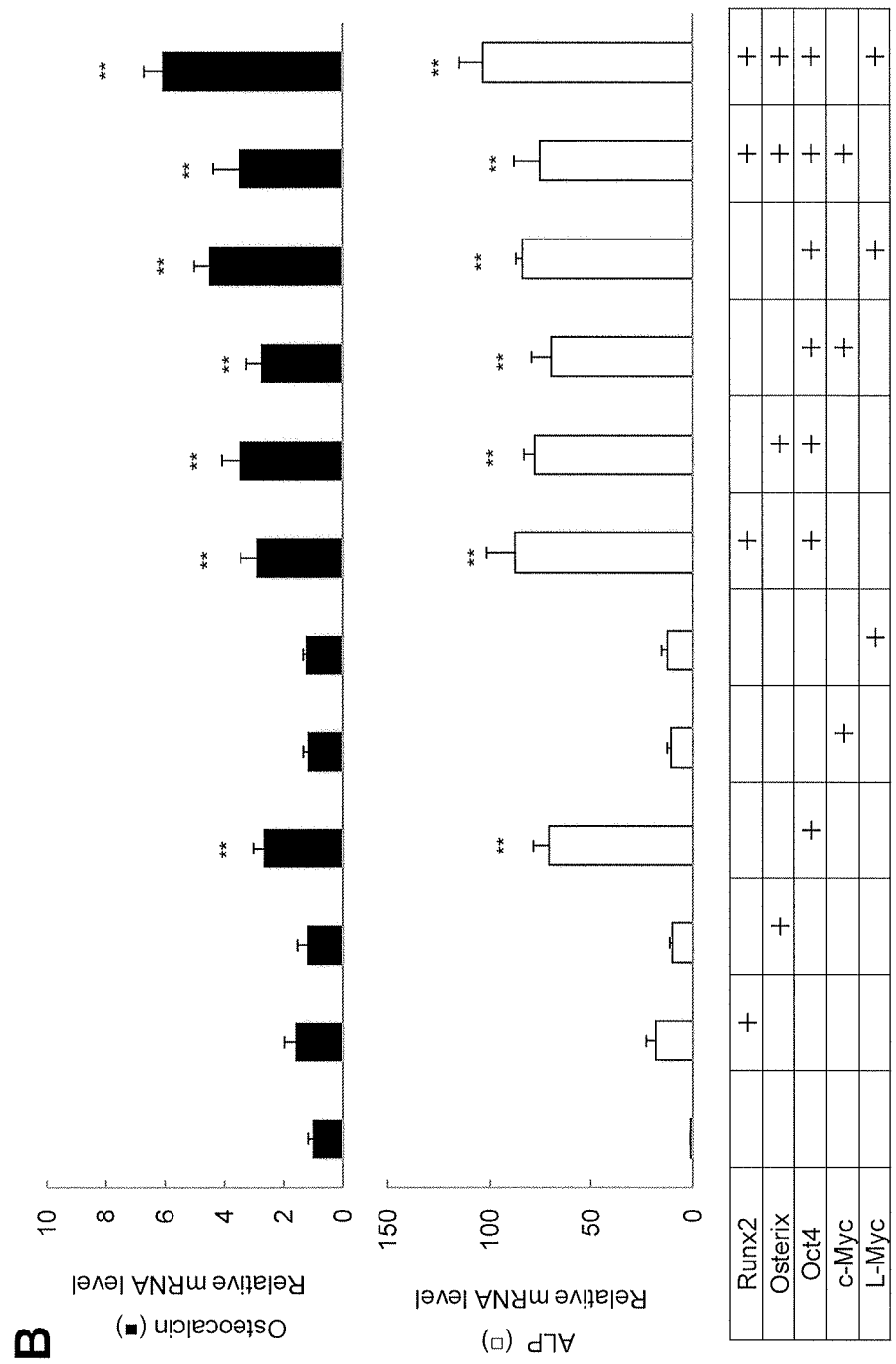
FIG. 28B is a result of measurement of mRNA expression levels of hOsteocalcin (■) and APL (□) by real-time RT-PCR, and each of the genes introduced is represented as "+".
Figure 28C:
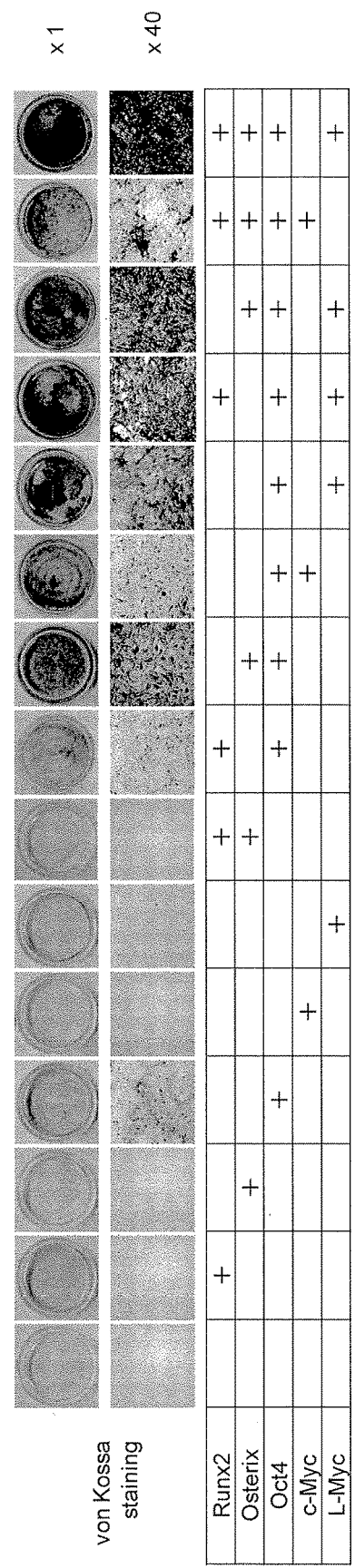
FIG. 28C is a result of von Kossa staining. Each of the genes introduced is represented as "+".

(25) Direct Reprogramming of Normal Human Gingival Fibroblast Strain Gin-1 (FIG. 28a, FIG. 28b, and FIG. 28c)

A normal human gingival fibroblast strain, Gin-1, was cultured in a 35-mm dish and subjected to an experiment as illustrated in FIG. 2. The sign "+" in the table represents infection with retrovirus vectors including the respective genes, and the blank represents non-infection with retrovirus vectors including the respective genes.

a: 14 days after the introduction of the genes, RNA was collected from the cells, and osteocalcin mRNA (black bar) and osteopontin mRNA (white bar) were quantified by real-time RT-PCR. Each bar represents mean±standard deviation. N=3. *P<0.05 and **P<0.01 (compared to non-infected cells).

b: 14 days after the introduction of the genes, RNA was collected from the cells, and osteocalcin mRNA (black bar) and ALP mRNA (white bar) were quantified by real-time RT-PCR. Each bar represents mean±standard deviation. N=3. **P<0.01 (compared to non-infected cells).

c: 28 days after the introduction of the genes, the culture was removed by aspiration from the culture dish, and the cells were washed twice with PBS and fixed with 10% formalin. The cells were washed with sterile distilled water, and then a 5% silver nitrate solution was added thereto, followed by standing under a UV light for 30 minutes. After that, the cells were washed with sterile distilled water, and a 5% thiosulfate solution was added thereto and allowed to react for 2 minutes. The cells were washed with sterile distilled water and then observed with the naked eye and under an inverted phase-contrast microscope.

The cells infected with the retrovirus vectors including Osterix+Oct4+L-Myc genes and Runx2+Osterix+Oct4+L-Myc genes were found to produce large amounts of calcified bone matrix. In addition, the cells infected with the retrovirus vector including the Oct4+L-Myc genes were also found to produce a large amount of calcified bone matrix.

(26) Properties of Human Osteoblasts Induced from Human Fibroblasts by Direct Reprogramming (FIG. 29a and FIG. 29b)

Human gingival fibroblasts (Gin-1) were infected with a mixture (ROOct4L) of retrovirus vectors including human Runx2, Osterix, Oct4, and L-Myc genes or a mixture (Oct4L) of retrovirus vectors including Oct4 and L-Myc genes, and were cultured for 14 days. The sign (−) represents gingival fibroblasts, Gin-1, not infected with the retrovirus vectors. NHost cells purchased from Lonza Walkersville, Inc. were used as human osteoblasts. In the same manner as in FIG. 15b to FIG. 15e, RNA was collected from the cells using ISOGEN II (Nippon Gene) and reverse-transcribed using ReverTra Ace qPCR RT Master Mix (TOYOBO). Real-time RT-PCR analysis was carried out using primers specific to the respective genes (shown in FIG. 29b), Real-time PCR Master Mix (TOYOBO), and 7300 Real Time PCR System (Applied Biosystems). The results are shown in FIG. 29a. The mRNA level of each sample was normalized by β-actin mRNA level and then expressed as a relative value to a value of the human gingival fibroblasts. *P<0.05 and **P<0.01, (a significant difference with respect to human gingival fibroblasts (Gin-1) obtained without introduction of the genes). #P<0.05, ##P<0.01. The values are mean±S.D. (n=4).

Both of the cells infected with ROOct4L and the cells infected with Oct4L expressed genes specific to osteoblasts.

Figures 30A, 30B:
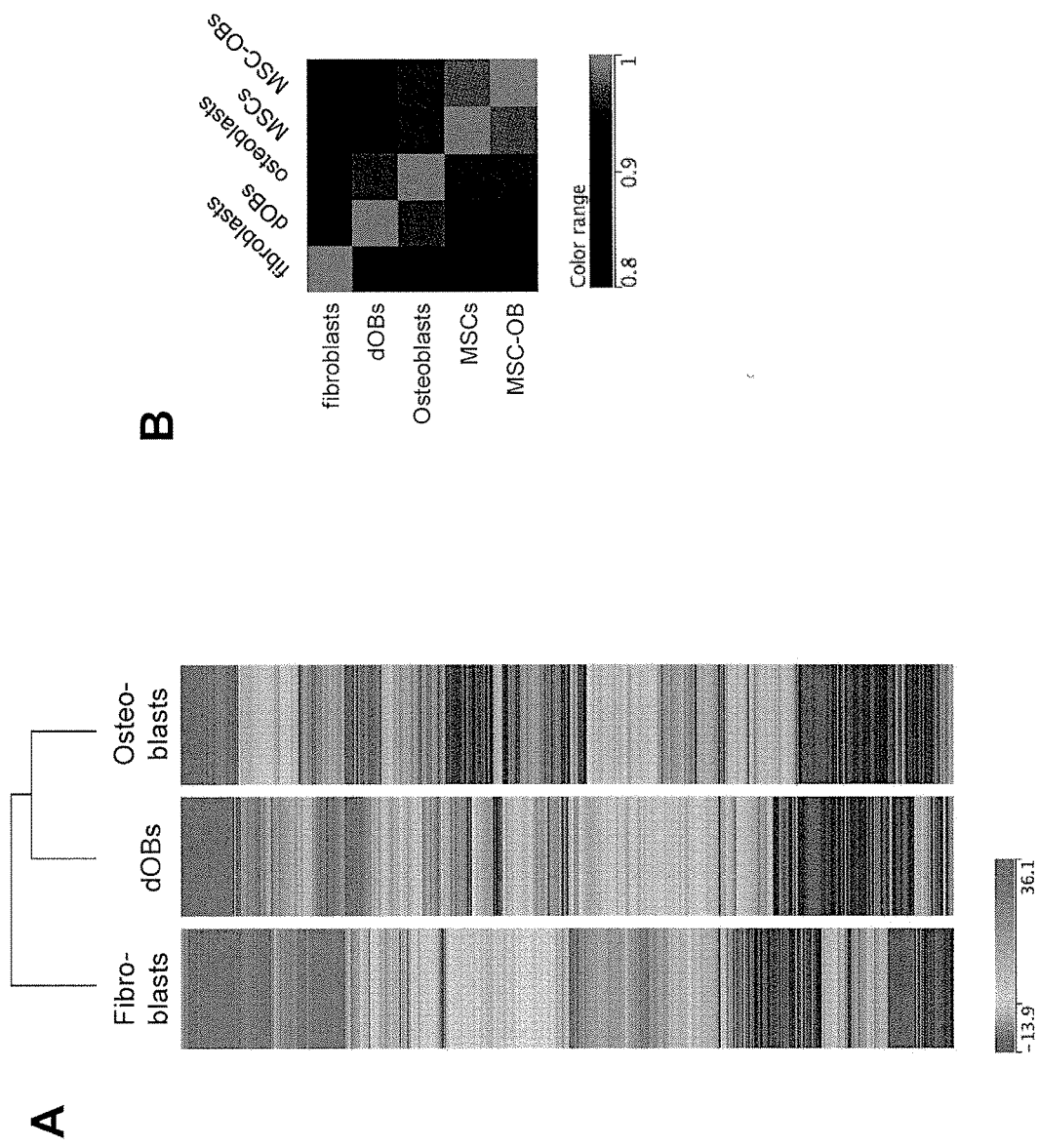
FIGS. 30A-30B are results of an exhaustive gene expression profile of osteoblasts induced from human fibroblasts by direct reprogramming.

(27) Exhaustive Gene Expression Profile of Osteoblasts Induced from Human Fibroblasts by Direct Reprogramming (FIG. 30)

RNA was collected from the following cells. dOBs: Osteoblasts induced by infecting human gingival fibroblasts (Gin-1) with a mixture (ROOct4L) of retrovirus vectors including human Runx2, Osterix, Oct4, and L-Myc genes. Fibroblasts: Gingival fibroblasts Gin-1 not infected with the vectors. Osteoblasts: Human osteoblasts (NHost cells) purchased from Lonza Walkersville, Inc. The cells were subjected to exhaustive gene expression analysis using GeneChip (trademark) human Gene 1.0 ST manufactured by Affymetrix. MSCs: Human bone marrow mesenchymal stem cells. MSC-OBs: Osteoblasts induced by culturing human bone marrow mesenchymal stem cells in a medium for osteoblasts. a): A heat map and a cluster analysis of genes having increased and decreased in expression levels twice or more compared to fibroblasts. b): A heat map of all genes. The results show that the gene expression profile of the dOBs is significantly different from that of the original fibroblasts and is similar to that of the osteoblasts. The similarity between the dOBs and the osteoblasts is higher than that between MSC-OBs and the osteoblasts.

Figure 31A:
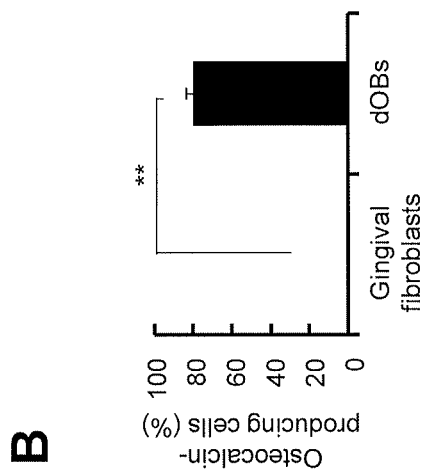
FIGS. 31A-31B are results of analysis of human osteoblasts induced by direct reprogramming. (a) Immunostaining, (b) Efficiency of direct reprogramming.
Figure 31B:
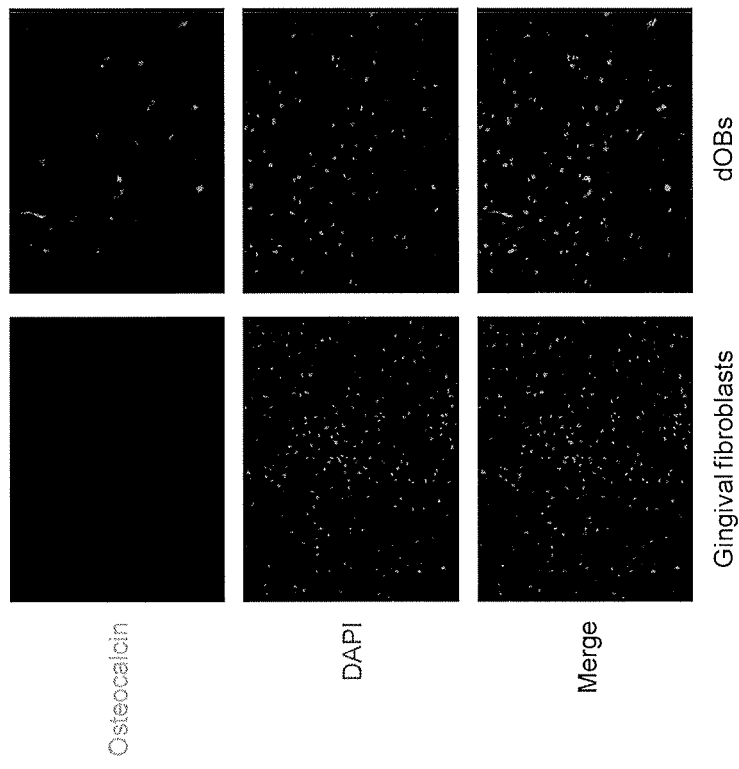

(28) Efficiency of Direct Reprogramming is about 80%. (FIG. 31)

a): Osteoblasts (dOBs) induced by infecting human gingival fibroblasts (Gin-1) with a mixture (ROOct4L) of retrovirus vectors including Runx2, Osterix, Oct4, and L-Myc genes, and then culturing the cells for 21 days were stained with an anti-human osteocalcin and Alexa fluor 488-labeled secondary antibody and DAPI. DAPI can stain nuclei of all cells, and most of DAPI-positive cells can produce osteocalcin.

b): The numbers of the osteocalcin(+)DAPI(+) cells and DAPI(+) cells were counted. The numbers were calculated based on the following expression:

Ratio of osteocalcin-producing cells=Number of osteocalcin(+)DAPI(+) cells/Number of DAPI(+) cells×100. About 80% of the fibroblasts were found to be converted into osteoblasts. Mean±S.D. (n=5). **P<0.01.

Figure 32:
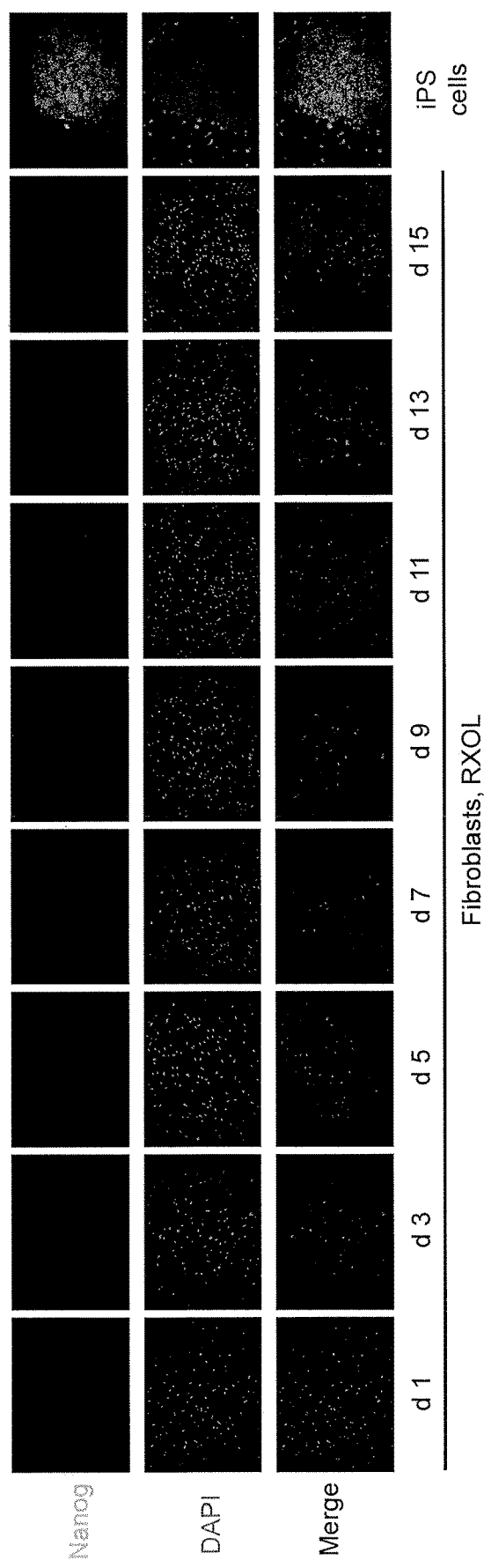
FIG. 32 is a result showing that reprogramming from human fibroblasts into osteoblasts is caused by direct conversion without a pluripotent stem cell-like phase. (a) Immunostaining, (b) Real-time RT-PCR.

(29) Reprogramming from Human Fibroblasts to Osteoblasts is Direct Conversion without Pluripotent Stem Cell-Like Phase (FIG. 32)

Human gingival fibroblasts (Gin-1) were infected with a mixture (ROOct4L) of retrovirus vectors including Runx2, Osterix, Oct4, and L-Myc genes. From day 1 to day 15 after infection every second day, the cells were fixed with paraformaldehyde at 4° C. for 30 minutes. The cells were permeabilized with 0.2% Triton X-100 at room temperature for 15 minutes, and then stained with anti-Nanog antibody and Alexa fluor 488-labeled secondary antibody and DAPI. The cells were observed under a fluorescence microscope, and 1,000 or more DAPI-positive cells were observed in each sample. However, Nanog-positive cells were not observed at any timepoint. Typical fluorescence microscope images are shown (magnification: 100 times). As a positive control, human iPS cells were stained in the same manner as above, and in all the cells, Nanog was strongly expressed.

Figure 33:
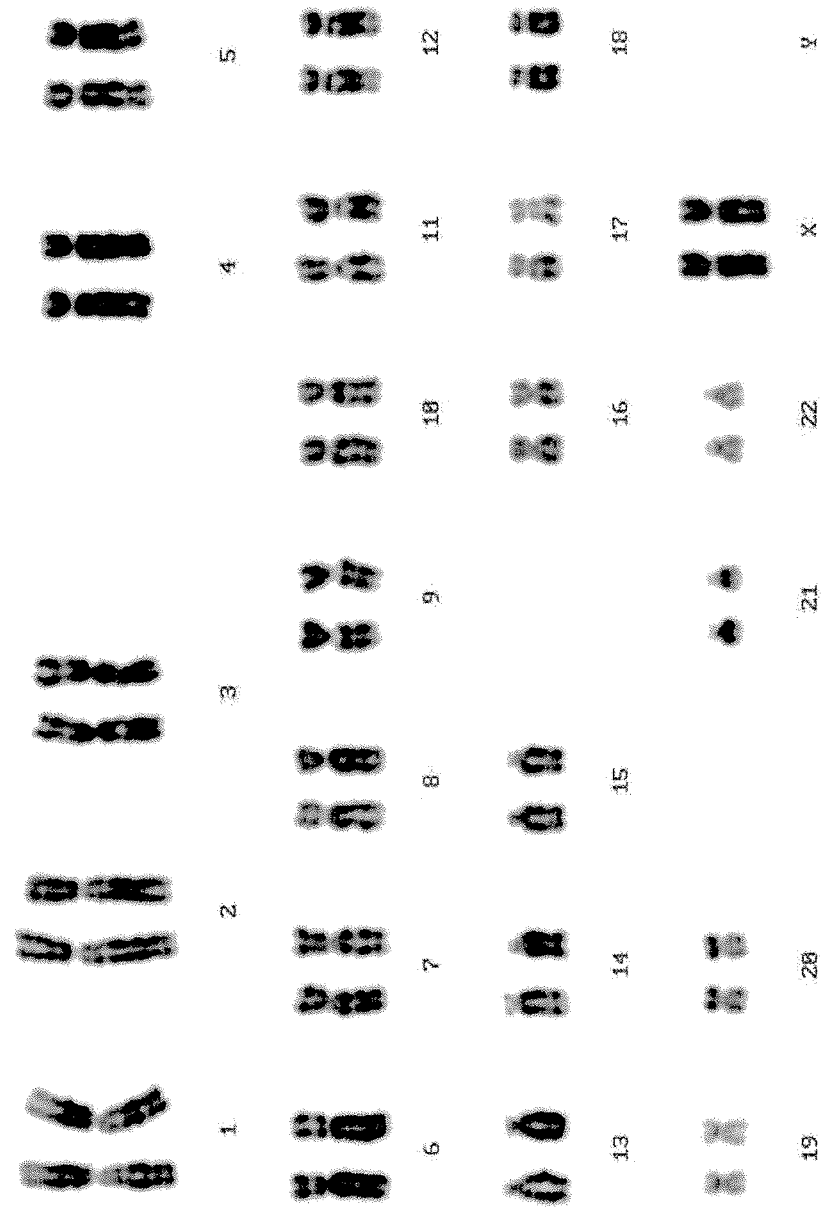
FIG. 33 is a result of karyotype analysis.

(30) Osteoblasts Induced from the Normal Human Dermal Fibroblasts by the Direct Reprogramming have No Abnormal Karyotype (FIG. 33)

The human fibroblasts were infected with a mixture (ROOct4L) of retrovirus vectors including Runx2, Osterix, Oct4, and L-Myc genes. 14 Days after that, when the osteoblasts were subjected to karyotype analysis, a normal karyotype was displayed.

Figure 34:
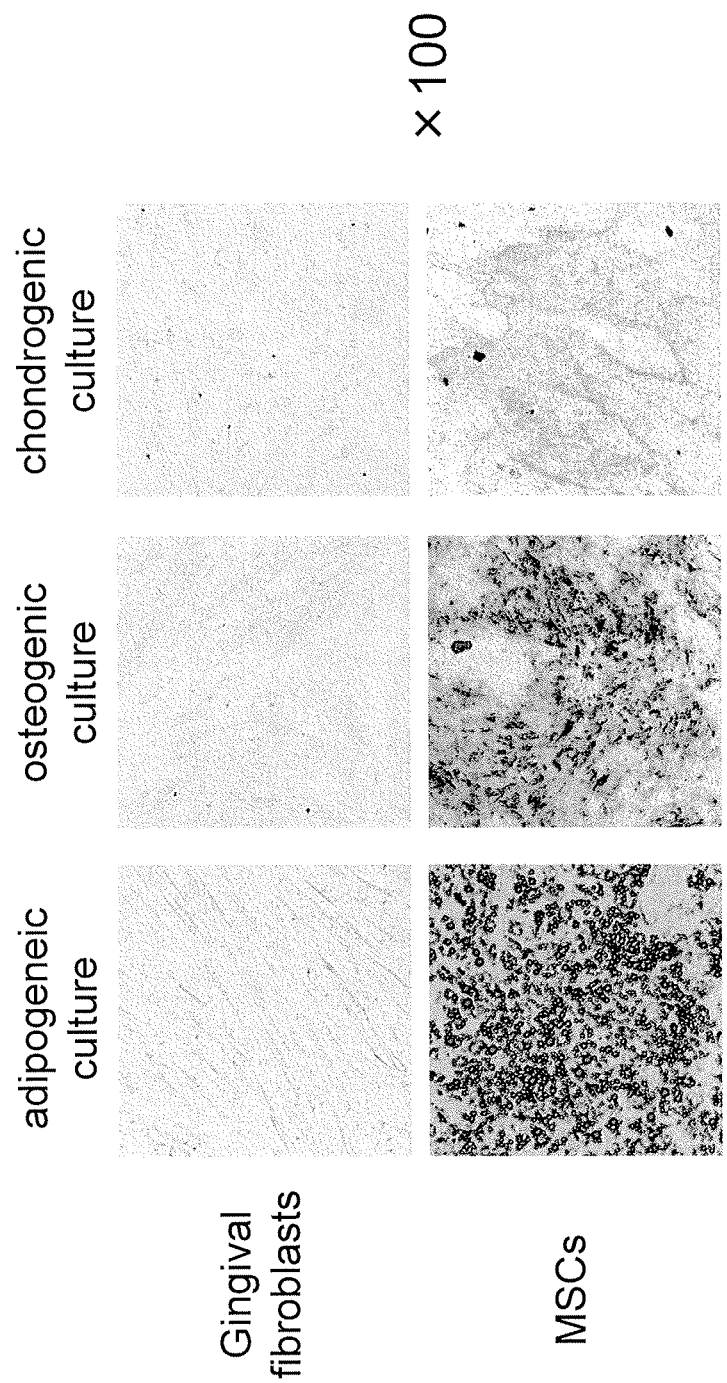
FIG. 34 is a result showing that human fibroblasts include no mesenchymal stem cells (MSCs) incorporated.

(31) Human Fibroblasts Include No Mesenchymal Stem Cells (MSCs) Incorporated (FIG. 34)

Human gingival fibroblasts (Gin-1), and, as a positive control, mesenchymal stem cells (MSCs) derived from a human adipose tissue were independently cultured in the following mediums: a medium for inducing differentiation into adipose cells (left), a medium for inducing differentiation into osteoblasts (center), and a medium for inducing differentiation into chondrocytes (right). The cells were cultured for 21 days and then subjected to Oil 0 Red staining (left), Alizarin Red S staining (center), and Alcian blue staining (right). Unlike the case of MSCs, there were no cells differentiated from Gin-1 into adipose cells, osteoblasts, and chondrocytes.

The results can eliminate the possibility that the osteoblasts were obtained by differentiation from MSCs due to incorporation of the MSCs into the fibroblasts.

Figure 35:
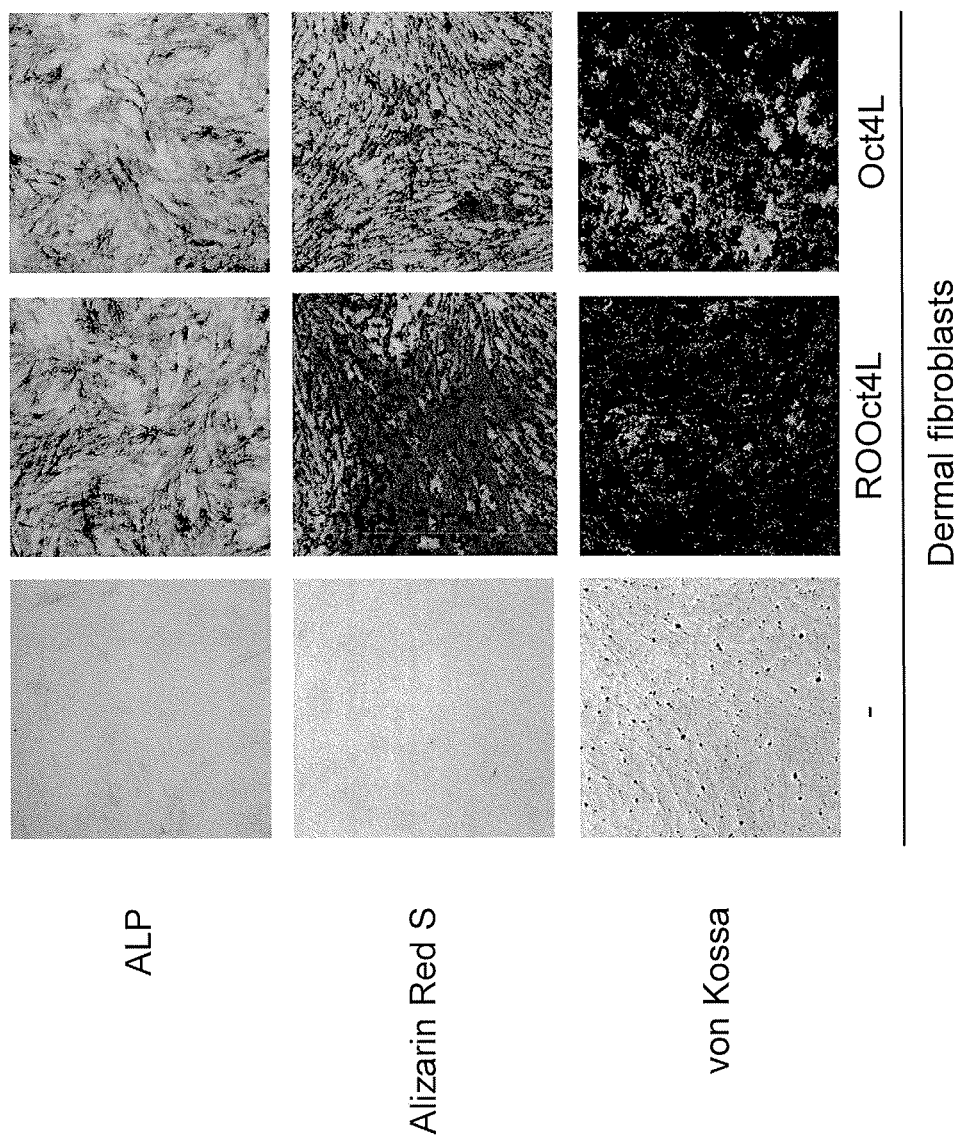
FIG. 35 is a result of staining of human osteoblasts induced from human fibroblasts by direct reprogramming.

(32) Properties of Human Osteoblasts Induced from Human Fibroblasts by Direct Reprogramming (FIG. 35)

Normal human dermal fibroblasts were infected with a mixture (ROOct4L) of retrovirus vectors including human Runx2, Osterix, Oct4, and L-Myc genes or a mixture (Oct4L) of retrovirus vectors including Oct4 and L-Myc genes, and were cultured. The sign (–) represents normal dermal fibroblasts not infected with the retrovirus vectors. 14 days after the introduction of the genes, the cells were subjected to ALP staining in the same manner as shown in FIG. 5. In addition, 28 days after the introduction of the genes, the cells were subjected to Alizarin red S staining in the same manner as shown in FIG. 14. In addition, 28 days after the introduction of the genes, the cells were subjected to von Kossa staining in the same manner as shown in FIG. 8.

Figure 36:
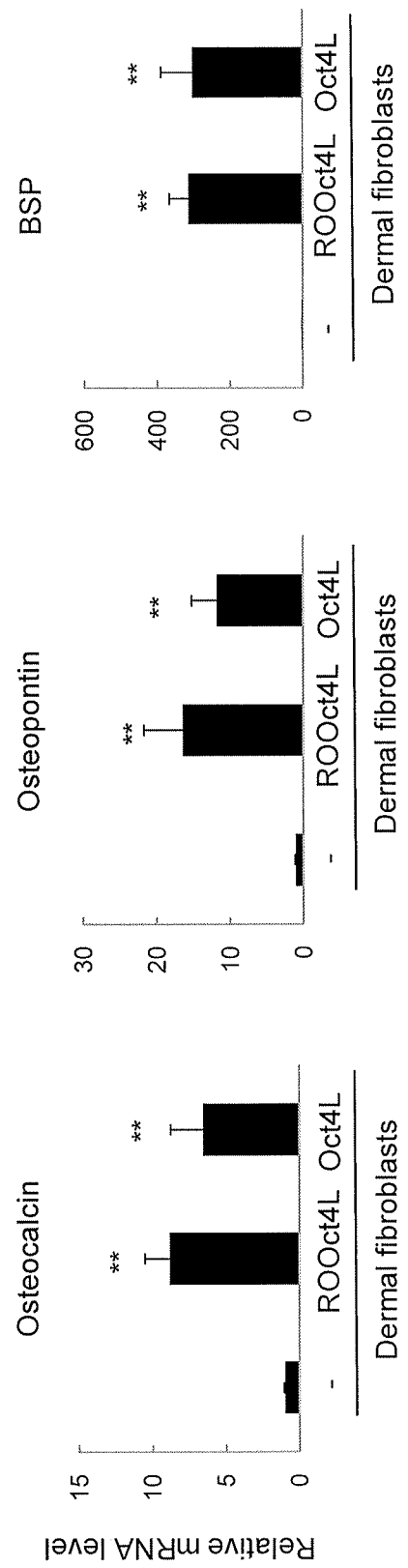
FIG. 36 is a result of measurement of mRNA expression levels of genes by real-time RT-PCR.

(33) Properties of Human Osteoblasts Induced from Human Fibroblasts by Direct Reprogramming (FIG. 36)

Normal Human Dermal Fibroblasts were Infected with a Mixture (ROOct4L) of retrovirus vectors including human Runx2, Osterix, Oct4, and L-Myc genes or a mixture (Oct4L) of retrovirus vectors including Oct4 and L-Myc genes, and were cultured. RNA was collected from the cells using ISOGEN II (Nippon Gene) in the same manner as in FIG. 15b to FIG. 15e and reverse-transcribed using ReverTra Ace qPCR RT Master Mix (TOYOBO). Real-time RT-PCR analysis was carried out using primers specific to the respective genes (shown in FIG. 25), Real-time PCR Master Mix (TOYOBO), and 7300 Real Time PCR System (Applied Biosystems). The mRNA level of each sample was normalized by β-actin mRNA level and then expressed as a relative value to a value of the normal human dermal fibroblasts. **P<0.01 (a significant difference with respect to normal human dermal fibroblasts obtained without introduction of the genes). The values are mean±S.D. (n=4).

Both of the normal human dermal fibroblasts infected with ROOct4L and the normal human dermal fibroblasts infected with Oct4L can express osteoblast-specific genes.

Figure 37:
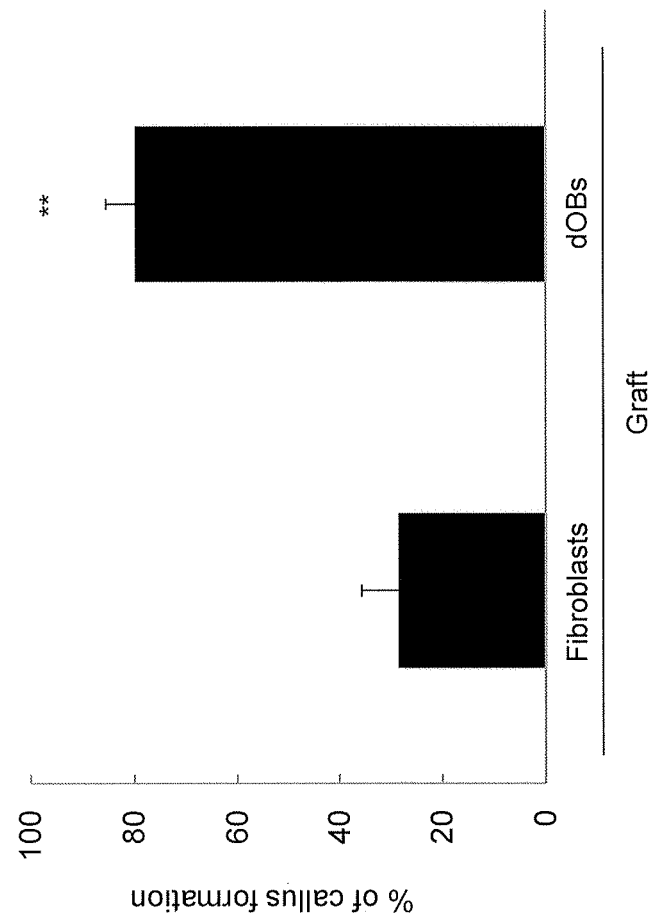
FIG. 37 is a result of in vivo bone regeneration at bone defect sites.

(34) Properties of Human Osteoblasts Induced from Normal Human Gingival Fibroblasts by Direct Reprogramming (FIG. 37)

Human fibroblasts, and, osteoblasts (dOBs) induced by introducing ROOct4L into human fibroblasts and then culturing the cells were transplanted to an artificial bone defect site of the femur of NOD/SCID mice in the same way as that in FIG. 18. Three weeks later, the femur was collected, and tissue sections were prepared and subjected to HE staining. Based on histological images of the sections, a distance in the long axis direction of a region at which the defect was formed and a distance of the region at which calluses were formed were measured to calculate "% of callus formation" from the following expression: % of callus formation=a ratio (%) of a distance of a region at which calluses were formed to a distance in the long axis direction of a region at which a defect was formed. The values are mean±S.D. **P<0.01.

Figure 38:
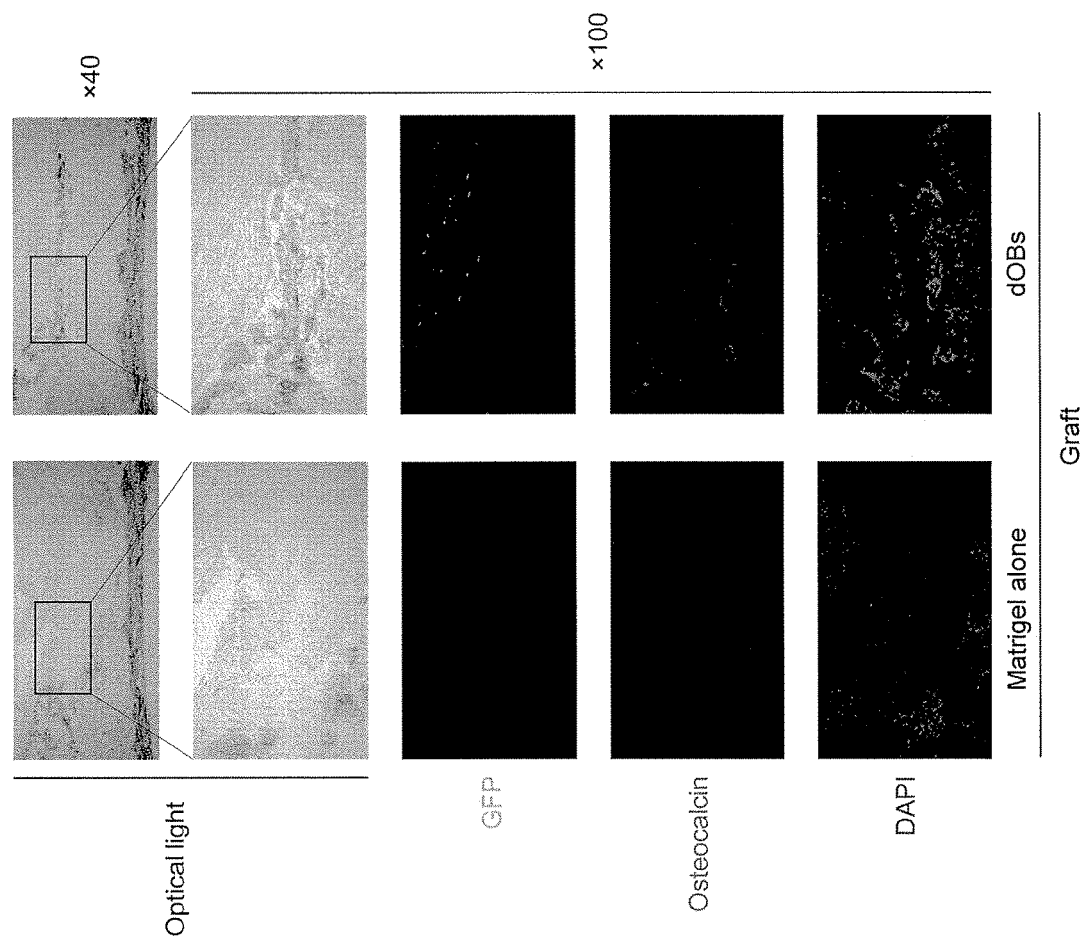
FIG. 38 is a result of in vivo bone regeneration at bone defect sites.

(35) dOBs Transplanted to a Living Body Produced a Bone Matrix and Contributed Directly to Bone Regeneration (FIG. 38)

A GFP gene was introduced with a retrovirus vector into osteoblasts (dOBs) induced by introducing ROOct4L into normal human gingival fibroblasts and then culturing the cells. In the same manner as in FIG. 18, the cells were transplanted to an artificial bone defect site of the femur of NOD/SCID mice (right). As a negative control, Matrigel alone was transplanted to an artificial bone defect site of the femur of NOD/SCID mice (left). Three weeks later, the femur was collected, and tissue sections were prepared and subjected to immunostaining with an anti-human osteocalcin antibody (not reactive with mouse OCs) and DAPI. In the dOBs-transplanted group, significant formation of calluses was observed at the bone defect site, and the transplanted dOBs succeeded in engraftment in the bone periphery of the callus site. In addition, human osteocalcin was detected at the callus site and in the bone periphery of the callus site. The foregoing suggests that the transplanted human dOBs succeeded in engraftment in the bone periphery of the callus site as is the case with physiological bone regeneration. Further, the foregoing shows that the dOBs contributed directly to formation of calluses by the human bone matrix produced.

Figure 39A:
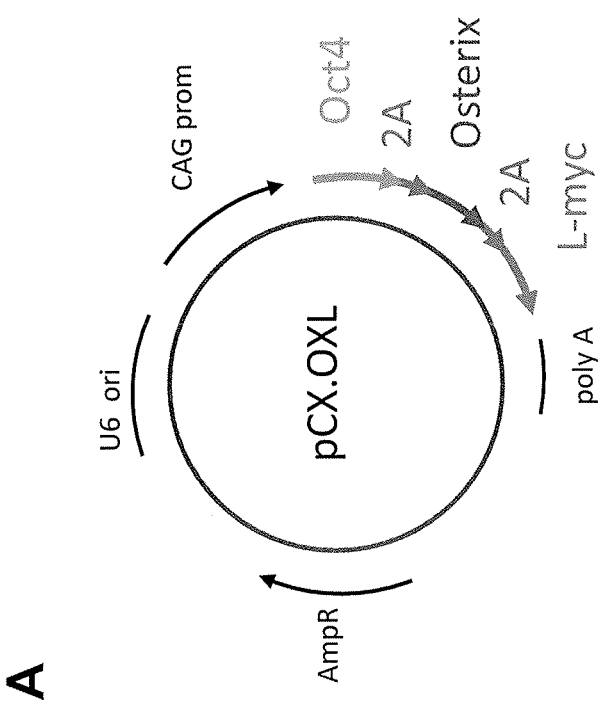
FIG. 39A is an illustration for showing reprogramming of human fibroblasts into osteoblasts by gene introduction using a plasmid vector.
Figure 39B:
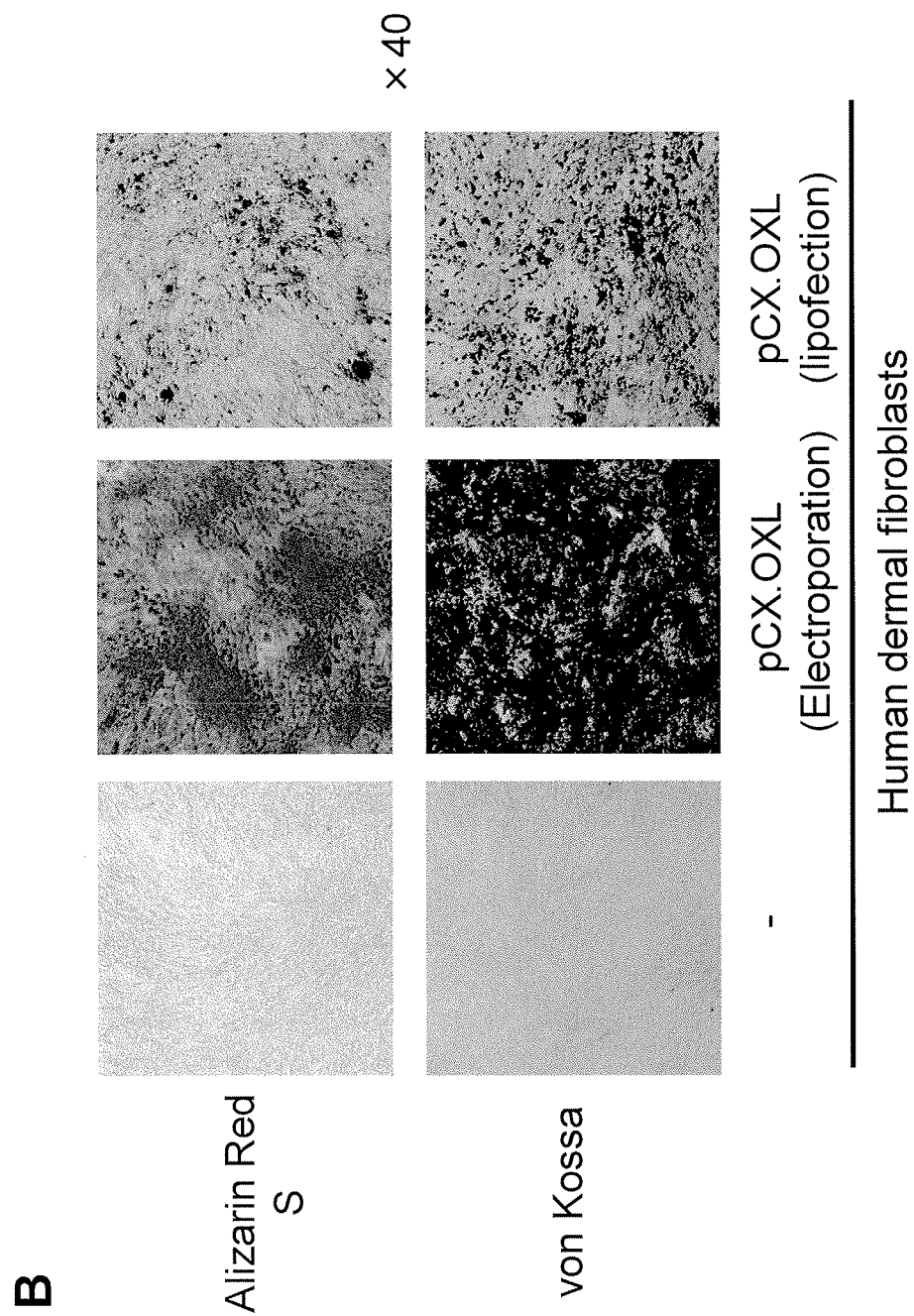
FIG. 39B is a result of reprogramming of human fibroblasts into osteoblasts by gene introduction using a plasmid vector.

(36) Human Fibroblasts can be Reprogrammed to Osteoblasts by Gene Introduction with a Plasmid Vector (FIG. 39a and FIG. 39b)

A plasmid vector, pCX.OXL (FIG. 39a), was constructed as described below. An expression unit for a chimeric protein, which included: three genes, Oct4, Osterix, and L-myc, ligated in this order from the N-terminal; and self-cleaving 2A peptides inserted between Oct4 and Osterix and between Osterix and L-myc, was incorporated into a plasmid vector pCX. The pCX.OXL was introduced into normal human dermal fibroblasts by an electroporation (Neon) (center) or lipofection (X-treme Gene 9) (right) method, and the cells were cultured in an inducing medium for 28 days. The cells and normal human dermal fibroblasts obtained without introduction of the genes (left) were subjected to Aalizarin Red S (above) and von Kossa staining (below) (FIG. 39b). It was found that, when the three factors, Oct4, Osterix, and L-myc, were introduced by gene introduction with the plasmid vector, fibroblasts were converted into osteoblasts capable of producing a large amount of calcified bone matrix.

Figure 40A:
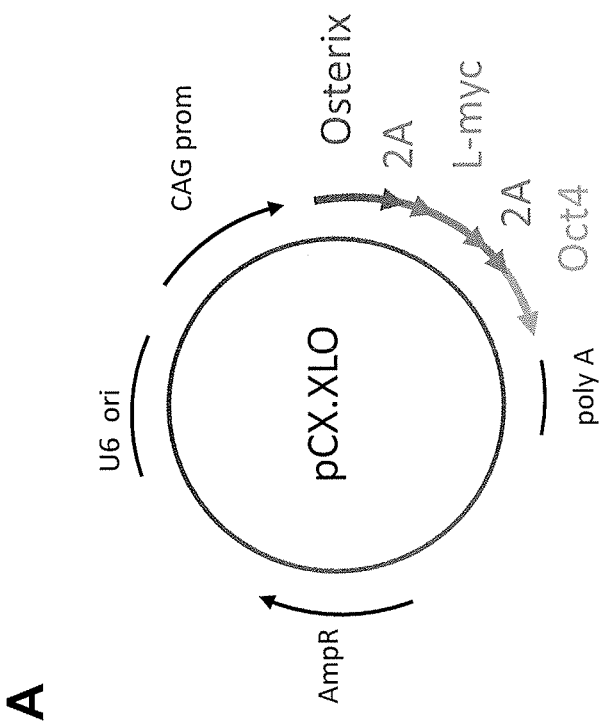
FIG. 40A is an illustration for showing reprogramming of human fibroblasts into osteoblasts by gene introduction using a plasmid vector.
Figure 40B:
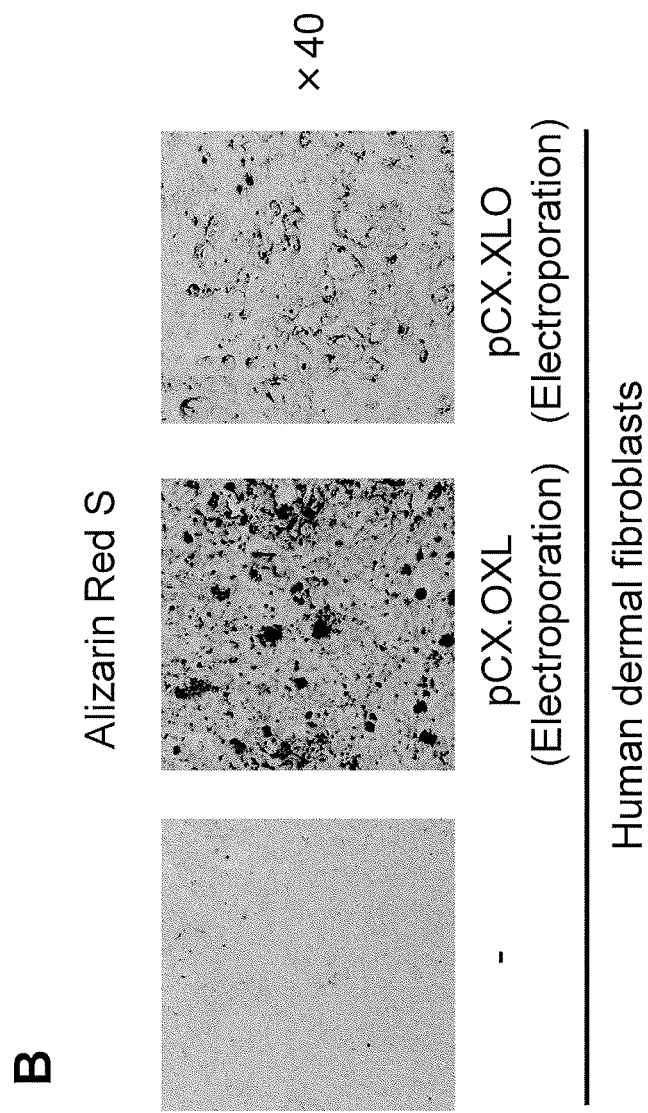
FIG. 40B is a result of reprogramming of human fibroblasts into osteoblasts by gene introduction using a plasmid vector.

(37) Human Fibroblasts can be Reprogrammed to Osteoblasts by Gene Introduction with a Plasmid Vector (FIG. 40a and FIG. 40b)

A plasmid vector, pCX.XLO (FIG. 40a), was constructed as described below. An expression unit for a chimeric protein, which included: three genes, Osterix, L-myc, and Oct4, ligated in this order from the N-terminal; and self-cleaving 2A peptides inserted between Osterix and L-myc and between L-myc and Oct4, was incorporated into a plasmid vector pCX. pCX.XLO and pCX.OXL (FIG. 39*a*) were introduced into normal human dermal fibroblasts by an electroporation (Neon) method, and the cells were cultured in an inducing medium for 28 days. The cells and normal human dermal fibroblasts obtained without introduction of the genes (left) were subjected to Alizarin Red S staining (FIG. 40*b*). It was found that, when the three factors, Oct4, Osterix, and L-myc, were introduced with the plasmid vector, the efficiency of conversion into osteoblasts varied depending on the order of the three genes aligned in the expression unit. The efficiency in the case of pCX.OXL was higher than that in the case of pCX.XLO.

Figure 41:
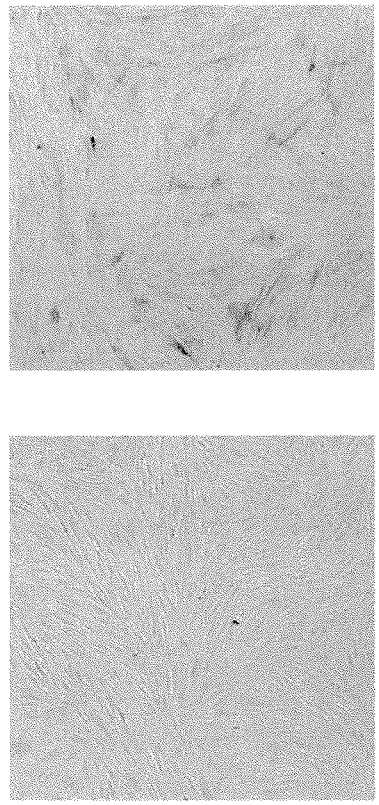
FIG. 41 is a result of reprogramming of human fibroblasts into osteoblasts in a medium free of foreign proteins.

(38) Human Fibroblasts can be Reprogrammed to Osteoblasts in a Medium Free of Foreign Proteins (FIG. 41)

The pCX.OXL constructed as illustrated in FIG. 39*a* was introduced into normal human dermal fibroblasts by an electroporation (Neon) method. After that, the cells were cultured in an osteoinductive medium containing no bovine fetal serum and containing 2% human serum. Five days later, the cells were subjected to ALP staining in the same manner as shown in FIG. 5 (FIG. 41). It was found that the human fibroblasts were able to be reprogrammed to osteoblasts in the medium free of foreign proteins.

Figure 42:
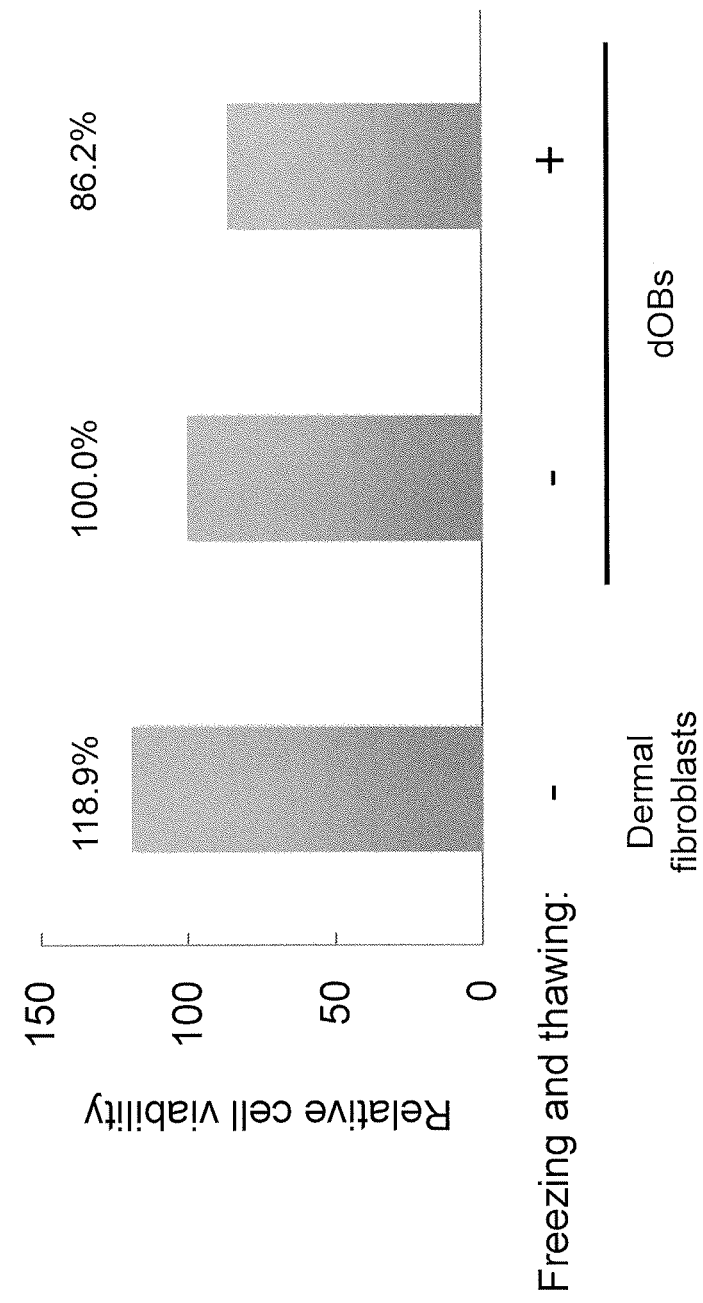
FIG. 42 is a result showing viability after freezing and thawing of human osteoblasts induced from human fibroblasts by direct reprogramming in a medium free of foreign proteins.

(39) Human Osteoblasts Induced from Human Fibroblasts by Direct Reprogramming in a Medium Free of Foreign Proteins can be Stored in Frozen State (FIG. 42)

The pCX.OXL constructed as illustrated in FIG. 39 was introduced into normal human dermal fibroblasts by an electroporation (Neon) method. After 14-day culture, part of the cells were frozen with liquid nitrogen, stored at −80° C. in a freezer, thawed the next day, and cultured for an additional 5 days (right). Other partial cells were cultured without freezing and thawing (center). Those cells and normal human dermal fibroblasts obtained without introduction of the genes (left) were subjected to tetrazolium salt assay using WST8 to quantify viability of the cells (FIG. 42). It was found that, even when the osteoblasts induced from the human fibroblasts by direct reprogramming were subjected to freezing and thawing, the viability did not significantly decrease.

The invention claimed is:

1. A method of generating an osteoblast from a somatic cell of a mammal, the method comprising introducing a reprogramming-related gene or an expression product thereof into the somatic cell, wherein the osteoblast is directly induced from the somatic cell without first becoming an induced pluripotent stem (iPS) cell or an embryonic stem (ES) cell, and wherein the reprogramming-related gene or the expression product thereof to be introduced into the somatic cell consists of one combination selected from the group consisting of Oct4L, Oct4M, and Oct4LM, where M represents "c-Myc" and L represents "L-Myc".

2. A method of generating an osteoblast from a somatic cell of a mammal, the method comprising introducing a combination of a bone-related gene or an expression product thereof and a reprogramming-related gene or an expression product thereof into the somatic cell,
   wherein the osteoblast is directly induced from the somatic cell without first becoming an induced pluripotent stem (iPS) cell or an embryonic stem (ES) cell, and
   wherein the combination of the bone-related gene or the expression product thereof and the reprogramming-related gene or the expression product thereof to be introduced into the somatic cell consists of one combination selected from the group consisting of RD Oct4L, D Oct4ML, OD Oct4L, O Oct4L, O Oct4M, OD Oct4L, RO Oct4L, D Oct4M, O Oct4, and D Oct4, where R represents "Runx2", O represents "Osterix", D represents "Dlx5", M represents "c-Myc", and L represents "L-Myc".

3. The method according to claim 1, wherein the somatic cell comprises a fibroblast or a gingival cell.

4. The method according to claim 2, wherein the combination of the bone-related gene or the expression product thereof and the reprogramming-related gene or the expression product thereof to be introduced into the somatic cell consists of one combination selected from the group consisting of RD Oct4L, D Oct4ML, OD Oct4L, O Oct4L, O Oct4M, OD Oct4, and D Oct4L, where R represents "Runx2", O represents "Osterix", D represents "Dlx5", M represents "c-Myc", and L represents "L-Myc".

5. The method according to claim 2, wherein the combination of the bone-related gene or the expression product thereof and the reprogramming-related gene or the expression product thereof to be introduced into the somatic cell consists of one combination selected from the group consisting of RD Oct4L and D Oct4ML.

6. The method according to claim 2, wherein the somatic cell comprises a fibroblast or a gingival cell.

* * * * *

SEQUENCE LISTING

```
<160> NUMBER OF SEQ ID NOS: 44

<210> SEQ ID NO 1
<211> LENGTH: 27
<212> TYPE: DNA
<213> ORGANISM: Artificial
<220> FEATURE:
<223> OTHER INFORMATION: Sense Primer for osteocalcin

<400> SEQUENCE: 1
gtgtatttgg tagttatagt tatttgg                                        27

<210> SEQ ID NO 2
<211> LENGTH: 26
<212> TYPE: DNA
<213> ORGANISM: Artificial
<220> FEATURE:
<223> OTHER INFORMATION: Antisense Primer for osteocalcin

<400> SEQUENCE: 2
cctcaaatta aacactaact aaactc                                         26

<210> SEQ ID NO 3
<211> LENGTH: 45
<212> TYPE: DNA
<213> ORGANISM: Artificial
<220> FEATURE:
<223> OTHER INFORMATION: Forward Primer for hRunx2

<400> SEQUENCE: 3
atcccagtgt ggtggtacgg gcccaccatg cgtattcccg tagat                    45

<210> SEQ ID NO 4
<211> LENGTH: 45
<212> TYPE: DNA
<213> ORGANISM: Artificial
<220> FEATURE:
<223> OTHER INFORMATION: Reverse Primer for hRunx2

<400> SEQUENCE: 4
```
tagcgaccgg cgctcagctg ggaggcccta atatggtcgc caaac        45

<210> SEQ ID NO 5
<211> LENGTH: 45
<212> TYPE: DNA
<213> ORGANISM: Artificial
<220> FEATURE:
<223> OTHER INFORMATION: Forward Primer for hOsterix

<400> SEQUENCE: 5
atcccagtgt ggtggtacgg gctcaggatg gcgtcctccc tgctt        45

<210> SEQ ID NO 6
<211> LENGTH: 45
<212> TYPE: DNA
<213> ORGANISM: Artificial
<220> FEATURE:
<223> OTHER INFORMATION: Reverse Primer for hOsterix

<400> SEQUENCE: 6
tagcgaccgg cgctcagctg gcccggctca gatctccagc aagtt        45

<210> SEQ ID NO 7
<211> LENGTH: 42
<212> TYPE: DNA
<213> ORGANISM: Artificial
<220> FEATURE:
<223> OTHER INFORMATION: Forward Primer for hDlx5

<400> SEQUENCE: 7
atcccagtgt ggtggtacgg gatgacagga gtgtttgaca ga        42

<210> SEQ ID NO 8
<211> LENGTH: 42
<212> TYPE: DNA
<213> ORGANISM: Artificial
<220> FEATURE:
<223> OTHER INFORMATION: Reverse Primer for hDlx5

<400> SEQUENCE: 8
tagcgaccgg cgctcagctg gctaatagag tgtcccggag gc        42

<210> SEQ ID NO 9
<211> LENGTH: 21
<212> TYPE: DNA
<213> ORGANISM: Artificial
<220> FEATURE:
<223> OTHER INFORMATION: Primer for Sequencing pMXs.hRunx2

<400> SEQUENCE: 9
gtccgccgac accagactaa g        21

<210> SEQ ID NO 10
<211> LENGTH: 21
<212> TYPE: DNA
<213> ORGANISM: Artificial
<220> FEATURE:
<223> OTHER INFORMATION: Primer for Sequencing pMXs.hRunx2

<400> SEQUENCE: 10
agcctgcagc ccggcaaaat g        21

<210> SEQ ID NO 11
<211> LENGTH: 21
<212> TYPE: DNA

```
<213> ORGANISM: Artificial
<220> FEATURE:
<223> OTHER INFORMATION: Primer for Sequencing pMXs.hRunx2

<400> SEQUENCE: 11
aacttcctgt gctcggtgct g                                          21

<210> SEQ ID NO 12
<211> LENGTH: 21
<212> TYPE: DNA
<213> ORGANISM: Artificial
<220> FEATURE:
<223> OTHER INFORMATION: Primer for Sequencing pMXs.hRunx2

<400> SEQUENCE: 12
aattaaagtt acagtagatg g                                          21

<210> SEQ ID NO 13
<211> LENGTH: 21
<212> TYPE: DNA
<213> ORGANISM: Artificial
<220> FEATURE:
<223> OTHER INFORMATION: Primer for Sequencing pMXs.hRunx2

<400> SEQUENCE: 13
atgaccagtc ttacccctcc t                                          21

<210> SEQ ID NO 14
<211> LENGTH: 21
<212> TYPE: DNA
<213> ORGANISM: Artificial
<220> FEATURE:
<223> OTHER INFORMATION: Primer for Sequencing pMXs.hRunx2

<400> SEQUENCE: 14
aatgcactat ccagccacct t                                          21

<210> SEQ ID NO 15
<211> LENGTH: 21
<212> TYPE: DNA
<213> ORGANISM: Artificial
<220> FEATURE:
<223> OTHER INFORMATION: Primer for Sequencing pMXs.hRunx2

<400> SEQUENCE: 15
aatggcagca cgctattaaa t                                          21

<210> SEQ ID NO 16
<211> LENGTH: 24
<212> TYPE: DNA
<213> ORGANISM: Artificial
<220> FEATURE:
<223> OTHER INFORMATION: Primer for Sequencing pMXs.hOsterix

<400> SEQUENCE: 16
cacgtgaagg ctgccgaccc cggg                                       24

<210> SEQ ID NO 17
<211> LENGTH: 24
<212> TYPE: DNA
<213> ORGANISM: Artificial
<220> FEATURE:
<223> OTHER INFORMATION: Primer for Sequencing pMXs.hOsterix

<400> SEQUENCE: 17
gtgacctttc agcctccaaa acca                                       24
```

<210> SEQ ID NO 18
<211> LENGTH: 24
<212> TYPE: DNA
<213> ORGANISM: Artificial
<220> FEATURE:
<223> OTHER INFORMATION: Primer for Sequencing pMXs.hOsterix

<400> SEQUENCE: 18
aacactccta ctccatggtg ggat                                          24

<210> SEQ ID NO 19
<211> LENGTH: 24
<212> TYPE: DNA
<213> ORGANISM: Artificial
<220> FEATURE:
<223> OTHER INFORMATION: Primer for Sequencing pMXs.hOsterix

<400> SEQUENCE: 19
acggggtgca agcactgggg gtag                                          24

<210> SEQ ID NO 20
<211> LENGTH: 24
<212> TYPE: DNA
<213> ORGANISM: Artificial
<220> FEATURE:
<223> OTHER INFORMATION: Primer for Sequencing pMXs.hOsterix

<400> SEQUENCE: 20
agttcacctg cctgctctgc tcca                                          24

<210> SEQ ID NO 21
<211> LENGTH: 21
<212> TYPE: DNA
<213> ORGANISM: Artificial
<220> FEATURE:
<223> OTHER INFORMATION: Primer for Sequencing pMXs.hDlx5

<400> SEQUENCE: 21
ttactaacag cccctctctc c                                             21

<210> SEQ ID NO 22
<211> LENGTH: 21
<212> TYPE: DNA
<213> ORGANISM: Artificial
<220> FEATURE:
<223> OTHER INFORMATION: Primer for Sequencing pMXs.hDlx5

<400> SEQUENCE: 22
agaagggtcc ccagcatccg a                                             21

<210> SEQ ID NO 23
<211> LENGTH: 21
<212> TYPE: DNA
<213> ORGANISM: Artificial
<220> FEATURE:
<223> OTHER INFORMATION: Primer for Sequencing pMXs.hDlx5

<400> SEQUENCE: 23
acaaccgcgt cccaagcgcc a                                             21

<210> SEQ ID NO 24
<211> LENGTH: 21
<212> TYPE: DNA
<213> ORGANISM: Artificial
<220> FEATURE:

<223> OTHER INFORMATION: Primer for Sequencing pMXs.hDlx5

<400> SEQUENCE: 24
accctcatgc ccaccctccg a                                              21

<210> SEQ ID NO 25
<211> LENGTH: 20
<212> TYPE: DNA
<213> ORGANISM: Artificial
<220> FEATURE:
<223> OTHER INFORMATION: Forward Primer for hOC

<400> SEQUENCE: 25 tgagagcccct cacactcctc                                               20

<210> SEQ ID NO 26
<211> LENGTH: 20
<212> TYPE: DNA
<213> ORGANISM: Artificial
<220> FEATURE:
<223> OTHER INFORMATION: Reverse Primer for hOC

<400> SEQUENCE: 26
acctttgctg gactctgcac                                                20

<210> SEQ ID NO 27
<211> LENGTH: 20
<212> TYPE: DNA
<213> ORGANISM: Artificial
<220> FEATURE:
<223> OTHER INFORMATION: Forward Primer for hBSP

<400> SEQUENCE: 27
caatctgtgc cactcactgc                                                20

<210> SEQ ID NO 28
<211> LENGTH: 22
<212> TYPE: DNA
<213> ORGANISM: Artificial
<220> FEATURE:
<223> OTHER INFORMATION: Reverse Primer for hBSP

<400> SEQUENCE: 28
cagtcttcat tttggtgatt gc                                             22

<210> SEQ ID NO 29
<211> LENGTH: 20
<212> TYPE: DNA
<213> ORGANISM: Artificial
<220> FEATURE:
<223> OTHER INFORMATION: Forward Primer for hREX-1

<400> SEQUENCE: 29
ggatctccca cctttccaag                                                20

<210> SEQ ID NO 30
<211> LENGTH: 19
<212> TYPE: DNA
<213> ORGANISM: Artificial
<220> FEATURE:
<223> OTHER INFORMATION: Reverse Primer for hREX-1

<400> SEQUENCE: 30
gcaggtagca cacctcctg                                                 19

-continued

```
<210> SEQ ID NO 31
<211> LENGTH: 20
<212> TYPE: DNA
<213> ORGANISM: Artificial
<220> FEATURE:
<223> OTHER INFORMATION: Forward Primer for hNanog

<400> SEQUENCE: 31
atgcctcaca cggagactgt                                                   20

<210> SEQ ID NO 32
<211> LENGTH: 20
<212> TYPE: DNA
<213> ORGANISM: Artificial
<220> FEATURE:
<223> OTHER INFORMATION: Reverse Primer for hNanog

<400> SEQUENCE: 32
cagggctgtc ctgaataagc                                                   20

<210> SEQ ID NO 33
<211> LENGTH: 20
<212> TYPE: DNA
<213> ORGANISM: Artificial Sequence
<220> FEATURE:
<223> OTHER INFORMATION: Forward Primer for hOC

<400> SEQUENCE: 33
tgagagccct cacactcctc                                                   20

<210> SEQ ID NO 34
<211> LENGTH: 20
<212> TYPE: DNA
<213> ORGANISM: Artificial Sequence
<220> FEATURE:
<223> OTHER INFORMATION: Reverse Primer for hOC

<400> SEQUENCE: 34
acctttgctg gactctgcac                                                   20

<210> SEQ ID NO 35
<211> LENGTH: 20
<212> TYPE: DNA
<213> ORGANISM: Artificial Sequence
<220> FEATURE:
<223> OTHER INFORMATION: Forward Primer for hBSP

<400> SEQUENCE: 35
caatctgtgc cactcactgc                                                   20

<210> SEQ ID NO 36
<211> LENGTH: 22
<212> TYPE: DNA
<213> ORGANISM: Artificial Sequence
<220> FEATURE:
<223> OTHER INFORMATION: Reverse Primer for hBSP

<400> SEQUENCE: 36
cagtcttcat tttggtgatt gc                                                22

<210> SEQ ID NO 37
<211> LENGTH: 24
<212> TYPE: DNA
<213> ORGANISM: Artificial Sequence
<220> FEATURE:
<223> OTHER INFORMATION: Forward Primer for hALP
```

```
<400> SEQUENCE: 37
cctgccttac taactcctta gtgc                                          24

<210> SEQ ID NO 38
<211> LENGTH: 20
<212> TYPE: DNA
<213> ORGANISM: Artificial Sequence
<220> FEATURE:
<223> OTHER INFORMATION: Reverse Primer

<400> SEQUENCE: 38
cgttggtgtt gagcttctga                                               20

<210> SEQ ID NO 39
<211> LENGTH: 20
<212> TYPE: DNA
<213> ORGANISM: Artificial Sequence
<220> FEATURE:
<223> OTHER INFORMATION: Forward Primer for hCOL1A

<400> SEQUENCE: 39
ctggagaggc tggtactgct                                               20

<210> SEQ ID NO 40
<211> LENGTH: 20
<212> TYPE: DNA
<213> ORGANISM: Artificial Sequence
<220> FEATURE:
<223> OTHER INFORMATION: Reverse Primer for hCOL1A

<400> SEQUENCE: 40
agcaccaaga agaccctgag                                               20

<210> SEQ ID NO 41
<211> LENGTH: 15
<212> TYPE: DNA
<213> ORGANISM: Artificial Sequence
<220> FEATURE:
<223> OTHER INFORMATION: Forward Primer for endogenous Runx2

<400> SEQUENCE: 41
ctatgcgtat tcccg                                                    15

<210> SEQ ID NO 42
<211> LENGTH: 19
<212> TYPE: DNA
<213> ORGANISM: Artificial Sequence
<220> FEATURE:
<223> OTHER INFORMATION: Reverse Primer for endogenous Runx2

<400> SEQUENCE: 42
gggctcacgt cgctcattt                                                19

<210> SEQ ID NO 43
<211> LENGTH: 21
<212> TYPE: DNA
<213> ORGANISM: Artificial Sequence
<220> FEATURE:
<223> OTHER INFORMATION: Forward Primer for endogenous Osterix

<400> SEQUENCE: 43
cagctctctc catctgcctg g                                             21

<210> SEQ ID NO 44
<211> LENGTH: 22
```

```
<212> TYPE: DNA
<213> ORGANISM: Artificial Sequence
<220> FEATURE:
<223> OTHER INFORMATION: Reverse Primer for endogenous Osterix

<400> SEQUENCE: 44
gggactggag ccatagtgaa ct                                              22
```